US009927440B2

(12) United States Patent
Hellinga et al.

(10) Patent No.: US 9,927,440 B2
(45) Date of Patent: Mar. 27, 2018

(54) PROTEIN ENGINEERING

(75) Inventors: Homme W. Hellinga, Durham, NC (US); Malin J. Allert, Raleigh, NC (US)

(73) Assignee: Duke University, Durham, NC (US)

( * ) Notice: Subject to any disclaimer, the term of this patent is extended or adjusted under 35 U.S.C. 154(b) by 217 days.

(21) Appl. No.: 12/954,317

(22) Filed: Nov. 24, 2010

(65) Prior Publication Data

US 2011/0171737 A1 Jul. 14, 2011

Related U.S. Application Data

(60) Provisional application No. 61/264,602, filed on Nov. 25, 2009, provisional application No. 61/308,553, filed on Feb. 26, 2010.

(51) Int. Cl.
*G01N 33/53* (2006.01)
*G01N 33/68* (2006.01)
*C12N 15/67* (2006.01)
*G06F 19/16* (2011.01)
*G06F 19/18* (2011.01)

(52) U.S. Cl.
CPC ......... *G01N 33/6803* (2013.01); *C12N 15/67* (2013.01); *G06F 19/16* (2013.01); *G06F 19/18* (2013.01)

(58) Field of Classification Search
CPC .......... G06F 19/00; G06F 19/22; G06F 17/50; G06F 19/20; G06F 19/26; C12N 2800/22; C12N 15/67; G06Q 30/0629
See application file for complete search history.

(56) References Cited

U.S. PATENT DOCUMENTS

| | | | |
|---|---|---|---|
| 2002/0031818 A1 | 3/2002 | Ronai et al. | |
| 2007/0048263 A1* | 3/2007 | Meyer | 424/85.2 |
| 2008/0051404 A1 | 2/2008 | Claiborne et al. | |

OTHER PUBLICATIONS

Kudla, Grzegorz et al, 2006 PLoS Biol 4: e180.*
Kozak 2005 Gene 361: 13-37.*
Voges et al 2004 Biochemical and Biophysical Research Communications 318: 601-614.*
Ahn, J.H. et al., "Cell-free synthesis of recombinant proteins from PCR-amplified genes at a comparable productivity to that of plasmid-based reactions," Biochemistry and Biophysical Research Communications (2005) 338:1346-1352.
Allert, M. et al., "Multifactorial determinants of protein expression in prokaryotic open reading frames" Journal of Molecular Biology, Oct. 8, 2010 (16 pages).
Bai, Y.W. et al., "Protein stability parameters measured by hydrogen-exchange," Proteins Structure, Function, and Genetics (1994) 20(1):4-14.
Bai, Y.W. et al., "Thermodynamic parameters from hydrogen exchange measurements," Energetics of Biological Macromolecules, Methods in Enzymology (1995) 259:344-356.
Bava, K.A. et al., "ProTherm, version 4.0: thermodynamic database for proteins and mutants," Nucl. Acids Res. (2004) 32:D120-121.
Brannigan et al., "Protein engineering 20 years on" Nature reviews. Molecular cell biology. (2002) 3:964-970.
Caruthers, M.H. et al., "Deoxyoligonucleotide synthesis via the phosphoramidite method," Gene Amplification and Analysis (1983) 3:1-26.
Caruthers, M.H. et al., "Chemical synthesis of deoxyoligonucleotides by the phosphoramidite method," Methods Enzymology (1987) 154:287-313.
Chaires, J.B., "Possible origin of differences between van't Hoff and calorimetric enthalpy estimates," Biophys. Chem. (1997) 64(1-3):15-23.
Chamberlin, M. et al., "New RNA polymerase from *Escherichia coli* infected with bacteriophage T7," Nature (1970) 228:227-231.
Cox, J.C. et al., "Protein fabrication automation," Protein Science (2007) 16(3):379-390.
Cuatrecasas, P. et al., "Catalytic properties and specificity of extracellular nuclease of *Staphylococcus aureus*," J. Biol. Chem. (1967) 242(7):1541-1547.
Curry, K.A. et al., "Effect of ribosome binding site on gene expression in *Escherichia coli*," DNA (1988) 7:173-179.
Davanloo, P. et al., "Cloning and expression of the gene for bacteriophage T7 RNA polymerase," Proc. Natl. Acad. Sci. USA (1984) 81:2035-2039.
Feng, Z.Y. et al., "On the nature of conformational openings: native and unfolded-state hydrogen and thiol-disulfide exchange studies of ferric aquomyoglobin," Journal of Molecular Biology (2001) 314(1):153-166.
Gao, X. et al., "Thermodynamically balanced inside-out (TBIO) PCR-based gene synthesis: a novel method of primer design for high-fidelity assembly of longer gene sequences," Nucl. Acids. Res. (2003) 31:e143.
Ghaemmaghami, S. et al., "A quantitative, high-throughput screen for protein stability," Proc. Natl. Aca. Sci. USA (2000) 97(15):8296-8301.
Gomez, J. et al., "The heat capacity of proteins," Proteins Structure, Function, and Genetics (1995) 22(4):404-412.
Green, S.M. et al., "Contributions of the polar, uncharged amino-acids to the stability of staphylococcal nuclease—evidence for mutational effects on the free-energy of the denatured state," Biochem. (1992) 31(25):5717-5728.
Ha, J.H. et al., "Changes in side chain packing during apomyoglobin folding characterized by pulsed thiol-disulfide exchange," Nature Structure Biology (1998) 5(8):730-737.
Hahn, G.H. et al., "Production of milligram quantities of recombinant proteins from PCR-amplified DNAs in a continuous-exchange cell-free protein synthesis system," Analytical Biochemistry (2006) 355:151-153.
Hopp, T. et al., "A short polypeptide marker sequence useful for recombinant protein identification and purification," Biotechnology (1988) 6(10):1204-1210.
Horton, R.M. et al., "Engineering hybrid genes without the use of restriction enzymes: gene splicing by overlap extension," Gene (1989) 77:61-68.

(Continued)

*Primary Examiner* — Mary K Zeman
(74) *Attorney, Agent, or Firm* — Mintz Levin Cohn Ferris Glovsky and Popeo, P.C.; Ingrid A. Beattie

(57) ABSTRACT

Methods of optimizing mRNA sequences for expression in host cells are provided. Methods of determining the stability of a protein are also provided. Methods of determining the affinity of a ligand for a protein are also provided.

12 Claims, 15 Drawing Sheets

(56) References Cited

OTHER PUBLICATIONS

Huyghues-Despointes, B. et al., "Measuring the Conformational Stability of a Protein by Hydrogen Exchange" Protein Structure, Stability and Folding, Humana Press Inc., Totowa, New Jersey (2001) 69-72.
Huyghues-Despointes, B.M.P. et al., "Protein conformational stabilities can be determined from hydrogen exchange rates," Nature Structre Biology (1999) 6(10):910-912.
Hvidt, A. et al., "Hydrogen exchange in proteins," Advances in Protein Chemistry (1966) 21:287-386.
Jewett, M. et al., "Mimicking the *Escherichia coli* cytoplasmic environment activates long-lived and efficient cell-free protein synthesis," Biotechnology Bioengineering (2004) 86(1):19-26.
Jewett, M. et al., "Substrate replenishment extends protein synthesis with an in vitro translation system designed to mimic the cytoplasm," Biotechnology and Bioengineering (2004) 87:465-472.
Jewett, M.C. et al., "Rapid expression and purification of 100 nmol quantities of active protein using cell-free protein synthesis," Biotechnology Progress (2004) 20:102-109.
Jha, S.K. et al., "Exploring the cooperativity of the fast folding reaction of a small protein using pulsed thiol labeling and mass spectrometry," J. Biol. Chem. (2007) 282(52):37479-37491.
Kawarasaki, Y. et al., "A long-lived batch reaction system of cell-free protein synthesis," Analytical Biochemistry (1995) 226:320-324.
Kido, m. et al., "RNAse E polypeptides lacking a carboxyl-terminal half suppress a mukB mutation in *Escherichia coli*," J. Bacteriol. (1996) 178:3917-3925.
Kim, D.M. et al., "Regeneration of adenosine triphosphate from glycolytic intermediates for cell-free protein synthesis," Biotechnology and Bioengineering (2001) 74:309-316.
Kim, J.S. et al., "Stability and folding of a mutant ribose-binding protein of *Escherichia coli*," Journal of Protein Chemistry (1996) 15(8):731-736.
Kim, R.G. et al., "Expression-independent consumption of substrates in cell-free expression system from *Escherichia coli*," Journal of Biotechnology (2000) 84:27-32.
Kudla et al., "Coding-Sequence Determinants of Gene Expression in *Escherichia coli*," Science (2009) 324:255-258.
Liu, D.V. et al., "Streamlining *Escherichia coli* S30 extract preparation for economical cell-free protein synthesis," Biotechnology Progress (2005) 21:460-465.
Lopez, P.J. et al., "The C-terminal half of RNase E, which organizes the *Escherichia coli* degradosome, participates in mRNA degradation but not rRNA processing in vivo," Molecular Microbiology (1999) 33:188-199.
Mertens, N. et al., "Increased stability of phage T7g10 mRNA is mediated by either a 5'- or a 3'-terminal stem-loop structure," Biological Chemistry (1996) 377:811-817.
Milne, J.S. et al., "Experimental study of the protein folding landscape: unfolding reactions in cytochrome c," Journal of Molecular Biology (1999) 290(3):811-822.
Mueller et al., "Putting Synthesis into Biology: A Viral View of Genetic Engineering through De Novo Gene and Genome Synthesis" Chem. Biol. (2009) 16:337-347.
Murray et al., "Codon usage in plant genes" Nucl. Acids Res. (1989) 17:477.
Pace, C.N. et al., "Substrate stabilization of lysozyme to thermal and guanidine-hydrochloride denaturation," J. Biol. Chem. (1980) 255(9):3862-3865.
Prabhu, N. V. et al., "Heat capacity in proteins," Ann. Rev. Phys. Chem. (2005) 56:521-548.
Prajapati, R.S. et al., "Identification and thermodynamic characterization of molten globule states of periplasmic binding proteins," Biochem. (2007) 46(36):10339-10352.
Prajapati, R.S. et al., "Thermodynamic effects of proline introduction on protein stability," Proteins (2007) 66(2):480-491.
Privalov, P., "Stability of proteins," Adv. Protein Chem. (1979) 33:167-241.
Razvi, A. et al., "Lessons in stability from thermophilic proteins," Prot. Sci. (2006) 15(7):1569-1578.
Rees, D. et al., "Some thermodynamic implications for the thermostability of proteins," Prot. Sci. (2001) 10:1187-1194.
Schellman, J.A., "Macromolecular binding," Biopolymers (1975) 14(5):999-1018.
Serpersu, E.H. et al., "Kinetic and magnetic-resonance studies of effects of genetic substitution of a Ca-2+-liganding amino-acid in staphylococcal nuclease," Biochem. (1986) 25(1):68-77.
Shine, J. et al., "The 3'-terminal sequence of *Escherichia coli* 16S ribosomal RNA: complementarity to nonsense triplets and ribosome binding sites," Proc. Natl. Acad. Sci. USA (1974) 71:1342-1346.
Silverman, J.A. et al., "The equilibrium unfolding pathway of a (beta/alpha)8 barrel," Journal of Molecular Biology (2002) 324(5):1031-1040.
Sridevi, K. et al., "Unfolding rates of barstar determined in native and low denaturant conditions indicate the presence of intermediates," Biochem. (2002) 41(5):1568-1578.
Swint-Kruse, L. et al., "Temperature and pH dependences of hydrogen exchange and global stability for ovomucoid third domain," Biochem. (1996) 35(1):171-180.
Talla-Singh, D. et al., "Refinement of noncalorimetric determination of the change in heat capacity, $\Delta Cp$, of protein unfolding and validation across a wide temperature range," Proteins (2008) 71(4):1607-1616.
Wada et al., Nucleic Acids Research (1990) 18:2367-2368.
Waldron, T.T. et al., "Stabilization of proteins by ligand binding: application to drug screening and determination of unfolding energetics," Biochem. (2003) 42(17):5058-5064.
Wyman, J., "Linked functions and reciprocal effects in hemoglobin: a second look," Advances in Protein Chemistry (1964) 19:223-286.
Zuker et al., "Optimal computer folding of large RNA sequences using thermodynamics and auxiliary information" Nucl. Acids Res. 9:133-148.
Bashan et al., Correlating ribosome function with high-resolution structures. Trends Microbiol. 2008;16:326-335.
Carpousis, A. The RNA degradosome of *Escherichia coli*: an mRNA-degrading machine assembled on RNase E. Annu Rev Microbiol. 2007;61:71-87.
Freier et al., Improved free-energy parameters for predictions of RNA duplex stability. Proc Natl Acad Sci U S A. Dec. 1986;83(24):9373-7.
Hershberg et al., Selection on codon bias. Annu Rev Genet. 2008;42:287-99.
Iost et al., DEAD-box RNA helicases in *Escherichia coli*. Nucleic Acids Res. 2006;34(15):4189-97.
Jaeger et al., Improved predictions of secondary structures for RNA. Proc Natl Acad Sci U S A. Oct. 1989;86(20):7706-10.
Marintchev et al., Translation initiation: structures, mechanisms and evolution. Q Rev Biophys. Aug.-Nov. 2004;37(3-4):197-284.
Petry et al., The termination of translation. Curr Opin Struct Biol. 2008;18:70-77.
Ramakrishnan, V. Ribosome structure and the mechanism of translation. Cell. 2002;108:557-572.
Rocak et al., DEAD-box proteins: the driving forces behind RNA metabolism. Nat Rev Mol Cell Biol. Mar. 2004;5(3):232-41.
Steitz, T. A structural understanding of the dynamic ribosome machine. Nat Rev Mol Cell Biol. 2008;9:242-253.
Takyar S, Hickerson RP, Noller HF. mRNA helicase activity of the ribosome. Cell. Jan. 14, 2005;120(1):49-58.
Wen et al., Following translation by single ribosomes one codon at a time. Nature. 2008;452:598-603.

\* cited by examiner

AAT_THET8. Thermus thermophilus Aspartate aminotransferase (SEQ ID NO:1)

M R G L S R R V Q A M K P S A T V A V N A K A L E L R R Q G V D L V A L T A G E
P D F D T P E H V K E A A R R A L A Q G K T K Y A P P A G I P E L R E A L A E K
F R R E N G L S V T P E E T I V T V G G K Q A L F N L F Q A I L D P G D E V I V
L S P Y W V S Y P E M V R F A G G V V V E V E T L P E E G F V P D P E R V R R A
I T P R T K A L V V N S P N N P T G A V Y P K E V L E A L A R L A V E H D F Y L
V S D E I Y E H L L Y E G E H F S P G R V A P E H T L T V N G A A K A F A M T G
W R I G Y A C G P K E V I K A M A S V S S Q S T T S P D T I A Q W A T L E A L T
N Q E A S R A F V E M A R E A Y R R R R D L L L E G L T A L G L K A V R P S G A
F Y V L M D T S P I A P D E V R A A E R L L E A G V A V V P G T D F A A F G H V
R L S Y A T S E E N L R K A L E R F A R V L G R A

FABPL_CHICK. Gallus gallus Fatty acid-binding protein (SEQ ID NO:2)

M A F S G T W Q V Y A Q E N Y E E F L K A L A L P E D L I K M A R D I K P I V E
I Q Q K G D D F V V T S K T P R Q T V T N S F T L G K E A D I T T M D G K K L K
C T V H L A N G K L V T K S E K F S H E Q E V K G N E M V E T I T F G G V T L I
R R S K R V

TPIS_LEIME. Leishmania mexicana Triosephosphate isomerase (SEQ ID NO:3)

SEQUENCE LISTING

```
<160> NUMBER OF SEQ ID NOS: 18

<210> SEQ ID NO 1
<211> LENGTH: 394
<212> TYPE: PRT
<213> ORGANISM: Thermus thermophilus

<400> SEQUENCE: 1

Met Arg Gly Leu Ser Arg Arg Val Gln Ala Met Lys Pro Ser Ala Thr
1               5                   10                  15

Val Ala Val Asn Ala Lys Ala Leu Glu Leu Arg Arg Gln Gly Val Asp
            20                  25                  30

Leu Val Ala Leu Thr Ala Gly Glu Pro Asp Phe Asp Thr Pro Glu His
```

```
            35                  40                  45
Val Lys Glu Ala Ala Arg Arg Ala Leu Ala Gln Gly Lys Thr Lys Tyr
 50                  55                  60

Ala Pro Pro Ala Gly Ile Pro Glu Leu Arg Glu Ala Leu Ala Glu Lys
 65                  70                  75                  80

Phe Arg Arg Glu Asn Gly Leu Ser Val Thr Pro Glu Glu Thr Ile Val
                     85                  90                  95

Thr Val Gly Gly Lys Gln Ala Leu Phe Asn Leu Phe Gln Ala Ile Leu
                100                 105                 110

Asp Pro Gly Asp Glu Val Ile Val Leu Ser Pro Tyr Trp Val Ser Tyr
            115                 120                 125

Pro Glu Met Val Arg Phe Ala Gly Gly Val Val Glu Val Glu Thr
        130                 135                 140

Leu Pro Glu Glu Gly Phe Val Pro Asp Pro Arg Val Arg Arg Ala
145                 150                 155                 160

Ile Thr Pro Arg Thr Lys Ala Leu Val Val Asn Ser Pro Asn Asn Pro
                    165                 170                 175

Thr Gly Ala Val Tyr Pro Lys Glu Val Leu Glu Ala Leu Ala Arg Leu
                180                 185                 190

Ala Val Glu His Asp Phe Tyr Leu Val Ser Asp Glu Ile Tyr Glu His
            195                 200                 205

Leu Leu Tyr Glu Gly Glu His Phe Ser Pro Gly Arg Val Ala Pro Glu
210                 215                 220

His Thr Leu Thr Val Asn Gly Ala Ala Lys Ala Phe Ala Met Thr Gly
225                 230                 235                 240

Trp Arg Ile Gly Tyr Ala Cys Gly Pro Lys Glu Val Ile Lys Ala Met
                    245                 250                 255

Ala Ser Val Ser Ser Gln Ser Thr Thr Ser Pro Asp Thr Ile Ala Gln
                260                 265                 270

Trp Ala Thr Leu Glu Ala Leu Thr Asn Gln Glu Ala Ser Arg Ala Phe
            275                 280                 285

Val Glu Met Ala Arg Glu Ala Tyr Arg Arg Arg Asp Leu Leu Leu
        290                 295                 300

Glu Gly Leu Thr Ala Leu Gly Leu Lys Ala Val Arg Pro Ser Gly Ala
305                 310                 315                 320

Phe Tyr Val Leu Met Asp Thr Ser Pro Ile Ala Pro Asp Glu Val Arg
                    325                 330                 335

Ala Ala Glu Arg Leu Leu Glu Ala Gly Val Ala Val Val Pro Gly Thr
                340                 345                 350

Asp Phe Ala Ala Phe Gly His Val Arg Leu Ser Tyr Ala Thr Ser Glu
            355                 360                 365

Glu Asn Leu Arg Lys Ala Leu Glu Arg Phe Ala Arg Val Leu Gly Arg
        370                 375                 380

Ala Gly Gly Ser His His His His His
385                 390

<210> SEQ ID NO 2
<211> LENGTH: 135
<212> TYPE: PRT
<213> ORGANISM: Gallus gallus

<400> SEQUENCE: 2

Met Ala Phe Ser Gly Thr Trp Gln Val Tyr Ala Gln Glu Asn Tyr Glu
 1               5                  10                  15
```

```
Glu Phe Leu Lys Ala Leu Ala Leu Pro Glu Asp Leu Ile Lys Met Ala
            20                  25                  30

Arg Asp Ile Lys Pro Ile Val Glu Ile Gln Gln Lys Gly Asp Asp Phe
        35                  40                  45

Val Val Thr Ser Lys Thr Pro Arg Gln Thr Val Thr Asn Ser Phe Thr
50                  55                  60

Leu Gly Lys Glu Ala Asp Ile Thr Thr Met Asp Gly Lys Lys Leu Lys
65                  70                  75                  80

Cys Thr Val His Leu Ala Asn Gly Lys Leu Val Cys Lys Ser Glu Lys
                85                  90                  95

Phe Ser His Glu Gln Glu Val Lys Gly Asn Glu Met Val Glu Thr Ile
            100                 105                 110

Thr Phe Gly Gly Val Thr Leu Ile Arg Arg Ser Lys Arg Val Gly Gly
        115                 120                 125

Ser His His His His His
        130                 135
```

<210> SEQ ID NO 3
<211> LENGTH: 260
<212> TYPE: PRT
<213> ORGANISM: Leishmania mexicana

<400> SEQUENCE: 3

```
Met Ser Ala Lys Pro Gln Pro Ile Ala Ala Asn Trp Lys Cys Asn
1               5                   10                  15

Gly Thr Thr Ala Ser Ile Glu Lys Leu Val Gln Val Phe Asn Glu His
            20                  25                  30

Thr Ile Ser His Asp Val Gln Cys Val Val Ala Pro Thr Phe Val His
        35                  40                  45

Ile Pro Leu Val Gln Ala Lys Leu Arg Asn Pro Lys Tyr Val Ile Ser
    50                  55                  60

Ala Glu Asn Ala Ile Ala Lys Ser Gly Ala Phe Thr Gly Glu Val Ser
65                  70                  75                  80

Met Pro Ile Leu Lys Asp Ile Gly Val His Trp Val Ile Leu Gly His
                85                  90                  95

Ser Glu Arg Arg Thr Tyr Tyr Gly Glu Thr Asp Glu Ile Val Ala Gln
            100                 105                 110

Lys Val Ser Glu Ala Cys Lys Gln Gly Phe Met Val Ile Ala Cys Ile
        115                 120                 125

Gly Glu Thr Leu Gln Gln Arg Glu Ala Asn Gln Thr Ala Lys Val Val
    130                 135                 140

Leu Ser Gln Thr Ser Ala Ile Ala Ala Lys Leu Thr Lys Asp Ala Trp
145                 150                 155                 160

Asn Gln Val Val Leu Ala Tyr Glu Pro Val Trp Ala Ile Gly Thr Gly
                165                 170                 175

Lys Val Ala Thr Pro Glu Gln Ala Gln Glu Val His Leu Leu Leu Arg
            180                 185                 190

Lys Trp Val Ser Glu Asn Ile Gly Thr Asp Val Ala Ala Lys Leu Arg
        195                 200                 205

Ile Leu Tyr Gly Gly Ser Val Asn Ala Ala Asn Ala Ala Thr Leu Tyr
    210                 215                 220

Ala Lys Pro Asp Ile Asn Gly Phe Leu Val Gly Gly Ala Ser Leu Lys
225                 230                 235                 240

Pro Glu Phe Arg Asp Ile Ile Asp Ala Thr Arg Gly Gly Ser His His
                245                 250                 255
```

His His His His
        260

<210> SEQ ID NO 4
<211> LENGTH: 260
<212> TYPE: PRT
<213> ORGANISM: Artificial
<220> FEATURE:
<223> OTHER INFORMATION: Synthetic

<400> SEQUENCE: 4

Met Ser Ala Lys Pro Gln Pro Ile Ala Ala Asn Trp Lys Cys Asn
1               5                   10                  15

Gly Thr Thr Ala Ser Ile Glu Lys Leu Val Gln Val Phe Asn Glu His
                20                  25                  30

Thr Ile Ser His Asp Val Gln Cys Val Val Ala Pro Thr Phe Val His
            35                  40                  45

Ile Pro Leu Val Gln Ala Lys Leu Arg Asn Pro Lys Tyr Val Ile Ser
    50                  55                  60

Ala Gln Asn Ala Ile Ala Lys Ser Gly Ala Phe Thr Gly Glu Val Ser
65                  70                  75                  80

Met Pro Ile Leu Lys Asp Ile Gly Val His Trp Val Ile Leu Gly His
                85                  90                  95

Ser Glu Arg Arg Thr Tyr Tyr Gly Glu Thr Asp Glu Ile Val Ala Gln
                100                 105                 110

Lys Val Ser Glu Ala Cys Lys Gln Gly Phe Met Val Ile Ala Cys Ile
            115                 120                 125

Gly Glu Thr Leu Gln Gln Arg Glu Ala Asn Gln Thr Ala Lys Val Val
    130                 135                 140

Leu Ser Gln Thr Ser Ala Ile Ala Ala Lys Leu Thr Lys Asp Ala Trp
145                 150                 155                 160

Asn Gln Val Val Leu Ala Tyr Glu Pro Val Trp Ala Ile Gly Thr Gly
                165                 170                 175

Lys Val Ala Thr Pro Glu Gln Ala Gln Glu Val His Leu Leu Leu Arg
            180                 185                 190

Lys Trp Val Ser Glu Asn Ile Gly Thr Asp Val Ala Ala Lys Leu Arg
        195                 200                 205

Ile Leu Tyr Gly Gly Ser Val Asn Ala Ala Asn Ala Ala Thr Leu Tyr
    210                 215                 220

Ala Lys Pro Asp Ile Asn Gly Phe Leu Val Gly Gly Ala Ser Leu Lys
225                 230                 235                 240

Pro Glu Phe Arg Asp Ile Ile Asp Ala Thr Arg Gly Gly Ser His His
                245                 250                 255

His His His His
        260

<210> SEQ ID NO 5
<211> LENGTH: 122
<212> TYPE: DNA
<213> ORGANISM: Artificial
<220> FEATURE:
<223> OTHER INFORMATION: Synthetic

<400> SEQUENCE: 5
cggcgtagag gatcgagatc tcgatcccgc gaaattaata cgactcacta taggggaatt     60
gtgagcggat aacaattccc ctctagaaat aattttgttt aactttaaga aggagatata    120

-continued cc                                                                                  122

<210> SEQ ID NO 6
<211> LENGTH: 137
<212> TYPE: DNA
<213> ORGANISM: Artificial
<220> FEATURE:
<223> OTHER INFORMATION: Synthetic

<400> SEQUENCE: 6
ggcggctccc accatcacca tcaccattaa tgagagatcc ggctgctaac aaagcccgaa      60
aggaagctga gttggctgct gccaccgctg agcaataact agcataaccc cttggggcct    120
ctaaacgggt cttgagg                                                    137

<210> SEQ ID NO 7
<211> LENGTH: 159
<212> TYPE: PRT
<213> ORGANISM: Staphylococcus aureus

<400> SEQUENCE: 7

Met Ala Thr Ser Thr Lys Lys Leu His Lys Glu Pro Ala Thr Leu Ile
1               5                   10                  15

Lys Ala Ile Asp Gly Asp Thr Val Lys Leu Met Tyr Lys Gly Gln Pro
            20                  25                  30

Met Thr Phe Arg Leu Leu Leu Val Asp Thr Pro Glu Thr Lys His Pro
        35                  40                  45

Lys Lys Gly Val Glu Lys Tyr Gly Pro Glu Ala Ser Ala Phe Thr Lys
    50                  55                  60

Lys Met Val Glu Asn Ala Lys Lys Ile Glu Val Glu Phe Asp Lys Gly
65                  70                  75                  80

Asn Arg Thr Asp Lys Tyr Gly Arg Gly Leu Ala Tyr Ile Tyr Ala Asp
                85                  90                  95

Gly Lys Met Val Asn Glu Ala Leu Val Arg Gln Gly Leu Ala Lys Val
            100                 105                 110

Ala Tyr Val Tyr Lys Pro Asn Asn Thr His Glu Gln His Leu Arg Lys
        115                 120                 125

Ser Glu Ala Gln Ala Lys Lys Glu Lys Leu Asn Ile Trp Ser Glu Asp
    130                 135                 140

Asn Ala Asp Ser Gly Gln Gly Gly Ser His His His His His
145                 150                 155

<210> SEQ ID NO 8
<211> LENGTH: 282
<212> TYPE: PRT
<213> ORGANISM: Escherichia coli

<400> SEQUENCE: 8

Met Lys Asp Thr Ile Ala Leu Val Val Ser Thr Leu Asn Asn Pro Phe
1               5                   10                  15

Phe Val Ser Leu Lys Asp Gly Ala Gln Lys Glu Ala Asp Lys Leu Gly
            20                  25                  30

Tyr Asn Leu Val Val Leu Asp Ser Gln Asn Asn Pro Ala Lys Glu Leu
        35                  40                  45

Ala Asn Val Gln Asp Leu Thr Val Arg Gly Thr Lys Ile Leu Leu Ile
    50                  55                  60

Asn Pro Thr Asp Ser Asp Ala Val Gly Asn Ala Val Lys Met Ala Asn
65                  70                  75                  80

-continued

```
Gln Ala Asn Ile Pro Val Ile Thr Leu Asp Arg Gln Ala Thr Lys Gly
                85                  90                  95
Glu Val Val Ser His Ile Ala Ser Asp Asn Val Leu Gly Gly Lys Ile
            100                 105                 110
Ala Gly Asp Tyr Ile Ala Lys Lys Ala Gly Glu Gly Ala Lys Val Ile
        115                 120                 125
Glu Leu Gln Gly Ile Ala Gly Thr Ser Ala Ala Arg Glu Arg Gly Glu
    130                 135                 140
Gly Phe Gln Gln Ala Val Ala Ala His Lys Phe Asn Val Leu Ala Ser
145                 150                 155                 160
Gln Pro Ala Asp Phe Asp Arg Ile Lys Gly Leu Asn Val Met Gln Asn
                165                 170                 175
Leu Leu Thr Ala His Pro Asp Val Gln Ala Val Phe Ala Gln Asn Asp
            180                 185                 190
Glu Met Ala Leu Gly Ala Leu Arg Ala Leu Gln Thr Ala Gly Lys Ser
        195                 200                 205
Asp Val Met Val Val Gly Phe Asp Gly Thr Pro Asp Gly Glu Lys Ala
    210                 215                 220
Val Asn Asp Gly Lys Leu Ala Ala Thr Ile Ala Gln Leu Pro Asp Gln
225                 230                 235                 240
Ile Gly Ala Lys Gly Val Glu Thr Ala Asp Lys Val Leu Lys Gly Glu
                245                 250                 255
Lys Val Gln Ala Lys Tyr Pro Val Asp Leu Lys Leu Val Val Lys Gln
            260                 265                 270
Asn Gly Gly Ser His His His His His His
        275                 280

<210> SEQ ID NO 9
<211> LENGTH: 380
<212> TYPE: PRT
<213> ORGANISM: Escherichia coli

<400> SEQUENCE: 9

Met Lys Ile Glu Glu Gly Lys Leu Val Ile Trp Ile Asn Gly Asp Lys
1               5                   10                  15
Gly Tyr Asn Gly Leu Ala Glu Val Gly Lys Lys Phe Glu Lys Asp Thr
            20                  25                  30
Gly Ile Lys Val Thr Val Glu His Pro Asp Lys Leu Glu Glu Lys Phe
        35                  40                  45
Pro Gln Val Ala Ala Thr Gly Asp Gly Pro Asp Ile Ile Phe Trp Ala
    50                  55                  60
His Asp Arg Phe Gly Gly Tyr Ala Gln Ser Gly Leu Leu Ala Glu Ile
65                  70                  75                  80
Thr Pro Asp Lys Ala Phe Gln Asp Lys Leu Tyr Pro Phe Thr Trp Asp
                85                  90                  95
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
        115                 120                 125
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
```

```
Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Arg
        355                 360                 365

Ile Thr Lys Gly Gly Ser His His His His His His
    370                 375                 380

<210> SEQ ID NO 10
<211> LENGTH: 159
<212> TYPE: PRT
<213> ORGANISM: Staphylococcus aureus

<400> SEQUENCE: 10

Met Ala Thr Ser Thr Lys Lys Leu His Lys Glu Pro Ala Thr Leu Ile
1               5                   10                  15

Lys Ala Ile Asp Gly Asp Thr Val Lys Leu Met Tyr Lys Gly Gln Pro
            20                  25                  30

Met Thr Cys Arg Leu Leu Leu Val Asp Thr Pro Glu Thr Lys His Pro
        35                  40                  45

Lys Lys Gly Val Glu Lys Tyr Gly Pro Glu Ala Ser Ala Phe Thr Lys
    50                  55                  60

Lys Met Val Glu Asn Ala Lys Lys Ile Glu Val Glu Phe Asp Lys Gly
65                  70                  75                  80

Asn Arg Thr Asp Lys Tyr Gly Arg Gly Leu Ala Tyr Ile Tyr Ala Asp
                85                  90                  95

Gly Lys Met Val Asn Glu Ala Leu Val Arg Gln Gly Leu Ala Lys Val
            100                 105                 110

Ala Tyr Val Tyr Lys Pro Asn Asn Thr His Glu Gln His Leu Arg Lys
        115                 120                 125

Ser Glu Ala Gln Ala Lys Lys Glu Lys Leu Asn Ile Trp Ser Glu Asp
    130                 135                 140

Asn Ala Asp Ser Gly Gln Gly Gly Ser His His His His His
145                 150                 155
```

-continued

```
<210> SEQ ID NO 11
<211> LENGTH: 159
<212> TYPE: PRT
<213> ORGANISM: Staphylococcus aureus

<400> SEQUENCE: 11

Met Ala Thr Ser Thr Lys Lys Leu His Lys Glu Pro Ala Thr Leu Ile
1               5                   10                  15

Lys Ala Ile Asp Gly Asp Thr Val Lys Leu Met Tyr Lys Gly Gln Pro
            20                  25                  30

Met Thr Phe Arg Cys Leu Leu Val Asp Thr Pro Glu Thr Lys His Pro
        35                  40                  45

Lys Lys Gly Val Glu Lys Tyr Gly Pro Glu Ala Ser Ala Phe Thr Lys
    50                  55                  60

Lys Met Val Glu Asn Ala Lys Lys Ile Glu Val Glu Phe Asp Lys Gly
65                  70                  75                  80

Asn Arg Thr Asp Lys Tyr Gly Arg Gly Leu Ala Tyr Ile Tyr Ala Asp
                85                  90                  95

Gly Lys Met Val Asn Glu Ala Leu Val Arg Gln Gly Leu Ala Lys Val
            100                 105                 110

Ala Tyr Val Tyr Lys Pro Asn Asn Thr His Glu Gln His Leu Arg Lys
        115                 120                 125

Ser Glu Ala Gln Ala Lys Lys Glu Lys Leu Asn Ile Trp Ser Glu Asp
    130                 135                 140

Asn Ala Asp Ser Gly Gln Gly Gly Ser His His His His His
145                 150                 155

<210> SEQ ID NO 12
<211> LENGTH: 282
<212> TYPE: PRT
<213> ORGANISM: Escherichia coli

<400> SEQUENCE: 12

Met Lys Asp Thr Ile Ala Leu Val Val Ser Thr Leu Asn Asn Pro Phe
1               5                   10                  15

Phe Val Ser Leu Lys Asp Gly Ala Gln Lys Glu Ala Asp Lys Leu Gly
            20                  25                  30

Tyr Asn Leu Val Val Leu Asp Ser Gln Asn Asn Pro Ala Lys Glu Leu
        35                  40                  45

Ala Asn Val Gln Asp Leu Thr Val Arg Gly Thr Lys Ile Cys Leu Ile
    50                  55                  60

Asn Pro Thr Asp Ser Asp Ala Val Gly Asn Ala Val Lys Met Ala Asn
65                  70                  75                  80

Gln Ala Asn Ile Pro Val Ile Thr Leu Asp Arg Gln Ala Thr Lys Gly
                85                  90                  95

Glu Val Val Ser His Ile Ala Ser Asp Asn Val Leu Gly Gly Lys Ile
            100                 105                 110

Ala Gly Asp Tyr Ile Ala Lys Lys Ala Gly Glu Gly Ala Lys Val Ile
        115                 120                 125

Glu Leu Gln Gly Ile Ala Gly Thr Ser Ala Ala Arg Glu Arg Gly Glu
    130                 135                 140

Gly Phe Gln Gln Ala Val Ala Ala His Lys Phe Asn Val Leu Ala Ser
145                 150                 155                 160

Gln Pro Ala Asp Phe Asp Arg Ile Lys Gly Leu Asn Val Met Gln Asn
                165                 170                 175

Leu Leu Thr Ala His Pro Asp Val Gln Ala Val Phe Ala Gln Asn Asp
```

```
            180                 185                 190
Glu Met Ala Leu Gly Ala Leu Arg Ala Leu Gln Thr Ala Gly Lys Ser
            195                 200                 205

Asp Val Met Val Val Gly Phe Asp Gly Thr Pro Asp Gly Glu Lys Ala
            210                 215                 220

Val Asn Asp Gly Lys Leu Ala Ala Thr Ile Ala Gln Leu Pro Asp Gln
225                 230                 235                 240

Ile Gly Ala Lys Gly Val Glu Thr Ala Asp Lys Val Leu Lys Gly Glu
                245                 250                 255

Lys Val Gln Ala Lys Tyr Pro Val Asp Leu Lys Leu Val Lys Gln
            260                 265                 270

Asn Gly Gly Ser His His His His His His
            275                 280

<210> SEQ ID NO 13
<211> LENGTH: 282
<212> TYPE: PRT
<213> ORGANISM: Escherichia coli

<400> SEQUENCE: 13

Met Lys Asp Thr Ile Ala Leu Val Val Ser Thr Leu Asn Asn Pro Phe
1               5                   10                  15

Phe Val Ser Leu Lys Asp Gly Ala Gln Lys Glu Ala Asp Lys Leu Gly
                20                  25                  30

Tyr Asn Leu Val Val Leu Asp Ser Gln Asn Asn Pro Ala Lys Glu Leu
            35                  40                  45

Ala Asn Val Gln Asp Leu Thr Val Arg Gly Thr Lys Ile Leu Leu Ile
50                  55                  60

Asn Pro Thr Asp Ser Asp Ala Val Gly Asn Ala Val Lys Met Ala Asn
65                  70                  75                  80

Gln Ala Asn Ile Pro Val Ile Thr Leu Asp Arg Gln Ala Thr Lys Gly
                85                  90                  95

Glu Val Val Ser His Ile Ala Ser Asp Asn Val Leu Gly Gly Lys Ile
            100                 105                 110

Ala Gly Asp Tyr Ile Ala Lys Lys Ala Gly Glu Gly Ala Lys Val Ile
            115                 120                 125

Glu Leu Gln Gly Ile Ala Gly Thr Ser Ala Ala Arg Glu Arg Gly Glu
            130                 135                 140

Gly Phe Gln Gln Ala Val Ala Ala His Lys Phe Asn Val Leu Ala Ser
145                 150                 155                 160

Gln Pro Ala Asp Phe Asp Arg Ile Lys Gly Leu Asn Val Met Gln Asn
                165                 170                 175

Leu Leu Thr Ala His Pro Asp Val Gln Ala Val Phe Cys Gln Asn Asp
            180                 185                 190

Glu Met Ala Leu Gly Ala Leu Arg Ala Leu Gln Thr Ala Gly Lys Ser
            195                 200                 205

Asp Val Met Val Val Gly Phe Asp Gly Thr Pro Asp Gly Glu Lys Ala
            210                 215                 220

Val Asn Asp Gly Lys Leu Ala Ala Thr Ile Ala Gln Leu Pro Asp Gln
225                 230                 235                 240

Ile Gly Ala Lys Gly Val Glu Thr Ala Asp Lys Val Leu Lys Gly Glu
                245                 250                 255

Lys Val Gln Ala Lys Tyr Pro Val Asp Leu Lys Leu Val Lys Gln
            260                 265                 270
```

```
Asn Gly Gly Ser His His His His His His
            275                 280

<210> SEQ ID NO 14
<211> LENGTH: 380
<212> TYPE: PRT
<213> ORGANISM: Escherichia coli

<400> SEQUENCE: 14

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Cys Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Arg
        355                 360                 365
```

Ile Thr Lys Gly Gly Ser His His His His His His
    370             375                 380

<210> SEQ ID NO 15
<211> LENGTH: 380
<212> TYPE: PRT
<213> ORGANISM: Escherichia coli

<400> SEQUENCE: 15

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Cys Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Arg

```
                355                 360                 365
Ile Thr Lys Gly Gly Ser His His His His His His
    370                 375                 380

<210> SEQ ID NO 16
<211> LENGTH: 715
<212> TYPE: DNA
<213> ORGANISM: Staphylococcus aureus

<400> SEQUENCE: 16
cggcgtagag gatcgagatc tcgatcccgc gaaattaata cgactcacta taggggaatt      60
gtgagcggat aacaattccc ctctagaaat aattttgttt aactttaaga aggagatata     120
ccatggcaac ttctactaaa aaattacata agaaccagc  aactttaata aaagcaatcg     180
atggcgatac cgtcaaactg atgtacaaag gccagccgat gacctttaga ctgcttctgg     240 tcgataccc  tgaaaccaaa cacccgaaga aaggcgtgga aaaatacggt ccggaagcat     300
cagcgttcac caagaagatg gtcgaaaacg cgaagaagat cgaggtagaa ttcgacaaag     360
gcaaccgcac ggataaatac ggtcgtggtc tggcatacat ctatgcggac ggcaaaatgg     420
tgaacgaagc actggtacgt caaggtctgg caaaagtcgc atacgtgtac aaaccgaaca     480
acacccacga acagcatctg cgtaaaagcg aagcacaggc gaaaaaggag aagctgaaca     540
tctggagcga agataacgca gatagtggcc aaggaggctc ggactataaa gacgacgacg     600
acaagtaata agagatccgg ctgctaacaa agcccgaaag aagctgagt  tggctgctgc     660 caccgctgag caataactag cataaccct  tggggcctct aaacgggtct gagg           715

<210> SEQ ID NO 17
<211> LENGTH: 1084
<212> TYPE: DNA
<213> ORGANISM: Escherichia coli

<400> SEQUENCE: 17
cggcgtagag gatcgagatc tcgatcccgc gaaattaata cgactcacta taggggaatt      60
gtgagcggat aacaattccc ctctagaaat aattttgttt aactttaaga aggagatata     120
ccatgaaaga ttggattgca ttagtagtaa gtacactcaa taatccatt  ttcgtaagtc     180 ttaaagacgg cgcccaaaaa gaagcggata aactgggcta caaccttgtc gtgctggata     240
gccagaacaa cccggccaaa gaactggcga acgttcagga tctgacagtg cgtggcacca     300
aaattctgct gatcaacccg accgattctg atgcagtagg caacgcggtg aaaatggcga     360
accaggcgaa cattccggtg attaccctgg atagacaggc gaccaaagga gaagtggttt     420
cccatattgc gagcgacaac gttctgggcg gcaaaattgc gggcgactac attgccaaaa     480
aagcgggtga aggcgcgaaa gtgattgaac tgcaggtat  tgccggaacg tcagcagcac     540
gtgaacgtgg tgaaggtttc cagcaggcag tagcggcgca taaattcaac gttctggcct     600
ctcagccagc tgatttcgac cgcattaaag gcctgaacgt tatgcagaac ctgctgacgg     660
cacatccaga tgtacaggcc gtgttcgcgc agaacgatga aatggcatta ggcgcattac     720
gcgcactgca aaccgcaggt aaatccgacg tgatggttgt aggctttgat ggtaccccgg     780
atggtgaaaa agcggttaac gacggcaaac tggcagcaac cattgcccaa cttccggatc     840
agattggtgc gaaaggcgtg gaaaccgcgt acaaagtgct gaaaggcgaa aaagtgcagg     900
cgaaatatcc ggtggatctg aaactggtag tgaaacagaa cggcggctct gattacaaag     960
acgacgacga caaataataa gagatccggc tgctaacaaa gcccgaaagg aagctgagtt    1020
```

-continued

```
ggctgctgcc accgctgagc aataactagc ataaccccctt ggggcctcta aacgggtctt    1080
gagg                                                                  1084

<210> SEQ ID NO 18
<211> LENGTH: 1378
<212> TYPE: DNA
<213> ORGANISM: Escherichia coli

<400> SEQUENCE: 18
cggcgtagag gatcgagatc tcgatcccgc gaaattaata cgactcacta tagggggaatt      60 gtgagcggat aacaattccc ctctagaaat aattttgttt aactttaaga aggagatata     120
ccatgaaaat cgaagaaggc aaactggtta tatggattaa tggtgataaa ggttataacg     180
gtctggcgga agtgggcaaa aaattcgaga aagacaccgg catcaaagtg accgttgaac     240
atccggacaa actggaggag aaattcccac aagttgcagc aacaggcgac ggtcctgata     300
tcatattctg ggcgcatgat cgttttggcg gatacgcaca atcaggctta ctggccgaaa     360
ttaccccgga taaagcgttc caagacaaac tgtacccgtt tacctgggac gctgttcgct     420
ataacgggaa actgatcgcc tacccaattg cagtcgaagc actgtccctg atctacaaca     480
aagatctgct gccgaatccg ccgaaaacat gggaagaaat cccggcgctg gataaagaac     540
tgaaagcgaa aggcaaaagc gcactgatgt tcaaccttca ggaaccgtac ttcacctggc     600
cacttattgc agcagacggc ggttatgcct tcaaatacga aacggcaag tacgacatca     660 aagacgtcgg agtggataac gcaggtgcaa aagcaggtct gaccttcctg gtcgacctca     720
tcaaaaacaa gcacatgaac gccgatacgg attatagcat cgcggaagca gcgtttaaca     780
aaggcgaaac cgcgatgacc attaacggac catgggcctg gagcaacatt gacacctcca     840
aagtgaacta cggcgtaacc gtactgccaa cctttaaagg ccagccgagc aaaccattcg     900
taggcgtact gtcagcaggt attaacgcag caagcccgaa caaagaactg gcgaaggaat     960
tcctggaaaa ctacctgctg accgatgaag gtctggaagc cgtgaacaaa gataaaccgc    1020
tgggcgcagt tgcactgaaa agctacgaag aagaactggc gaaagatccg cgtattgcag    1080
caaccatgga aaacgcgcag aaaggcgaaa tcatgccgaa cattcctcag atgagcgctt    1140
tctggtatgc agttcgcacc gccgttatta acgcagcatc tggtcgtcaa accgtagacg    1200
aagcgctgaa agatgcacag acgcgcatca ccaaaggcgg cagcgattac aaagatgacg    1260
atgacaagta atgagagatc cggctgctaa caaagcccga aggaagctg agttggctgc    1320 tgccaccgct gagcaataac tagcataacc ccttggggcc tctaaacggg tcttgagg      1378
```

PROTEIN ENGINEERING

CROSS-REFERENCE TO RELATED APPLICATIONS

This application is related to and claims the benefit of priority of U.S. Provisional Patent Application Ser. No. 61/264,602 filed Nov. 25, 2009 and U.S. Provisional Patent Application Ser. No. 61/308,553 filed Feb. 26, 2010, which are incorporated herein by reference in their entirety.

STATEMENT OF GOVERNMENT SUPPORT

This invention was made with United States government support from NIH Director's Pioneer Award (5 DPI OD000122-05) and U.S. Dept of Homeland Security (HSHODC-08-C-00099). The United States government has certain rights in this invention.

SEQUENCE LISTING

The sequence listing is provided with the filing of the application in electronic form only, and is incorporated herein by reference. The sequence listing file "028193_9073US02.txt" was generated on Nov. 24, 2010 and is 36,166 bytes in size.

BACKGROUND

Quantitative description of the factors that determine protein expression levels is central to understanding natural systems, design of synthetic systems, and the biotechnology of heterologous gene expression. Protein expression is a complex, multi-step process involving transcription, mRNA stability, translation, post-translational processing, and physical and biological protein stability. Although much of the information controlling expression levels is encoded in the untranslated regions of bacterial genes, sequence variation in the open reading frames (ORFs) also can have profound effects on protein expression levels. Within the context of a constant amino acid sequence considerable nucleic acid sequence variation can be achieved altering four factors: nucleotide composition, levels of RNA secondary structure, codon identity, and the presence of or absence of recognition sequences for stimulatory or inhibitory factors.

Even though considerable experimental and bioinformatic evidence has accumulated for the importance of each of these factors, it has not been possible to distill a unifying quantitative description. Systematic, simultaneous examination of these factors is difficult, because of the challenges in constructing the requisite large number of isocoding sequences. A recent study of the heterologous expression levels in a combinatorial library green fluorescent protein determined that high-frequency codon choice was not the dominant factor, but rather that the degree of secondary structure in the ribosome binding site at the 5' region of the ORF was inversely related to the expression levels. See Kudla et al., Science 324: 255-8 (2009). Even so, this study identified a quantitative link between this factor and protein expression levels for only ~50% of the experimentally observed population.

Biomolecular function is most often the consequence of interactions between molecules (enzymes with substrates, inhibitors, or activators; receptors with ligands; protein-protein networks; protein-DNA; protein-RNA). Such functional interactions affect protein stability by virtue of a thermodynamic linkage relationship between the Gibbs free energy of folding ($\Delta G_{fold}$) and the free energy ligand binding ($\Delta G_{bind}$) to the native (N) or denatured (D) states:

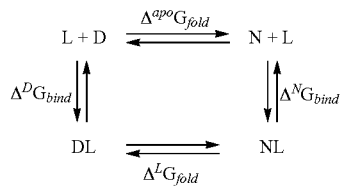

Macromolecular stability is therefore one of the fundamental thermodynamic measures in biochemistry as it can quantitatively report on structure-function relationships and provide a universal monitor for biochemical function.

There are two distinct approaches for determining protein stability. The first measures the free energy of protein folding/unfolding (hereinafter "(un)folding") under equilibrium conditions by assessing the fraction of the native state using spectroscopy, hydrodynamic observations, functional assays, or calorimetry. The second exploits the relationship between protein dynamics and stability by monitoring the differential reactivity of internal chemical groups in native and unfolded states. This approach measures conformational free energies which, under appropriate conditions, correspond to global protein stability. Amide proton exchange is used commonly to monitor such differential reactivity, but its widespread use to assess biological function is often limited by the need for specialized instrumentation and relatively large amounts of protein. Recently, cysteine reactivity has emerged as another means to determine rates of protein (un)folding and estimate protein stabilities. See, e.g., Ha et al., Nat. Struct. Biol. 5: 730-737 (1998); Feng et al., J. Mol. Biol. 314: 153-166 (2001); Sridevi et al., Biochemistry 41: 1568-1578 (2002); Jha et al., J. Biol. Chem. 282: 37479-37491 (2007); and Silverman et al., J. Mol. Biol. 324: 1031-1040 (2002). Nevertheless, existing methods fail to employ the high-sensitivity methods that are required for miniaturization of the assays (e.g. using protein at picomole levels), do not fully develop the theory that establishes at what temperatures the linkage between cysteine reactivity and protein stability is valid, nor do they present how linkage between stability and ligand binding can be established to determine affinities using these methods. Given the state of the art; additional methods for improving and optimizing protein expression and for assessing protein stability such as allowing for use of small quantities (e.g., picomoles) of protein are needed.

SUMMARY

In an aspect, the disclosure provides a method of optimizing an mRNA sequence for protein expression, comprising determining an AU composition of a first percentage in a last portion of a protein coding region of the mRNA sequence; altering the AU composition of the last portion of the protein coding region of the selected mRNA sequence without changing the encoded amino acid sequence, such that the AU composition of the last portion of the coding region in the optimized mRNA sequence is a second percentage.

In an aspect, the disclosure provides a method of optimizing an mRNA sequence for protein expression, comprising determining an AU composition of a first percentage in a last portion of a protein coding region of the mRNA sequence; altering the AU composition of the last portion of the protein coding region of the selected mRNA sequence without changing the encoded amino acid sequence, such that the AU composition of the last portion of the coding region in the optimized mRNA sequence is a second percentage; and optionally further comprising any one or more of:
  altering the AU composition of a first portion of the coding region of the selected mRNA sequence without changing the encoded amino acid sequence, such that the AU composition of the first portion of the coding region of the optimized mRNA sequence is a third percentage;
  altering the AU composition of a middle portion of the selected mRNA sequence, wherein the middle portion is between the first portion and the last portion of the coding region, such that the AU composition of the middle region of the optimized mRNA sequence is a fourth percentage;
  altering the sequence of a first portion of the coding region of the selected mRNA sequence without changing the encoded amino acid sequence, such that the first portion of the coding region of the optimized mRNA sequence is predicted to have less secondary structure relative to the first portion of the coding region of the selected mRNA sequence;
  altering the sequence of a last portion of the coding region of the selected mRNA sequence without changing the encoded amino acid sequence, such that the last portion of the coding region of the optimized mRNA sequence is predicted to have less secondary structure relative to the portion of the coding region of the selected mRNA sequence;
  altering the sequence of a middle portion of the coding region of the selected mRNA sequence without changing the encoded amino acid sequence, such that the middle portion of the coding region of the optimized mRNA sequence is predicted to have less secondary structure relative to the portion of the coding region of the selected mRNA sequence; or
  altering the sequence of the coding region of the selected mRNA sequence such that at least one codon is replaced with a codon that is used at higher frequency in a selected host cell.

In an aspect, the disclosure provides a method of determining the stability of a protein comprising mutating a selected amino acid residue of the protein to a cysteine to form a mutant protein, wherein the selected residue is predicted to be located in a hydrophobic core of the protein; incubating the mutant protein with a thiol-reactive probe under conditions that allow for thiol-reactive probe binding; and detecting a probe-labeled mutant protein.

In an aspect, the disclosure provides a method of determining the affinity of a ligand for a protein comprising mutating a selected amino acid residue of the protein to a cysteine to form a mutant protein, wherein the selected residue is predicted to be located in a hydrophobic core of the protein; incubating the mutant protein with a thiol-reactive probe in the presence of the ligand; and detecting a probe-labeled mutant protein formed in the presence of the ligand.

In an aspect, the disclosure provides a method of determining the affinity of a ligand for a protein comprising mutating a selected amino acid residue of the protein to a cysteine to form a mutant protein, wherein the selected residue is predicted to be located in a hydrophobic core of the protein; incubating the mutant protein with a thiol-reactive probe in the presence of the ligand; detecting a probe-labeled mutant protein formed in the presence of the ligand; and separately, incubating the mutant protein with a thiol-reactive probe in the absence of the ligand; and detecting a probe-labeled mutant protein formed in the absence of the ligand.

In an aspect the disclosure provides a computer readable storage medium comprising a set of instructions that are executable by a microprocessor to perform the function of optimizing an mRNA sequence for protein expression that comprises
  determining an AU composition of a first percentage in a last portion of a protein coding region of the mRNA sequence; and
  altering the AU composition of the last portion of the protein coding region of the selected mRNA sequence without changing the encoded amino acid sequence, such that the AU composition of the last portion of the coding region in the optimized mRNA sequence is a second percentage.

The disclosure provides a number of additional aspects and embodiments that will be apparent to one of skill in the art in light of the following description.

DESCRIPTION OF THE FIGURES

FIG. 1A shows the mean ORF regional nucleotide composition. The regional mean nucleotide composition was calculated for each genome and reported as the ratio of the composition of that region to that of the entire genome. FIG. 1B shows the variances of the mean genomic regional nucleotide compositions. FIG. 1C shows the mean ORF regional secondary structure content. The score is reported as the ratio of a region relative to the entire genome. FIG. 1D shows the variances of the mean ORF regional secondary structure content. FIG. 1E shows the regional CAI. Codon tables were determined for individual genomes and CAI values calculated as a geometric mean of the codon preference scores within each region. FIG. 1F shows the variances of the regional CAI values.

FIG. 2 shows the sequence coverage obtained by LC-MS/MS analysis for *Thermus thermophilus* Aspartate aminostransferase (ttAST; SEQ ID NO:1), *Gallus gallus* Fatty acid binding protein (ggFABP; SEQ ID NO:2) and *Leishmania mexicana* Triose phosphate isomerase (lmTIM; SEQ ID NO:3). Underlined amino acids indicate protein regions for which peptides were sequenced by tandem mass spectrometry. Italicized amino acids denotes amino acids that were modified during sample processing, i.e., carbamidomethylated (Cys) or oxidized (Met). Proteins include N-terminal methionine.

FIG. 5A shows the N-terminal composition, FIG. 5B shows the C-terminal composition, FIG. 5C shows the codon adaptation index, FIG. 5D shows the N-terminal secondary structure content, FIG. 5E shows the middle segment secondary structure content and FIG. 5F shows the C-terminal secondary structure content. Each of the six parameters (two regional nucleotide compositions, three regional secondary structure scores, and the CAI determined over the entire ORF) are represented as a sum of two sigmoidal curves corresponding to penalty and reward thresholds, respectively. The left column shows density plots of the distribution of sigmoids in the ensemble of near-optimal solutions. The false coloring indicates the density of sigmoidal surves passing through a region (magenta, none<blue<green<yellow<red, high density). The middle column shows the sigmoids of the parameter set that best fits the data. The score of each component ranges [−200,200]; their sum is mapped onto the protein expression category as <−100→0 (no expression), [−100,0]→1 (poor), [0,100]→2 (mediocre), >100→3 (good). The right column shows the distribution of parameters in the experimental dataset.

FIG. 8A shows the SDS-PAGE of time dependent modification of ecRBP variant L62C (SEQ ID NO:12) with 1 mM IAM-biotin (left panel); unlabeled fractions were quantified by densitometry and fit with a single exponential to obtain reaction rates (right panel) at different temperatures. FIG. 8B shows the labeling of SN variant L36C (SEQ ID NO:11) with IAM-biotin (left panel); the (un)labeled forms migrated differently in the gel, enabling ratiometric quantification to obtain reaction rates (right panel) at different temperatures.

FIG. 10A shows the progress curves for the reaction of 80 µM IAM-biotin with 800 µM reduced L-glutathione (GSH) at different temperatures in 25 mM MOPS, 100 mM KCl and pH 7.6. Pseudo-first order rate constants ($k_{int}$) derived from these data: $6.2 \times 10^{-4}$ (25° C.), $1.6 \times 10^{-4}$ (35° C.), $3.5 \times 10^{-3}$ (45° C.), and $7.7 \times 10^{-3}$ (55° C.) s$^{-1}$; second order rate constants (i.e. k=$k_{int}$/[GSH]) of $7.8 \times 10^{-1}$, 2.0, 4.4 and 9.6 M$^{-1}$s$^{-1}$ respectively. FIG. 10B shows the Arrhenius plot of the second order rate constants for the bimolecular reaction of IAM-biotin and GSH. FIG. 10C shows the representative QCR curves at 50° C. for unfolded SN variants L36C (purple; $k_{int}$=$3 \times 10^{-3}$ s$^{-1}$) and F34C (black; $k_{int}$=$2 \times 10^{-3}$ s$^{-1}$) at 438 µM IAM-biotin, ~0.1 µM protien, 25 mM MOPS, 100 mM KCl and pH 7.6.

FIG. 11A shows the cysteine substitution sites in the hydrophobic core of SN (pdb code 1SNC), FIG. 11B shows the hydrophobic core of ecRBP (pdb code 2DRI) and FIG. 11C shows the hydrophobic core of *E. coli* maltose-binding protein (ecMBP; pdb code 1ANF).

(FIG. 14A), and for ecMBP variants T157C (SEQ ID NO:14) (black) and S263C (SEQ ID NO:15) (purple) at 63.3° C. (FIG. 14B). The solid lines represent the fit of Equation 20 to the data to obtain $K_D$ values. Error bars correspond to the propagated uncertainty of two combined $\Delta G_U$ measurements.

FIG. 15A shows the QCR experiments for SN variant L36C in the absence (black) and presence of 1 mM Ca2+ (purple) or 50 µM pdTp (orange). FIG. 15B shows the dependence of $\Delta\Delta G_U$ on a 2:1 molar ratio of Ca$^{2+}$ and pdTp for SN variants F34C (black) and L36C (purple) fit with Equation 20 to obtain $K_D$ values. FIG. 15C shows the QCR experiments for SN variant L36C.

DETAILED DESCRIPTION

Figure 1:
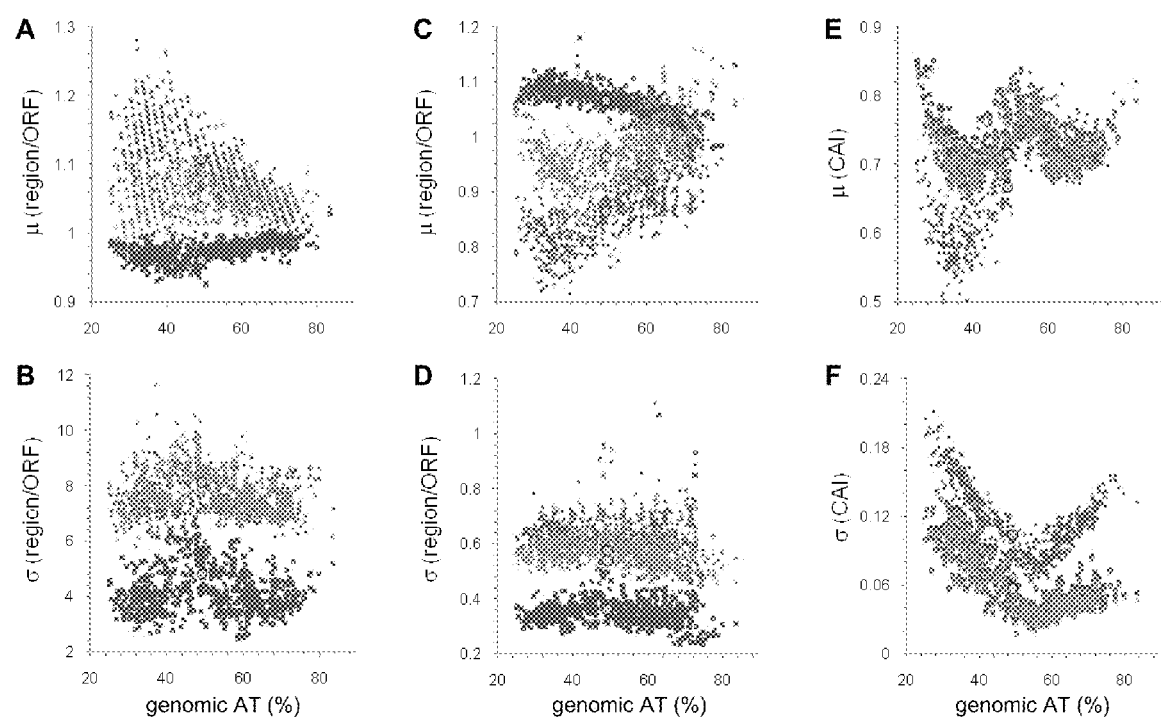
FIGS. 1A-F show regional variation of nucleotide composition, RNA secondary structure, and codon adaptation index (CAI) within the open reading frames of 816 fully sequenced bacterial genomes. Blue, N-terminal region (first 35 bases); red, middle region; green, C-terminal region (last 35 bases). Circles indicate the values of these parameters for *E. coli* strain K-12 DH10B.

Before any embodiments are described in detail, it is to be understood that the claims are not limited to the details of construction and the arrangement of components set forth in the following description or illustrated in the included drawings. Unless stated otherwise, all patent and non-patent references and citations are incorporated by reference herein.

Optimization of mRNA for Protein Expression

In a general sense, the disclosure relates to methods that are useful in the characterization of various biological structure/function relationships. For example, the disclosure provides a method for optimizing an mRNA sequence for protein expression using a systematic analysis based on regional characteristics and properties of isocoding nucleotide sequences. As described herein, the inventors have identified regional variation in nucleotide composition, RNA secondary structure, and codon usage biases in prokaryotic genomes. In all those genomes, the first and last portions in the ORFs were significantly richer in AU content and lower in secondary structure content than the middle segment. Codon choices in the N-terminal encoding region also differ significantly from the rest of the ORF. Furthermore, a complex interrelationship may exist between codon choice, genomic nucleotide composition, and proteomic amino acid composition. Simulation of random drift in these genomes by stochastically varying isocodon choice suggests that these features are maintained by positive selection of genomic nucleotide composition. Further, the method can be used for the design of synthetic genes with optimal protein expression levels for any variety of organism, particularly prokaryotic organisms.

As another example, the disclosure relates to a method of determining protein stability and/or ligand binding affinity that provides an approach that includes introducing one or more mutations to a targeted region of a protein. The inventors have found that methods incorporating quantitative cysteine reactivity can be used to measure the macromolecular stability of a protein, or a protein-ligand complex, using very small amounts of protein material. These methods allow for miniaturized assays, including the miniaturization of existing assays, for determining protein stability in either the absence or presence of a ligand.

The inventors have developed a computational algorithm (ORFOPT) that enables the construction of synthetic genes and optimized mRNAs in which regional AU composition, mRNA secondary structure, and codon choice are varied systematically. The inventors have identified that previously unidentified structural considerations can contribute in a significant way to protein expression, and be used to determine protein expression levels. The algorithm includes a nonlinear scoring function that relates experimental protein expression levels to the synthetic mRNA sequences. Using the algorithm, certain features in ORFs can be used to determine protein expression levels, and can enable prediction of expression levels of naturally occuring ORFs.

Thus, in an aspect, the disclosure provides a method of optimizing an mRNA sequence for protein expression. While a number of environmental factors can affect protein expression levels the method for optimizing described herein encompasses embodiments that relate to nucleotide sequence and structure (e.g., primary and secondary structure). Accordingly, some embodiments include analysis and potential modification of factors including, for example, AU (or AT) content in the nucleotide sequence encoding a region that encompasses the N- and/or C-termini, degree of secondary structure in the nucleotide sequence encoding a region that encompasses the N- and/or C-termini, degree of secondary structure in the nucleotide sequence in a region that is between the portions encoding the N- and/or C-termini, and high-frequency codon usage.

In embodiments, the disclosure provides a method of optimizing an mRNA sequence for protein expression, comprising determining an AU composition of a first percentage in a last portion of a protein coding region of the mRNA sequence; and altering the AU composition of the last portion of the protein coding region of the selected mRNA sequence without changing the encoded amino acid sequence, such that the AU composition of the last portion of the coding region in the optimized mRNA sequence is a second percentage.

In some embodiments, the disclosure provides a method for analyzing an existing mRNA sequence (for example, a naturally occurring mRNA sequence or a synthetic mRNA sequence) to determine the expected protein expression level. Such embodiments comprise determining an AU composition of a first percentage in a last portion of a protein coding region of the mRNA sequence and, based on the first percentage relative to an optimized percentage, predict the protein expression level. Further embodiments of this method include optimizing the mRNA sequence that has been analyzed, and comprise altering the AU composition of the last portion of the protein coding region of the selected mRNA sequence without changing the encoded amino acid sequence, such that the AU composition of the last portion of the coding region in the optimized mRNA sequence is a second percentage, wherein the second percentage is predicted to increase protein expression level relative to the first percentage.

In any of the above embodiments, the method can comprises determining one or more of the following mRNA characteristics of a selected mRNA sequence: AU composition of the N-terminal coding region of the mRNA sequence; the secondary structure of the N-terminal and/or C-terminal coding region(s) of the mRNA sequence; the secondary structure and/or AU composition of the mRNA middle segment secondary structure; or codon usage bias. Thus, some embodiments provide a method comprising determining an AU composition of a first percentage in a last portion of a protein coding region of the mRNA sequence; and altering the AU composition of the last portion of the protein coding region of the selected mRNA sequence without changing the encoded amino acid sequence, such that the AU composition of the last portion of the coding region in the optimized mRNA sequence is a second percentage; and further comprising at least one of (a) altering the AU composition of a first portion of the coding region of the selected mRNA sequence without changing the encoded amino acid sequence, such that the AU composition of the first portion of the coding region of the optimized mRNA sequence is a third percentage;

(b) altering the AU composition of a middle portion of the selected mRNA sequence, wherein the middle portion is between the first portion and the last portion of the coding region, such that the AU composition of the middle region of the optimized mRNA sequence is a fourth percentage;

(c) altering the sequence of a first portion of the coding region of the selected mRNA sequence without changing the encoded amino acid sequence, such that the first portion of the coding region of the optimized mRNA sequence is predicted to have less secondary structure relative to the first portion of the coding region of the selected mRNA sequence;

(d) altering the sequence of a last portion of the coding region of the selected mRNA sequence without changing the encoded amino acid sequence, such that the last portion of the coding region of the optimized mRNA sequence is predicted to have less secondary structure relative to the portion of the coding region of the selected mRNA sequence;

(e) altering the sequence of a middle portion of the coding region of the selected mRNA sequence without changing the encoded amino acid sequence, such that the middle portion of the coding region of the optimized mRNA sequence is predicted to have less secondary structure relative to the portion of the coding region of the selected mRNA sequence; or (f) altering the sequence of the coding region of the selected mRNA sequence such that at least one codon is replaced with a codon that is used at higher frequency in a selected host cell.

Certain embodiments provide for any combination of the above-mentioned altering processes, such that the method can include one, two, three, four, or five additional alterations to the mRNA sequence. Accordingly, embodiments provide for a combination of alterations to the mRNA sequence that can include changes to the AU composition in the first (N-terminal) and last (C-terminal) coding regions or optionally the entirety of the mRNA sequence; changes to the AU composition and changes that decrease secondary structure in one or more regions (e.g., first, last, or middle portions); changes to the AU composition and changes from a native codon to a higher frequency codon; or changes that decrease secondary structure in one or more regions and changes from a native codon to a higher frequency codon; and the like.

In certain embodiments of this aspect, the method further comprises optimizing at least one of characteristics (a) and (b) to produce an optimized mRNA sequence; or the method further comprises optimizing at least one of characteristics (a) through (c) to produce an optimized mRNA sequence; or the method further comprises optimizing at least one of characteristics (a) through (d) to produce an optimized rnRNA sequence; or the method further comprises optimizing at least one of characteristics (a) through (e) to produce an optimized mRNA sequence; or the method further comprises optimizing at least one of characteristics (a) through (f) to produce an optimized mRNA sequence. Any combination or permutation of characteristics (a) through (f) can be employed in various embodiments of the methods described herein.

In certain embodiments, the method further comprises optimizing characteristic (a) of a selected mRNA sequence to produce an optimized mRNA sequence. In embodiments, the method comprises determining at least characteristic (a) of a selected mRNA sequence. Some embodiments provide a method that comprises determining at least characteristics (a) and (b) of a selected mRNA sequence. In embodiments, the method comprises determining at least characteristics (a) through (c) of a selected mRNA sequence. In certain embodiments, the method comprises determining at least characteristics (a) through (d) of a selected mRNA sequence. In certain embodiments, the method comprises determining at least characteristics (a) through (e) of a selected mRNA sequence. Some embodiments provide a method comprising determining at least characteristics (a) through (f) of a selected mRNA sequence.

Any mRNA sequence that encodes a desired amino acid sequence (e.g., protein, polypeptide, functional fragments thereof, etc.) can be used in the methods described herein. In some embodiments, the mRNA is selected for optimization and expression in a host cell, such as a recombinant cell or a native cell. Embodiments provide for mRNA sequence selection based on an analysis using any of the methods described herein, wherein the method predicts that the mRNA will express less protein than desired for a particular purpose (e.g., cell based assays, protein overexpression, etc.). In some embodiments the mRNA is selected for protein overexpression in a prokaryotic cell and subsequent purification.

As used herein, "altering" a selected mRNA sequence comprises changing one or more nucleotides in the mRNA molecule such as, for example, a nucleotide in the coding region to another nucleotide by any suitable technique. In certain embodiments, a native nucleotide is changed to a naturally occurring nucleotide such as, for example, one of the three other common nucleotides in DNA or RNA (thymine, uracil, cytosine, guanine, adenine). As a non-limiting example, an adenine (A) may be changed to a guanine (G), cytosine (C), thymine or uracil (T or U), depending on RNA/DNA. Similarly; a T/U may be changed to an A, G, or C; a G may be changed to an A, C, or T/U; and/or a C may be changed to an A, U, or G. Such alteration may be made to a DNA sequence that encodes a selected mRNA sequence or to the mRNA molecule itself. Further, such alteration may be made by any method known in the art. Methods can include, but are not limited to, any method of site-directed mutagenesis (Branigan & Wilkinson, *Nat. Rev. Cell. Biol.* 3:964-70 (2002)) and synthetic gene and genome assembly (Mueller et al., *Chem. Biol.* 16:337-47 (2009). Certain non-limiting methods of altering nucleic acid sequences are described, e.g., in Cox et al., *Protein Science* 16:379-390 (2007).

As used in some embodiments herein, an mRNA sequence is "predicted" when a method of calculating improved protein expression is used to generate it. In some embodiments, the method of calculating improved protein expression can include any one or combination of elements discussed herein and can optionally be an automated method such as, for example, a method comprising an algorithm or computer program (e.g., the ORFOPT prograrh). In some embodiments the protein expression level can be "predicted" based on mRNA sequence, either naturally-occurring or synthetic mRNA, using any of the methods described herein.

As used herein, "optimizing" means changing a characteristic of a selected mRNA sequence such that the changed, or optimized, mRNA sequence is predicted to express at a higher level in a selected host cell than the original, selected mRNA sequence. Optimizing does not require that the characteristic be changed such that the optimized mRNA sequence is predicted to express at the highest possible level in a selected host cell. Rather, a characteristic is considered to be optimized when the optimized mRNA sequence is predicted to express at a higher level than the original, selected mRNA sequence.

Similarly, an "optimized mRNA sequence" is predicted to express at a higher level in a selected host cell than the original mRNA sequence upon which the optimized mRNA sequence is based. An optimized mRNA sequence need not be predicted to express at the highest possible level in the selected host cell.

As used herein, "secondary structure" is the general three-dimensional form of local segments of biopolymers such as proteins and nucleic acids (DNA/RNA). Secondary structure is defined by the hydrogen bonds of the biopolymer, as observed in an atomic-resolution structure. In nucleic acids, the secondary structure is defined by the hydrogen bonding between the nitrogenous bases. The secondary structure of a nucleic acid molecule refers to the basepairing interactions within a single molecule or set of interacting molecules. The secondary structure of biological RNAs can be uniquely decomposed into stems and loops. Frequently these elements, or combinations thereof, can be further classified, for example, tetraloops, pseudoknots and stem-loops.

As used herein, "less secondary structure" or "reduced secondary structure" means that the optimized mRNA sequence is predicted to have less secondary structure than the selected mRNA sequence. In certain embodiments, reducing secondary structure comprises altering the mRNA sequence to reduce base-pairing between different portions of the mRNA sequence. The presence of secondary structure can be determined, in certain embodiments, by any suitable RNA folding programs known in the art. See, e.g., Zuker and Stiegler, *Nucleic Acids Res.*, 9:133-148 (1981). Accordingly, in various embodiments the amount of secondary structure can be calculated based on any number of factors that are known to influence hydrogen bonding interactions including, for example, the number, length, or frequency pattern of inverted repeat motifs in the sequence. In some embodiments, the secondary structure can be determined based on an inverted repeat score, which can optionally be an automated calculation that comprises an algorithm or computer program such as, for example, the O$_{RF}$O$_{PT}$ program.

As used herein, "hydrophobic core" refers to a structure of an amino acid sequence (e.g., a protein) in which the side chains of hydrophobic amino acids are buried from water. In some embodiments, the hydrophobic core refers to a hydrophobic region of an amino acid sequence, such as a protein, wherein the region can be an area of local hydrophobicity near the protein surface. In some embodiments, the hydrophobic core refers to the interior region of a protein.

In certain embodiments, the protein product of an optimized mRNA sequence is expressed at higher levels than the protein product of the non-optimized (e.g., native) mRNA sequence in the same host cell, or native cell or either. Expression of the protein product of an optimized mRNA sequence at "higher levels" than the non-optimized mRNA sequence includes any measurable increase in the amount of protein product. In some embodiments the optimized mRNA sequence is expressed at a level that is at least 1.01-fold, 1.05-fold, 1.1-fold, 1.2-fold, 1.3-fold, 1.4-fold, 1.5-fold, 1.6-fold, 1.7-fold, 1.8-fold, 1.9-fold, 2-fold, 3-fold, 5-fold, or at least 10-fold greater than the protein product of a selected mRNA sequence. In some embodiments, when the protein product of a selected mRNA is not detectably expressed in a host cell, the protein product of an optimized mRNA is expressed at detectable levels.

Certain exemplary host cells include, but are not limited to, prokaryotes, including eubacteria, e.g., *E. coli,* and archeabacteria.

mRNA N-Terminal AU Composition

Certain embodiments provide methods of optimizing a selected mRNA sequence comprising altering the selected mRNA sequence such that the AU composition in a first portion of the coding region is a chosen percentage (such as, for example, 30%). Suitably, the selected mRNA sequence is altered without changing the encoded amino acid sequence. In certain embodiments, the selected mRNA sequence is altered such that one or more amino acids are changed in the encoded amino acid sequence. In some embodiments, the changes in amino acids that are introduced by the altered mRNA have no substantial effect on protein function. In various embodiments, the first portion ranges between about the first 30 to about the first 100 nucleotides, (e.g., the first 30 bases, the first 35 bases, the first 40 bases, the first 45 bases, the first 50 bases, the first 60 bases, or the first 75 bases, etc.). As used herein, "the first 45 bases of a coding region," for example, are counted starting with the first nucleotide of the first codon of the coding region of the mRNA sequence. Typically, the first codon is "ATG," in which case the first nucleotide is "A" such that the first 45 bases includes the "A" plus the next 44 bases, or nucleotides, of the coding region of the mRNA sequence.

mRNA C-Terminal AU Composition

In certain embodiments, methods of optimizing a selected mRNA sequence comprising altering the selected mRNA sequence such that the AU composition in the last 30 to 75 bases of the coding region is a chosen percentage (such as, for example, 30%) are provided. In certain embodiments, the selected mRNA sequence is altered without changing the encoded amino acid sequence. In certain embodiments, the last portion ranges between about the last 30 to the last 75 nucleotides, (e.g., the last 30 bases, the last 35 bases, the last 40 bases, the last 45 bases, the last 50 bases, the last 60 bases, or the last 75 bases, etc.). As used herein, "the last 45 bases of a coding region," for example, are counted starting with the last nucleotide of the stop codon of the coding region of the mRNA sequence. The last 45 bases are therefore the stop codon plus the previous 42 bases, or nucleotides, of the coding region of the mRNA sequence. Stop codons are known in the art and can be determined by one of skill based on the reading frame of the mRNA. In some embodiments, the stop codon can be TAG, TAA, or TGA.

mRNA Middle AU Composition

In certain embodiments, methods of optimizing a selected mRNA sequence comprising altering the selected mRNA sequence such that the AU composition in the middle of the coding region is a chosen percentage are provided. In certain embodiments, the middle of the coding region is the region between the first 30-75 bases and the last 30-75 bases. In various embodiments, the middle of the coding region is the region between the first 75 bases and the last 75 bases, the region between the first 60 bases and the last 60 bases, the region between the first 50 bases and the last 50 bases, the region between the first 45 bases and the last 45 bases, the region between the first 40 bases and the last 40 bases, the region between the first 35 bases and the last 35 bases, or the region between the first 30 bases and the last 30 bases. In certain embodiments, the selected mRNA sequence is altered without changing the encoded amino acid sequence. In certain embodiments, the selected mRNA sequence is altered such that one or more amino acids are changed in the encoded amino acid sequence.

mRNA N-Terminal Secondary Structure

In certain embodiments, methods of optimizing a selected mRNA sequence comprising altering the sequence of a first portion of the coding region of the selected mRNA sequence, such that the first portion of the coding region of the optimized mRNA sequence is predicted to have reduced secondary structure. In certain embodiments, the selected mRNA sequence is altered without changing the encoded amino acid sequence. In certain embodiments, the selected mRNA sequence is altered such that one or more amino acids in the encoded amino acid sequence are changed. In various embodiments, the first portion is the first 20 bases, the first 35 bases, the first 50 bases, the first 75 bases, the first 100 bases, or the first 200 bases.

mRNA C-Terminal Secondary Structure

In certain embodiments, methods of optimizing a selected mRNA sequence comprising altering the sequence of a last portion of the coding region of the selected mRNA sequence, such that the last portion of the coding region of the optimized mRNA sequence is predicted to have less secondary structure. In certain embodiments, the selected mRNA sequence is altered without changing the encoded amino acid sequence. In certain embodiments, the selected mRNA sequence is altered such that one or more amino acids in the encoded amino acid sequence are changed. In various embodiments, the last portion is the last 20 bases, the last 35 bases, the last 50 bases, the last 75 bases, the last 100 bases, or the last 200 bases.

mRNA Middle Secondary Structure

In certain embodiments, methods of optimizing a selected mRNA sequence comprising altering the sequence of a middle portion of the coding region of the selected mRNA sequence, such that the middle portion of the coding region of the optimized mRNA sequence is predicted to have less secondary structure. In certain embodiments, selected mRNA sequence is altered without changing the encoded amino acid sequence. In certain embodiments, the selected mRNA sequence is altered such that one or more amino acids in the encoded amino acid sequence are changed. In various embodiments, the middle portion of the coding region is the region between the first 75 bases and the last 75 bases, the region between the first 60 bases and the last 60 bases, the region between the first 50 bases and the last 50 bases, the region between the first 45 bases and the last 45 bases, the region between the first 40 bases and the last 40 bases, the region between the first 35 bases and the last 35 bases, or the region between the first 30 bases and the last 30 bases.

Codon Usage Bias

In certain embodiments, methods of optimizing a selected mRNA sequence comprising altering the sequence of the coding region of the selected mRNA sequence such that at least one codon is replaced with a codon that is used at higher frequency in a selected host cell are provided. In certain embodiments, when an amino acid is encoded by at least two codons, the codons are ranked according to their usage in the selected host cell. Preferred codons for organisms including mammals (e.g., humans) and plants are known to the art (e.g., Wada et al., *Nucl. Acids Res.*, 18:2367 (1990); Murray et al., *Nucl. Acids Res.*, 17:477 (1989)).

As an illustrative example, if a selected host cell uses the codon CGU for arginine 20% of the time, the codon CGC for arginine 27% of the time, the codon CGA for arginine 35% of the time, and the codon CGG for arginine 18% of the time, the codons are ranked CGA>CGC>CGU>CGG. In certain embodiments, then, a selected mRNA may be optimized, for example, by changing a CGG codon to a CGC, CGU or CGA codon, by changing a CGU codon to a CGC or CGA codon, etc. That is, in certain embodiments, a selected mRNA may be optimized by changing at least one codon to a codon that is ranked higher for the selected host cell. The codon need not be changed to the highest ranked codon for the selected host cell.

In an aspect the disclosure provides a computer readable storage medium comprising a set of instructions that are executable by a microprocessor to perform the function of optimizing an mRNA sequence for protein expression that comprises determining an AU composition of a first percentage in a last portion of a protein coding region of the mRNA sequence; and altering the AU composition of the last portion of the protein coding region of the selected mRNA sequence without changing the encoded amino acid sequence, such that the AU composition of the last portion of the coding region in the optimized mRNA sequence is a second percentage.

Further embodiments of this aspect provide for a set of instructions on a computer readable storage medium that further include at least one of:

altering the AU composition of a first portion of the coding region of the selected mRNA sequence without changing the encoded amino acid sequence, such that the AU composition of the first portion of the coding region of the optimized mRNA sequence is a third percentage;

altering the AU composition of a middle portion of the selected mRNA sequence, wherein the middle portion is between the first portion and the last portion of the coding region, such that the AU composition of the middle region of the optimized mRNA sequence is a fourth percentage;

altering the sequence of a first portion of the coding region of the selected mRNA sequence without changing the encoded amino acid sequence, such that the first portion of the coding region of the optimized mRNA sequence is predicted to have less secondary structure relative to the first portion of the coding region of the selected mRNA sequence;

altering the sequence of a last portion of the coding region of the selected mRNA sequence without changing the encoded amino acid sequence, such that the last portion of the coding region of the optimized mRNA sequence is predicted to have less secondary structure relative to the portion of the coding region of the selected mRNA sequence;

altering the sequence of a middle portion of the coding region of the selected mRNA sequence without changing the encoded amino acid sequence, such that the middle portion of the coding region of the optimized mRNA sequence is predicted to have less secondary structure relative to the portion of the coding region of the selected mRNA sequence; or altering the sequence of the coding region of the selected mRNA sequence such that at least one codon is replaced with a codon that is used at higher frequency in a selected host cell.

Thus, in some embodiments, certain portions of the method are implemented on a computer system. Suitable computer systems are well known in the art and may include, in certain embodiments, an input device, an output device, a storage medium, and/or a processor. Certain exemplary input devices include, but are not limited to, a keyboard, a computer mouse, a touch screen, and the like. Certain exemplary output devices include, but are not limited to, a cathode-ray tube (CRT) computer monitor, a liquid-crystal display (LCD) computer monitor, and the like. Certain exemplary storage media include, but are not limited to, various types of memory such as a hard disk, RAM, flash memory, and other magnetic, optical, physical, or electronic memory devices. A processor may be any typical computer processor for performing calculations and directing other functions for performing input, output, calculation, and display of data in the disclosed calculator. The storage media may comprise a set of instructions and/or data stored thereon that can be executed or otherwise manipulated by a micro processor. Such data may include, but is not limited to, image data and numerical data.

In certain embodiments, certain portions of the method are implemented on a web page. In certain embodiments, certain portions of the method are implemented as a locally-controlled program on a personal computer. In certain embodiments, certain portions of the method may be implemented on a personal digital assistant (PDA), cell phone, or other hand-held electronic device.

Embodiments provide that portions of the methods that may be implemented on a computer and/or web page include, but are not limited to, (a) determining the AU composition of a last portion of a selected mRNA sequence; (b) optimizing the selected mRNA sequence such that the AU composition in the last portion is a chosen percentage, either without changing the encoded amino acid sequence, or including certain changes in the encoded amino acid sequence; (c) determining the AU composition of a first portion of a selected mRNA sequence; (d) optimizing the selected mRNA sequence such that the AU composition in the first portion is a chosen percentage, either without changing the encoded amino acid sequence, or including certain changes in the encoded amino acid sequence; (e) determining the secondary structure of a first portion of a selected mRNA sequence; (f) optimizing the first portion of the selected mRNA sequence to reduce the amount of secondary structure, either without changing the encoded amino acid sequence, or including certain changes in the encoded amino acid sequence; (g) determining the secondary structure of a last portion of a selected mRNA sequence; (h) optimizing the last portion of the selected mRNA sequence to reduce the amount of secondary structure, either without changing the encoded amino acid sequence, or including certain changes in the encoded amino acid sequence; (i) determining the codon usage of a selected host cell; and (j) optimizing the codon usage of a selected mRNA sequence.

Picomole-Scale Characterization of Protein Stability and Function

In another broad sense the disclosure relates to a method, called quantitative cysteine reactivity (QCR), in which protein stability is determined by monitoring the reactivity of cysteine residues buried in the hydrophobic core of proteins. This approach has the advantage over more traditional methods for measuring protein stability in that it uses only picomoles (nanograms) of protein, uses simple instrumentation accessible to any lab, is higher throughput, and can provide site-specific thermodynamic information. QCR can be used to determine apparent protein stabilities rapidly and accurately, construct Gibbs-Helmholtz stability profiles, measure ligand binding over a large range of ligand concentrations and affinities, and infer enzymatic activity, in certain embodiments, without the need for developing a kinetic assay.

Thus, in an aspect the disclosure provides a method of determining stability of a protein comprising mutating a selected amino acid residue of the protein to a cysteine to form a mutant protein, wherein the selected residue is predicted to be located in a hydrophobic core of the protein; incubating the mutant protein with a thiol-reactive probe under conditions that allow for thiol-reactive probe binding; and detecting a probe-labeled mutant protein. In certain embodiments, QCR can be used to determine protein stability using picomole quantities of material (nanograms for an average-sized protein), gel electrophoresis equipment, and gel analysis software. Furthermore, QCR assesses stability at low protein concentrations, which, in certain embodiments, minimizes aggregation, which can be a problem in stability measurements made by less sensitive methods. QCR exploits the fundamental relationship between protein flexibility and stability by monitoring the differential reactivity of internal chemical groups in the native and unfolded state. Unlike certain previous methods, such as hydrogen exchange (HX), QCR observations can be obtained within the global unfolding window of observation (GUWO; ~10-15° C. of $T_m$), where, in certain embodiments, global unfolding events dominate and the reported energetics corresponds to global unfolding free energies.

QCR can be used to investigate many aspects of biological function that are linked to protein stability. For instance, in certain embodiments, protein-ligand interactions can be identified and quantified through the fundamental thermodynamic linkage relationships between ligand binding and protein stability. This analysis can be used, in certain embodiments, to infer enzymatic activity by monitoring changes in stability in the presence of substrate, product (produced in the course of the reaction), and/or inhibitors. The ability to obtain thermodynamic measurements with small amounts of material and available instrumentation enables application and adaptation of the QCR technique for protein characterization, including protein engineering experiments and functional genomic studies that use the thermodynamic characterization of a large number of variants.

In embodiments, methods of determining the stability of a protein are provided that comprise, mutating a selected amino acid residue of the protein to a cysteine to form a mutant protein, wherein the selected residue is predicted to be located in a hydrophobic core of the protein; incubating the mutant protein with a thiol-reactive probe in the presence of the ligand; and detecting a probe-labeled mutant protein formed in the presence of the ligand.

In certain embodiments, methods of measuring the affinity of a ligand for a target protein are provided. Such methods comprise, in certain embodiments, (a) mutating a selected residue of a target protein to a cysteine, wherein the selected residue is predicted to be located in the hydrophobic core of the target protein; (b) incubating the mutant target protein with a thiol-reactive probe in the presence and absence of the ligand; and (c) detecting a probe-labeled mutant target protein.

"Mutating" a selected residue of a target protein to a cysteine, as used herein, means changing a non-cysteine residue in the target protein to a cysteine. In certain embodiments, changing the non-cysteine residue to a cysteine comprises altering the mRNA sequence that encodes the target protein to change a selected codon that does not encode a cysteine to a codon that does encode a cysteine. Such altering may be carried out by any method known in the art, including the methods discussed herein. In certain embodiments, a DNA sequence that encodes the mRNA is mutated to alter the selected codon in the mRNA sequence.

A selected residue is predicted to be in the hydrophobic core of the target protein when static solvent-accessible surface area for the entire sidechain is less than ~10%, as calculated from the structure coordinates.

A "thiol-reactive probe," as used herein, is a detectable moiety capable of reacting with a thiol (i.e., —SH) group and forming a bond between the thiol-reactive probe and the thiol group. The bond can be covalent or non-covalent, and is suitably stable under the selected detecting conditions. A "detectable moiety" includes any moiety that is detectable as is, or which can be rendered detectable by subsequent reaction (i.e., modification or conjugation). Certain exemplary detectable moieties include, but are not limited to, dyes (e.g., visible dyes), labels (e.g., fluorescent labels), and particles (e.g., phosphorescent labels). Exemplary detectable moieties also include, but are not limited to, members of binding pairs, such as biotin, avidin, streptavidin, antigens, antibodies and antibody fragments, nucleic acids, nucleic acid binding proteins, single-stranded nucleic acids and their complements One skilled in the art can modify a selected detectable moiety to make it thiol-reactive, if needed. Various reagents and methods of modifying detectable moieties to be thiol reactive are commercially available, e.g., from Thermo Scientific.

Methods of detecting a probe-labeled mutant protein include any methods in the art, such as separation of labeled and unlabeled mutant protein by SDS-PAGE and detection of the separated proteins.

In certain embodiments, a probe-labeled mutant target protein is detected at two or more time points. In certain embodiments, a probe-labeled mutant target protein is detected at three or more, four or more, five or more, six or more, seven or more, eight or more, nine or more, ten or more, fifteen or more, or twenty or more time points.

In certain embodiments, a method further comprises determining the rate at which probe-labeled mutant target protein is formed. One skilled in the art can determine the rate using methods in the art, including, for example, the methods described in the Examples below.

In certain embodiments, a method further comprises determining the affinity of a ligand for a protein. In certain such embodiments, the rate at which probe-labeled mutant target protein is formed is determined in the presence and absence of the ligand. One skilled in the art can determine the rate using methods in the art, including, for example, the methods described in the Examples below. Further, one skilled in the art can determine the affinity of the ligand for the protein using methods known in the art, including, for example, the methods described in the Examples below.

The Examples below are merely illustrative of certain aspects and embodiments of the disclosure and do not limit the scope of the claims.

EXAMPLES

Example 1

Optimization of Protein Expression in Prokaryotes

Definitions of Bioinformatic Measurements:
Regional nucleotide composition (v) was defined as $$v = \frac{N_{AT}}{L} \quad (1)$$

where $N_{AT}$ was the number of AT bases in a region length L.

RNA secondary structure was represented by a scoring function that captures the degree of inverted repeats in a region, weighted by the base-pairing character, and loop or bulge sizes. This score was calculated by centering a recursive search of maximally-sized inverted repeats within a maximum distance from a given nucleotide; duplexes were allowed to contain bulges or gaps. The score for such a maximally-sized inverted repeat was determined using previously published stem-loop base-pairing energies [Freier, S. M., et al., (1986) "Improved free-energy parameters for predictions of RNA duplex stability." *Proc Natl Acad. Sci. USA*, 83:9373-9377; Jaeger, J. A., et al., (1989) "Improved predictions of secondary structures for RNA." *Proc. Natl Acad. Sci. USA*, 86:7706-7710], and assigned to each nucleotide encompassed within the calculated stem-loop. The regional secondary structure score $S_r$ in a region was expressed as:

$$S_r = \sum_{begin}^{end} S_i \quad (2)$$

where $S_i$ was the summed energy assigned to an individual base for participating in stem-loops (0 if not part of any secondary structure).

This algorithm was developed because it enables efficient updating of secondary structure scores by limiting the calculation to regions having sequence that has been changed in a simulated annealing optimization calculation (see below). It does not attempt to calculate free energies of RNA folding; rather, it provides a measure of the density of inverted repeats in a region which in turn determines propensity for secondary structure formation in that region.

Genomic codon tables were calculated as the frequency distribution of $$f_i = \frac{n_i}{N} \quad (3)$$

where $f_i$ was the frequency of each individual codon (i=[1, . . . ,64 ]), $n_i$ was the total count of codon i, and N the total number of codons in the genome. The normalized codon frequency for amino acid a was $$^a f_i = \frac{^a n_i}{\sum_{i=1}^{N_a} {}^a n_i} \quad (4)$$

where $^a n_i$ was the count of codon i for a, and $N_a$ was the number of degenerate codons for a. The codon adaptation index (CAI) for the $i^{th}$ codon in the $a^{th}$ amino acid was defined as $$^a c_i = \frac{^a f_i}{^a f_{max}} \quad (5)$$

where $^a f_{max}$ was the highest normalized codon frequency in a. The CAI for a region L was the geometric mean $$C_L = \sqrt[L]{\prod_{j=1}^{L} {}^a c_j} \quad (6)$$

Arithmetic means and standard deviations for genomic CAIs were calculated over $C_L$ values determined for each ORF in a genome.

Genome Statistics

Annotated sequence files for 816 complete bacterial genomes were downloaded from the National Center for Biotechnology Information (NCBI) web resource (http://www.ncbi.nlm.nih.gov/genomes/lproks.cgi). Custom software was developed to calculate nucleotide composition, RNA secondary structure, and codon adaptation indices as defined above. Limits for the open reading frames were taken from the annotations in the genome sequence files.

Computational Design of Synthetic ORF Sequences

A simulated annealing algorithm was used to minimize an objective function capturing sequence features of interest within the available degrees of freedom in the i$^{th}$ trial $$E_i = \Sigma^v w_r v_r + \Sigma^c w C_o + \Sigma^s w_r S_r \quad (7)$$

where $^v w_r$, $^c w$, $^s w_r$ were the relative weights assigned regional nucleotide composition (r; N-terminal, middle, C-terminal), ORF codon adaptation index (C), and regional RNA secondary structure (S$_r$), respectively. For minimizations in which only subsets of parameters were optimized, the weights for the unconstrained parameters were set to zero. Two types of minimizations were run: minimization of the absolute objective function, or achievement of a target value. The latter mode was used to construct a series of synthetic genes in which one or more parameters was systematically varied. For target value optimization, the objective function was modified $$\Sigma w_i (p_i - v_i)^2 \quad (8)$$

where $w_t$ represents the weights, $p_i$ the parameters, and $v_i$ the target values. Sequence trial configurations were generated by randomly choosing isocodons per trial. At the beginning of the simulation, degenerative codons for each amino acid were rank-ordered by their frequency and a cut-off was applied to remove low-frequency codons (this was the reason why synthetic ORFs with low CAI values were not sampled): on average, only two codons were changed per trial. Alleles were generated by maintaining a dynamic list of ~100 sequences that were usually 10 mutations different from the current best sequence and each other. A dynamic cooling schedule was used to drive the simulated annealing progress: to determine whether the i$^{th}$ trial was acceptable, $\Delta E_i = E_i - E_{i-1}$ was calculated and i was accepted if $\Delta E_i \leq 0$ or $p_i < e^{\Delta E/T}$, where $p_i$ was a random number (0,1) [0,1] and T (a control parameter, temperature). After 1,000 trials, the acceptance rate r was accessed, T was changed if r>0.25, $T_{n+1} = 0.8 T_n$ or r<0.225, $T_{+1} = 1.3 T_n$.

Final outcomes of such minimizations were dependent on the choice of weights. Two approaches were used to address this problem. First, weights were assigned empirically in a successive number of trial and error calculations. Second, a Boltzmann decision scheme was developed that circumvents the issue of weights and enables parameters with different numerical magnitudes to be combined. In this method, three independent Boltzmann decisions were used for each of the parameter classes, respectively, resulting in a 'vote': $v_i = {^v}\beta_i + {^c}\beta_i + {^s}\beta_i$, where $\beta_i$ equals {1,0} and captures the outcome of a Boltzmann decision. Unanimous votes {$v_1=3$} were always accepted; majority votes {$v_i=2$} were accepted half the time, and minority rule {$v_i=1$} were accepted only if the overall acceptance rate had dropped below a threshold value, typically 5%. Between two to 20 runs were executed in parallel on a Beowulf cluster and merged to construct the final set of alleles. A run took 1-3 hours, depending on the size of the gene and optimization condition parameters. All synthetic ORFs were optimized within the context of the invariant 5' and 3' control regions. The resulting sequences were fed into the automated gene assembly pipeline, which assigned PCR schemes and the requisite oligonucleotide sequences (see below).

Example 2

Statistical Analysis of Bacterial Open Reading Frames (ORFs)

Regional nucleotide composition, mRNA secondary structure, and codon choice were analyzed in the 2.5×10$^6$ ORFs of 816 fully sequenced bacterial genomes that span genomic AT contents ranging from 25% to 83%. Computational algorithms and definitions of the statistical measures were described in Example 1. The AT composition of the analyzed genomes is shown in FIG. 1. The mean AU content of the first and last regions (including 35 bases) was significantly higher than the corresponding middle portion (FIG. 1A). Of the two terminal regions, the 5' end tended to have a higher AU bias than the 3' end. The variance of the nucleotide composition was also much higher at the two ends than the middle (FIG. 1B).

The mRNA secondary structure content also showed significant regional differences, with the two ends having lower mean structure content and higher variances than the middle. See FIGS. 1C and 1D. As for the AU content, the structure in the 5' segment was stronger than the 3'. The trends in these two sequence features were present regardless of genomic nucleotide composition, but with GC-rich genomes exhibiting much stronger signals than AT-rich genomes. Canonical ORFs therefore contained sequences that had above-average AU content and low secondary structure in their N- and C-terminal 35-nucleotide segments. The higher statistical variances of these parameters at one or both terminal regions relative to that observed in the middle segment suggested that some aspect of control might be encoded there: an increased level of variance in a parameter indicated that genes differ from one another in this respect as would be expected for information that contained a regulatory function.

Codon choices in a region can be quantified as the CAI (Sharp and Li, (1987)), which varies from 0 to 1, reflecting choice of low- and high-frequency codons respectively, with codon frequencies calculated over all the ORFs for each genome individually (Equations 3-6). Whereas the statistical parameters of the other two features show either independence of or near-monotonic dependence on genomic nucleotide composition, the means and variances of CAI values averaged over a genome show a considerably more complex, but well-defined pattern (FIG. 1E), precluding identification of clear canonical rules governing codon bias by this approach. In addition to the overall clear non-linear dependence on nucleotide composition, the CAI pattern also showed some regional variation. At genomic AT contents below ~50%, the N-terminal CAI tended to be significantly lower than either that observed in the middle or C-terminal segments, which were indistinguishable from one another. The variance of the N-terminal CAI values were always higher than that of the other two regions (FIG. 1F).

Canonical ORFs therefore contained sequences that had above-average AU content and low secondary structure in their N- and C-terminal segments. The higher statistical variances of these parameters at one or both terminal regions relative to that observed in the middle segment suggested that some aspect of control might be encoded there: an increased level of variance in a parameter indicated that genes differ from one another in this respect as would be expected for information that contained a regulatory function.

Parameterization of a Function that Predicts Expression Levels from ORF Sequence A function was devised in which an expression score was given as a sum of a series of thresholds applied to the composition, structure, and codon usage values of a sequence $$E = \tau_v(N) + \tau_v(C) + \tau_c(ORF) + \tau_s(N) + \tau_s(\text{middle}) + \tau_s(C) \quad (9)$$

where $\tau_v$, $\tau_c$, $\tau_s$ were regional thresholds of nucleotide composition, CAI, and structure, respectively.

A given threshold was the sum of two sigmoids $$\tau = W_p \frac{1}{1 + e^{-3\frac{x-\mu_p}{\sigma_p}}} + W_r \frac{1}{1 + e^{-3\frac{x-\mu_r}{\sigma_r}}} \quad (10)$$

where p and r denoted parameters for penalty and reward phases, respectively, W, weight, μ midpoint, σ sigmoidicity of each curve, and x the value of the parameter. The final value of the scoring function was the sum of all six components, and scoring function values were assigned to expression-level categories to the following mapping: ≤−100→0 (no expression), [−100,0]→1 (weak expression), [0,100]→2 (medium expression), >100→3 (high expression). Parameters were fit as a minimization of the sum of the absolute differences between observed and calculated expression categories, using a simulated annealing algorithm. The expression function was fit using different N- and C-terminal regional sizes, and with 35 base regions particularly exemplified.

Although the general features of the functions were relatively stable, detailed values varied according to experimental sample size and chosen region length; precise details for secondary structure contributions were particularly unstable and were therefore likely to change in future iterations.

Example 3

Multifactorial Determinants of Protein Expression in Prokaryotic Coding Regions

Oligonucleotide Synthesis and Synthetic Gene Assembly

Full-length genes (0.65-1.40 kb) encoding a synthetic ORF flanked by 5' (122 bp) and 3' (103 bp) regulatory regions were assembled from oligonucleotides (80-100 bases) synthesized in-house (MerMade 192 DNA Synthesizer (BioAutomation) (with a custom reaction protocol in which deblocking, coupling, and capping steps were performed twice to obtain high-quality product that needed no gel purification) using a robust automated PCR-mediated gene assembly procedure (Cox et al., *Protein Science* 16:379-390 (2007)). Full-length products were verified by agarose gel electrophoresis. The full-length PCR products were verified by agarose gel electrophoresis and reamplified with constant biotinylated flanking primers to provide some protection against endogenous exonuclease activity in the subsequent in vitro coupled transcription and translation reaction. To construct synthetic open reading frames, oligonucleotides of length 80-100 mer were chemically synthesized and assembled in a PCR-dependent manner.

Synthesis Reagents

Oligonucleotides were chemically synthesized on a MerMade 192 DNA synthesizer (BioAutomation Corp., MM-192) using standard phosphoramidite chemistries (Caruthers et al., (1987); Caruthers et al., (1983)). Controlled-pore glass (CPG) columns were placed into the synthesis manifold as indicated by the software and were sealed into the manifold with a rubber mallet. Phosphoramidites were solubilized to a concentration of 1 g per 20 mL directly before use. Reagents, part numbers, and vendor information are summarized in Table 1.

TABLE 1

List of reagents and consumables for synthesis of oligonucleotides used to construct synthetic genes

| Reagent | Part number | Source | Description |
|---|---|---|---|
| Deblock | BIO830 | EMD Biosciences | dichloroacetic acid (3%) in dichloromethane |
| Cap A | BIO221 | EMD Biosciences | 2,6-lutidine (10%), acetic anhydride (10%) in THF |
| Cap B | BIO345 | EMD Biosciences | methylimidazole (16%) in THF |
| Oxidizer | BIO420 | EMD Biosciences | 0.02M iodine in THF (70%), pyridine (20%), water (10%) |
| Activator | BIO152 | EMD Biosciences | 0.25M 5-(ethylthio)-1H-tetrazole in acetonitrile |
| Acetonitrile (wash) | AX0151 | EMD Biosciences | acetonitrile, anhydrous |
| Acetonitrile (diluent) | 40-4050-50 | Glen Research | acetonitrile, anhydrous |
| dA phosphoramidite | 10-1000 | Glen Research | dA-CE phosphoramidite |
| dC phosphoramidite | 10-1015 | Glen Research | Ac-dC-CE phosphoramidite |
| dG phosphoramidite | 10-1029 | Glen Research | dmf-dG-CE phosphoramidite |
| dT phosphoramidite | 10-1030 | Glen Research | dT-CE phosphoramidite |
| dA CPG column | SCG1-1000-5 | Biosearch | 5'-DMT-dA(Bz)-Suc, 1000 Å, 50 nmol |
| dC CPG column | SCG1-1100A-5 | Biosearch | 5'-DMT-dC(Ac)-Suc, 1000 Å, 50 nmol |
| dG CPG column | SCG1-1200F-5 | Biosearch | 5'-DMT-dG(dmf)-Suc, 1000 Å, 50 nmol |
| dT CPG column | SCG1-1300-5 | Biosearch | 5'-DMT-dT-Suc, 1000 Å, 50 nmol |
| Water traps | TP-(gram amount) | ChemAssist | Molecular trap pack |

Synthesis Protocol

Prior to the start of synthesis, the CPG columns were rinsed twice with synthesis grade anhydrous acetonitrile, capped twice with capping reagents, and again washed twice with acetonitrile. Synthesis then proceeded with the steps of deblocking (twice), washing (twice), coupling (twice), washing, capping, washing, oxidation, washing, another capping, and washing (twice) in sequential order. At the completion of synthesis, the columns were incubated with deblock three times and washed three times. During all chemical based reaction steps (deblocking, coupling, capping and oxidation), two short vacuum pulses were applied to the columns approximately at 15 and 30 seconds reaction time. This technique pulled 'new' reagent placed on top of the column into the synthesis resin. General overview of reaction order, reagent volume, and reaction times are provided in Tables 2-4.

TABLE 2

Table of pre-synthesis reaction sequence

| Step | Volume | Incubation time (s) | Vac. Pulse |
|---|---|---|---|
| Wash | 250 μL acetonitrile | 0 | N/A |
| Wash | 250 μL acetonitrile | 0 | N/A |
| Capping | 60 μL cap A reagent<br>60 μL cap B reagent | 45 | Two |
| Capping | 60 μL cap A reagent<br>60 μL cap B reagent | 45 | Two |
| Wash | 250 μL acetonitrile | 0 | N/A |
| Wash | 250 μL acetonitrile | 0 | N/A |

TABLE 3

Table of synthesis reaction sequence, per monomer

| Step | Volume | Incubation time (s) | Vac. Pulse |
|---|---|---|---|
| Deblock | 120 μL deblock | 50 | Two |
| Deblock | 120 μL deblock | 50 | Two |
| Wash | 250 μL acetonitrile | 0 | N/A |
| Wash | 250 μL acetonitrile | 0 | N/A |
| Couple | 60 μL phosphoramidite<br>80 μL activator | 75 | Two |
| Couple | 60 μL phosphoramidite<br>80 μL activator | 75 | Two |
| Wash | 250 μL acetonitrile | 0 | N/A |
| Capping | 60 μL cap A reagent<br>60 μL cap B reagent | 45 | Two |
| Wash | 250 μL acetonitrile | 0 | N/A |
| Oxidize | 95 μL oxidizer | 45 | Two |
| Wash | 250 μL acetonitrile | 0 | N/A |
| Capping | 60 μL cap A reagent<br>60 μL cap B reagent | 45 | Two |
| Wash | 250 μL acetonitrile | 0 | N/A |
| Wash | 250 μL acetonitrile | 0 | N/A |

TABLE 4

Table of post-synthesis reaction sequence

| Step | Volume | Incubation time (s) | Vac. Pulse |
|---|---|---|---|
| Deblock | 120 μL deblock | 50 | Two |
| Deblock | 120 μL deblock | 50 | Two |
| Deblock | 120 μL deblock | 50 | Two |
| Wash | 250 μL acetonitrile | 0 | N/A |
| Wash | 250 μL acetonitrile | 0 | N/A |
| Wash | 250 μL acetonitrile | 0 | N/A |

Oligonucleotide Postprocessing

Oligonucleotides were chemically cleaved from CPG columns by incubation in strong base. 100 μL of ~30% ammonium hydroxide (VWR, EM-AX1303-11) was placed into the CPG column and incubated at room temperature for 15 min. After incubation, the ammonium solution was captured in a 2 mL deepwell microplate (Phenix Research, M-1810) in the microplate cleavage apparatus (BioAutomation, MPMM192-1-029). This process was repeated twice more for a total of three cleavage incubations. Next, the plate was sealed with an adhesive aluminum foil sheet (ISC BioExpress, T-2420-1), placed into a microplate deprotection chuck (BioAutomation, A-MM192-DEPROTECTION CHUCK), and deprotection proceeded in the ammonia overnight (16-20 hours) at 55° C.

After deprotection, the ammonium was removed in an evaporative microplate dryer (BioAutomation, 11-80965) at 55° C., 20 L/min air, for 10-20 min. After this time, an approximate volume of ~200 μL remained. Ten volumes (2 mL) of 1-butanol (Sigma Aldrich, B7906) were added to each microwell and the plate was sealed in a thermal microplate sealer (REMP, EasySealer) with an Easy Peel Heat Sealing Film sheet (ISC BioExpress, T-2418-1). To solubilize the water solution into the butanol, the plate was rotated end-over-end on a Mini LabRoller (Labnet International, H5500) for 10-15 min. Next, the precipitated oligonucleotides were pelleted by centrifugation at 2,500 g for 10 min in microplate centrifuge (Thermo Fisher Scientific, 11177564). The sealing film was discarded and the plate was carefully decanted. The oligonucleotide pellets were then dried in the evaporative microplate dryer at 55° C., 20 L/min air, for 5-15 min, until devoid of any moisture. The oligonucleotides were then resuspended in 300 μL of TE buffer (10 mM Tris (pH 8.0), 1 mM EDTA).

Next, the oligonucleotides were diluted 200-fold (1 μL stock into 199 μL of water) in a UV-transparent microplate (Costar, 3635) and mixed. The dilution plate was then read in a microplate spectrophotometer (Tecan, GENios) and the stock oligonucleotide concentration was determined. A software program, REARRYER, then created movement scripts for a Tecan Genesis or Evo liquid handling robot to facilitate volume additions to dilute each individual oligonucleotide to a common stock concentration (e.g., 100 μM). The stock plate was placed on the robot, the script was executed, and the oligonucleotides were brought to identical concentrations and mixed. A working dilution plate was then made for gene synthesis (1 μM) in a 1 mL microplate (Nalge Nunc, 260252) and used for robotically assembled synthetic gene building.

Synthetic Open Reading Frame Creation

The synthetic open reading frames were constructed in an automated fashion from the oligonucleotide stocks as previously described (Cox et al., (2007)) by using inside-out nucleation of gene fragments (Gao et al., (2003)) and splice-overlap extension PCR (Horton et al., (1989)) to fabricate full-length genes. Tables 5, 6 and 7 indicate the characteristics of the oligonucleotide scaffold system used to create the ORFs in this work for *Leishmania mexicana* triosephosphate isomerase, E65Q mutant (lmTIM; GI:12084529; SEQ ID NO:4), *Gallus gallus* liver basic fatty acid binding protein (ggFABP; GI:12084529; SEQ ID NO:2); and *Thermus thermophilus* aspartate aminotransferase (ttAST; GI:5821836; SEQ ID NO:1). ORFs were encoded as a two fragment system comprised of four primer pairs per fragment.

TABLE 5

The characteristics of the oligonucleotide scaffold system used to create the ORFs for lmTIM, where strand indicates sense (S) or anti-sense (A) directionality

| Oligo # | Fragment | Oligo pair | Strand | Start nucleotide | End nucleotide |
|---|---|---|---|---|---|
| 1 | A | 1 | S | 184 | 274 |
| 2 | A | 1 | A | 335 | 245 |
| 3 | A | 2 | S | 123 | 213 |
| 4 | A | 2 | A | 397 | 306 |
| 5 | A | 3 | S | 62 | 152 |
| 6 | A | 3 | A | 459 | 368 |
| 7 | A | 4 | S | 1 | 91 |
| 8 | A | 4 | A | 521 | 430 |
| 9 | B | 1 | S | 675 | 765 |
| 10 | B | 1 | A | 826 | 736 |
| 11 | B | 2 | S | 614 | 704 |
| 12 | B | 2 | A | 888 | 797 |
| 13 | B | 3 | S | 553 | 643 |
| 14 | B | 3 | A | 950 | 859 |
| 15 | B | 4 | S | 492 | 582 |
| 16 | B | 4 | A | 1012 | 921 |

TABLE 6

The characteristics of the oligonucleotide scaffold system used to create the ORFs for ggFABP, where strand indicates sense (S) or anti-sense (A) directionality

| Oligo # | Fragment | Oligo pair | Strand | Start nucleotide | End nucleotide |
|---|---|---|---|---|---|
| 1 | A | 1 | S | 107 | 188 |
| 2 | A | 1 | A | 240 | 159 |
| 3 | A | 2 | S | 54 | 136 |
| 4 | A | 2 | A | 292 | 211 |
| 5 | A | 3 | S | 1 | 83 |
| 6 | A | 3 | A | 344 | 263 |
| 7 | B | 1 | S | 420 | 501 |
| 8 | B | 1 | A | 553 | 472 |
| 9 | B | 2 | S | 368 | 449 |
| 10 | B | 2 | A | 605 | 524 |
| 11 | B | 3 | S | 315 | 397 |
| 12 | B | 3 | A | 657 | 576 |

TABLE 7

The characteristics of the oligonucleotide scaffold system used to create the ORFs for ttAST, where strand indicates sense (S) or anti-sense (A) directionality

| Oligo # | Fragment | Oligo pair | Strand | Start nucleotide | End nucleotide |
|---|---|---|---|---|---|
| 1 | A | 1 | S | 178 | 266 |
| 2 | A | 1 | A | 324 | 237 |
| 3 | A | 2 | S | 119 | 207 |
| 4 | A | 2 | A | 382 | 295 |
| 5 | A | 3 | S | 60 | 148 |
| 6 | A | 3 | A | 440 | 353 |
| 7 | A | 4 | S | 1 | 89 |
| 8 | A | 4 | A | 498 | 411 |
| 9 | B | 1 | S | 646 | 734 |
| 10 | B | 1 | A | 792 | 705 |
| 11 | B | 2 | S | 587 | 675 |
| 12 | B | 2 | A | 850 | 763 |
| 13 | B | 3 | S | 528 | 616 |
| 14 | B | 3 | A | 908 | 821 |
| 15 | B | 4 | S | 469 | 557 |
| 16 | B | 4 | A | 879 | 966 |
| 17 | C | 1 | S | 114 | 1202 |
| 18 | C | 1 | A | 1260 | 1173 |
| 19 | C | 2 | S | 1055 | 1143 |
| 20 | C | 2 | A | 1318 | 1231 |
| 21 | C | 3 | S | 996 | 1084 |
| 22 | C | 3 | A | 1376 | 1289 |
| 23 | C | 4 | S | 937 | 1025 |
| 24 | C | 4 | A | 1434 | 1347 |

In vitro Coupled Transcription and Translation Reactions

An in vitro coupled transcription and translation (TnT) system was used, based on the PANOxSP E. coli S30 lysate system (Jewitt & Swartz Biotechnol. Bioeng 86:19-26 (2004); Jewitt & Swartz Biotechnol. Bioeng. 87:465-472 (2004)). An S30 lysate was prepared from BL21 Star (DE3) E. coli cells (Invitrogen) grown to mid-log phase in shaking culture flasks, rinsed of medium, flash-frozen, thawed, lysed in a French press, centrifuged to remove cellular debris, and incubated to facilitate a 'run-off' of any mRNA still bound to ribosomal complexes. The lysate was dialyzed, centrifuged again to remove precipitants, and stored in flash-frozen aliquots. The reactions were initiated by adding biotinylated linear PCR template (1 μg per 100 μL reaction) to purified S30 lysate along with a reaction master mix which contained magnesium glutamate, ammonium glutamate, potassium glutamate, canonical ribonucleotide triphosphates, folinic acid, total E. coli tRNAs, amino acids, phosphoenolpyruvate, nicotinamide adenine dinucleotide, coenzyme A, oxalic acid, putrescine, spermidine, and rifampicin. The components were mixed gently by repeated aspiration/dispense pipetting and incubated for 5 hours at 30° C., 500 rpm, in a RTS ProteoMaster instrument (Roche), in uncapped reaction tubes sealed with an Air Pore membrane (Qiagen) to facilitate oxygen exchange while minimizing evaporation. After incubation, expressed protein was purified by affinity chromatography (see below).

Several biological components were used to synthesize protein from a DNA template. The soluble portion of the cytoplasm was crudely purified and contained the proteins to carry out translation. Additionally, raw materials, energy sources, stabilizers, inhibitors and energy regeneration molecules were added. The in vitro protein expression system described here was principally derived from PANOx (Jewett and Swartz, (2004b); Kim and Swartz, (2001)) PANOxSP (Jewett and Swartz, (2004a, c)), and Cytomim (Jewett and Swartz, (2004a)).

S30 Lysate Preparation

In prokaryotic cells, the events of transcription and translation (TnT) were coupled, with translation starting before the RNA polymerase finished transcribing the message RNA. Thus, a crude purification of bacterial cell lysate contained the cellular machinery for mRNA transcription and protein translation. Extract contained the machinery required for translation, including ribosomes, ribosome initiation factors, ribosome elongation factors, ribosome termination factors, etc. Small molecules, raw materials and cofactors were added in addition to the DNA template to produce protein from a cell-free extract. A TnT reaction produced protein for a limited amount of time, usually until either one of the amino acids or the energy supply was depleted and/or degraded.

One mechanism of energy and reagent depletion was likely through unregulated, endogenous cellular phosphatases that nonspecifically dephosphorylate ribonucleotide triphosphates in the reaction mix. This drastically cut the effective energy supply, limiting protein production (Kawarasaki et al., (1995)). Alternative solutions to this issue greatly increase the complication of lysate production. However, exogenous inorganic phosphate and glucose in the medium downregulates expression of some *E. coli* phosphatases (Kim and Choi, (2001)). This step more than doubled effective expression time with a ~35% increase in expressed protein.

The procedure to produce cell-free extract has been streamlined by others (Liu et al., (2005)) and removes superfluous steps found in older extract preparation methods. The expression system presented here utilized the BL21 Star (DE3) cell strain. The BL21 Star strain contained a deletion in the rne131 gene, coding for RNase E. This specific deletion contained the N-terminal domain for obligate ribosomal RNA processing but lacked the C-terminal domain (Kido et al., (1996); Lopez et al., (1999)). Removal of this domain increased the stability of the mRNA and improved protein production in cell-free extracts (Alm et al., (2005); Hahn and Kim, (2006)). This strain also contained a DE3 lysogen that harbored T7 RNA polymerase under control of a lac promoter.

To begin the process of lysate creation, BL21 Star (DE3) competent cells (Invitrogen, C6010-03) were plated on a LB agar plate to yield distinct colonies. The plate was incubated overnight at 37° C. The next day, a sterile, baffled 250 mL flask was filled with 75 mL of 2×YT-PG medium (16 g/L tryptone (Sigma Aldrich, T7293), 10 g/L yeast extract (Sigma Aldrich, 70161), 5 g/L NaCl (Sigma Aldrich, 71376), 22 mM $NaH_2PO_4$ (Sigma Aldrich, S5011), 40 mM $Na_2HPO_4$ (Sigma Aldrich, S5136), and 100 mM glucose (Sigma Aldrich, G7021)). One colony of BL21 Star (DE3) was used to inoculate the medium and the flask was incubated on a shaking platform overnight at 37° C.

The overnight seed culture was used to inoculate large, baffled flasks for growth. During logarithmic growth phase, the cell strain was mildly induced to express T7 RNA polymerase. Prior to an initial fermentation, an optical density-based growth curve was performed to determine times of lagging and logarithmic growth, as these can greatly vary between medium ingredient lots, different flask sizes, different incubators, etc. Thus, baffled culture flasks containing 2×YT-PG medium were inoculated with 1/100th volume of overnight culture. The flasks were incubated on a shaking platform at 37° C. (at 115 rpm for six liter baffled flasks) according to the pre-established growth curve; cultures were grown to approximately 30% of completion of logarithmic growth (~2.5 hours for 1.5 liter medium in a six liter baffled flask) and T7 RNA polymerase expression was induced with the addition of 0.25 M IPTG.

Cultures were permitted to grow and continue expression until reaching approximately 75% of completion of logarithmic growth (an additional ~1.75 hours at the above conditions) and then immediately chilled on ice for 15 min. The cells were then harvested by centrifugation in a pre-chilled rotor at 4° C. for 20 min at 5,000 g. Next, the cell pellets were washed by decanting the exhausted medium supernatant and resuspending the pellets in 1/20th original medium volume of S30 buffer (10 mM Tris-acetate, (pH 8.2; Sigma Aldrich, T1258), 14 mM magnesium acetate tetrahydrate (Sigma Aldrich, M5661), 60 mM potassium acetate (Sigma Aldrich, P1190), and 2 mM dithiotheitol (Sigma Aldrich, D9779)). The pellets were resuspended through vigorous agitation with a microcentrifuge tube vortexer, or a cordless drill with a plastic spatula attached as the bit (VWR, 53800-005). Two empty 250 mL conical centrifuge tubes were weighed and the mass was recorded. The resuspended cell slurry was divided among the tubes and pelleted at 4° C. for 10 min at 5,000 g. The tubes were then carefully decanted and weighed again to determine the wet cell paste mass. Finally, the pellets were flash frozen in liquid nitrogen and stored overnight at −80° C.

Next, the frozen cell pellets were thawed on ice for approximately one hour. S30 buffer was added at a volume of 1 mL per g of wet cell paste, and the pellets were resuspended by vortexing. DTT was added to the approximate volume of cell slurry to a concentration of 5 mM. The cells were then ruptured by application of a French press at 17,000 psi one or two times. The soluble fraction was enriched by centrifugation at 4° C., 30,000 g, for 30 min. The soluble portion was then clarified again by a second centrifugation application at 4° C., 30,000 g, for 30 min in a new centrifuge tube.

A simplified run-off reaction (Liu et al., (2005)) was performed to facilitate release of *E. coli* mRNA from the ribosomes; the run-off reaction does not require any reagents. The centrifuged supernatant was carefully aspirated and placed into centrifuge tubes (e.g., 15 mL or 50 mL conical tubes) and was incubated at 37° C. for 80 min, rotating end-over-end on a Mini LabRoller (Labnet International, H5500) in the dark (alternatively, the tubes were covered with foil). Next, the lysate was dialyzed to control the pH and salt concentration, and then clarified to remove any precipitated proteins. During the run-off reaction, dialysis tubing (6-8 kDa MWCO; Spectra/Por, 132-650) was prepared by equilibration in Heavy Metals Cleaning Solution (Spectra/Por, 132-908) for approximately one-half hour. The tubing was then copiously washed with ultra-pure water. The run-off reaction was loaded into the tubing and then dialyzed into approximately 80 volumes of pre-chilled S30 buffer at 4° C. for one-hour. After dialysis, the lysate was centrifuged at 4° C., 4,000 g, for 10 min to remove precipitated products. Finally, the cell-free extract was aliquoted into microcentrifuge tubes, flash-frozen in liquid nitrogen, and stored at −80° C. The lysate was stable without reduction in expression for at least two months.

Reaction Mix Formulation

The 4× reaction mix contained the small molecules, energy compounds, raw materials, and cofactors used to fuel transcription and translation in the cell-free extract. It contained magnesium glutamate, ammonium glutamate, potassium glutamate, the canonical ribonucleotide triphosphates, folinic acid, *E. coli* total tRNAs, the canonical amino acids, phosphoenolpyruvate, nicotinamide adenine dinucleotide, coenzyme A, oxalic acid, putrescine, spermidine, and rifampicin. (See Tables 8 and 9). Solutions that were not completely consumed in one batch of reaction mix were stored at −80° C. Putrescine and spermidine were incubated at 37° C. to change phase into liquid form and were pipetted rather than weighed. Solutions listed as "unbuffered" were not pH-corrected with acid or base due to the solutions' weak buffering capacity, or because it was specifically left unbuffered in previous protocols.

TABLE 8

Table of reagents included in the reaction master mix

| Reagent | Part number | Source | Description |
|---|---|---|---|
| PEP | 108294 | Roche | phosphoenol-pyruvate monopotassium salt |
| NAD | N6522 | Sigma Aldrich | β-Nicotinamide adenine dinucleotide hydrate |
| CoA | C4282 | Sigma Aldrich | coenzyme A hydrate |
| Putrescine | D13208 | Sigma Aldrich | 1,4-Butanediamine |
| Spermadine | S0266 | Sigma Aldrich | N-(3-Aminopropyl)-1,4-diaminobutane |
| Oxalate | O0501 | Sigma Aldrich | potassium oxalate monohydrate |
| Magnesium glutamate | 49605 | Sigma Aldrich | L-glutamic acid hemimagnesium salt tetrahydrate |
| Ammonium glutamate | G1376 | Sigma Aldrich | L-glutamic acid ammonium salt |
| Potassium glutamate | G1501 | Sigma Aldrich | L-glutamic acid potassium salt monohydrate |
| Folinate | F7878 | Sigma Aldrich | folinic acid calcium salt |
| tRNAs | 109550 | Roche | tRNA from *E. coli* MRE 600 |
| Rifampicin | R3501 | Sigma Aldrich | rifampicin |
| rATP | A2383 | Sigma Aldrich | adenosine 5'-triphosphate disodium salt |
| rCTP | C1506 | Sigma Aldrich | cytidine 5'-triphosphate disodium salt |
| rGTP | G8877 | Sigma Aldrich | guanosine 5'-triphosphate sodium salt hydrate |
| rUTP | U6750 | Sigma Aldrich | uridine 5'-triphosphate trisodium salt hydrate |
| Alanine | 5129 | Sigma Aldrich | L-alanine |
| Arginine | 11009 | Sigma Aldrich | L-arginine |
| Asparagine | 11009 | Sigma Aldrich | L-asparagine |
| Aspartate | 11149 | Sigma Aldrich | L-aspartic acid |
| Cysteine | 30089 | Sigma Aldrich | L-cysteine |
| Glutamate | 49449 | Sigma Aldrich | L-glutamic acid |
| Glutamine | 49419 | Sigma Aldrich | L-glutamine |
| Glycine | 50049 | Sigma Aldrich | Glycine |
| Histidine | 53319 | Sigma Aldrich | L-histidine |
| Isoleucine | 58879 | Sigma Aldrich | L-isoleucine |
| Leucine | 61819 | Sigma Aldrich | L-leucine |
| Lysine | 62929 | Sigma Aldrich | L-lysine monohydrochloride |
| Methionine | 64319 | Sigma Aldrich | L-methionine |
| Phenylalanine | P5482 | Sigma Aldrich | L-phenylalanine |
| Proline | 81709 | Sigma Aldrich | L-proline |
| Serine | 84959 | Sigma Aldrich | L-serine |
| Threonine | 89179 | Sigma Aldrich | L-threonine |
| Tryptophan | 93659 | Sigma Aldrich | L-tryptophan |
| Tyrosine | 93829 | Sigma Aldrich | L-tyrosine |
| Valine | 94620 | Sigma Aldrich | L-valine |

A nineteen amino acid mixture was prepared as a suspended mixture first, excluding tyrosine due to its poor solubility at physiological conditions. A 250 mL solution of 50 mM amino acids was created by combining 1.46 g valine, 2.53 g tryptophan, 2.07 g phenylalanine, and 1.64 g isoleucine in 200 mL of pure water. These were incubated at 37° C. with mixing or agitation for 15 min to facilitate dissolution. Next, 1.64 g leucine and 1.52 g cysteine were added, and the solution was again incubated at 37° C. with mixing or agitation for 15 min. Then, 1.87 g methionine, 1.11 g alanine, 2.18 g arginine, 1.65 g asparagine, 1.66 g aspartate, 1.84 g glutamate, 0.94 g glycine, and 1.83 g glutamine were added. The pH was then adjusted by addition of 1.0 mL of 10N KOH (Sigma Aldrich, P5958). Finally, 1.94 g histidine, 2.28 g lysine, 1.44 g proline, 1.31 g serine, and 1.49 g threonine were dissolved, and the solution volume was brought up to 250 mL. The solution was divided into six aliquots of 41 mL each, and extra aliquots were stored at −80° C.

TABLE 9

Table of stock concentrations, volumes, and pH used to construct the 4X reaction master mix solution

| Solution | [Stock] | Solution Volume | Amount | Final pH | Acid/base |
|---|---|---|---|---|---|
| PEP | 1M | 35 mL | 7.22 g | 6.8-7.3 | 10N KOH |
| NAD | 50 mM | 7 mL | 232 mg | 6-7 | 10N KOH |
| CoA | 40 mM | 7 mL | 215 mg | 7.3 | 10N KOH |
| Putrescine | 100 mM | 10 mL | 88.2 mg/100.5 µL | 7.3 | glacial HOAc |
| Spermidine | 100 mM | 15 mL | 218 mg/236 µL | 7.3 | glacial HOAc |
| Oxalate | 1M | 15 mL | 2.76 g | 8.4 | unbuffered |
| $Mg^{++}$ glutamate | 1M | 50 mL | 19.43 g | 7.3 | 10N KOH |
| $NH_4^+$ glutamate | 1.5M | 50 mL | 12.32 g | 7.3 | 10N KOH |
| $K^+$ glutamate | 3.5M | 250 mL | 177.83 g | 8.2 | unbuffered |
| Folinate | 10.8 mg/mL | 15 mL | 162 mg | 7-7.5 | unbuffered |

TABLE 9-continued

Table of stock concentrations, volumes, and pH used to construct the 4X reaction master mix solution

| Solution | [Stock] | Solution Volume | Amount | Final pH | Acid/base |
|---|---|---|---|---|---|
| tRNAs | 34 mg/mL | 5 mL | 172 mg | 7.2 | dissolved in 10 mM K2PO4, pH 7.2 |
| Rifampicin | 1 mg/mL | 50 mL | 50 mg | 6-7 | 10N KOH |
| rATP | 500 mM | 5 mL | 1.38 g | 7.3 | 10N KOH |
| rCTP | 500 mM | 5 mL | 1.32 g | 7.3 | 10N KOH |
| rGTP | 500 mM | 5 mL | 1.31 g | 7.3 | 10N KOH |
| rUTP | 500 mM | 5 mL | 1.38 g | 7.3 | 10N KOH |
| 19 amino acids | 50 mM | 250 mL | Various | n/a | 10N KOH |

The 4× reaction master mix was created as follows and summarized in Table 10. 250 mL of reaction master mix was prepared at one time, enough to fuel 1 liter of total TnT reactions. First, the nineteen amino acid solution was added to a clean beaker, along with the powdered tyrosine, and water. The solution was mixed well. Next, the glutamate salts were added, and the solution was again mixed well. Then, folinic acid, tRNAs, PEP, NAD, coenzyme A, oxalic acid, putrescine, spermadine, and rifampicin were added and mixed. Finally, the four ribonucleotides were added and mixed. The 4× reaction master mix was then flash-frozen in liquid nitrogen and stored at −80° C. Because some of tyrosine was not soluble at this concentration, the master mix solution was kept stirring during aspiration and aliquoting to keep the tyrosine flakes distributed throughout the master mix.

TABLE 10

Table of stock volumes used to create the 4X reaction master mix

| Solution | Stock | Amount to add | 4x conc. | 1x conc. |
|---|---|---|---|---|
| 19 amino acids | 50 mM | 40 mL | 8 mM | 2 mM |
| Tyrosine | n/a | 371 mg | 8 mM | 2 mM |
| Water | n/a | 37.3 mL | n/a | n/a |
| Mg++ glutamate | 1M | 10 mL | 40 mM | 10 mM |
| NH4+ glutamate | 1.5M | 6.7 mL | 40 mM | 10 mM |
| K+ glutamate | 3.5M | 50 mL | 700 mM | 175 mM |
| Folinate | 10.8 mg/mL | 3.14 mL | 136 µg/mL | 34 µg/mL |
| tRNAs | 34 mg/mL | 5 mL | 682 µg/mL | 171 µg/mL |
| PEP | 1M | 33.3 mL | 120 mM | 30 mM |
| NAD | 50 mM | 6.67 mL | 1.33 mM | 0.33 mM |
| CoA | 40 mM | 6.67 mL | 1.08 mM | 0.27 mM |
| Oxalate | 1M | 2.7 mL | 10.8 mM | 2.7 mM |
| Putrescine | 100 mM | 10 mL | 4 mM | 1 mM |
| Spermadine | 100 mM | 15 mL | 6 mM | 1.5 mM |
| Rifampicin | 1 mg/mL | 15 mL | 40 µg/mL | 10 µg/mL |
| rATP | 500 mM | 2.5 mL | 5 mM | 1.25 mM |
| rCTP | 500 mM | 2 mL | 4 mM | 1 mM |
| rGTP | 500 mM | 2 mL | 4 mM | 1 mM |
| rUTP | 500 mM | 2 mL | 4 mM | 1 mM |

DNA Template Characteristics

A DNA template was supplied for transcription and subsequent translation. It was advantageous to supply a DNA template and perform transcription rather than just supplying a purified mRNA template because the activity of endogenous ribonucleases in the extract is high, and an mRNA template generally lasts on the order of seconds-to-minutes. By constantly regenerating mRNA from a DNA template, a large amount of protein can be produced. Additionally, the mRNA may have a stem-loop structure to enhance message stability. The template and its synthesis have been previously described above. In addition to a gene, the synthetic construct contained a T7 RNA polymerase promoter (Chamberlin et al., (1970); Davanloo et al., (1984)), a Shine-Dalgarno ribosome binding site (Curry and Tomich, (1988); Shine and Dalgarno, (1974)), an optimized open reading frame, and a T7 terminator stem-loop structure (Mertens et al., (1996)).

The untranslated promoter and terminator segments are provided below. The 5' segment contained a T7 RNA polymerase promoter (in bold) as well as a Shine-Delgarno ribosome binding site (in italics).

(SEQ ID NO: 5)
5'-CGGCGTAGAGGATCGAGATCTCGATCCCGCGAAATAATACGACTCA

CTATAGGGAATTGTGAGCGGATAACAATTCCCCTCTAGAAATAATTTTG

TTTAACTTTAA*GAAGGAGATATACC*-3'.

The 3' segment contained a gly-gly-ser fusion linker (in bold), poly-histidine purification tag (in italics), and two stop codons (underlined) as well as a T7 transcriptional terminator structure.

(SEQ ID NO: 6)
5'-GGCGGCTCCCACCATCACCATCACCATTAATGAGAGATCCGGCTGCT

AACAAAGCCCGAAAGGAAGCTGAGTTGGCTGCTGCCACCGCTGAGCAATA

ACTAGCATAACCCCTTGGGGCCTCTAAACGGGTCTTGAGG-3'.

Purification of Proteins Encoded by Synthetic Genes

Protocols were developed for quantifiable protein production and purification. All three proteins were constructed with a C-terminal hexahistidine fusion and purified using EZview Red HIS-Select HC Nickel Affinity Gel (Sigma Aldrich). A suspended gel slurry of 50 µL was washed with 1 mL loading buffer (20 mM MOPS (pH 7.5), 7.5 mM imidazole, 500 mM NaCl). Completed TnT reactions (25-100 µL) were combined with the washed affinity gel in the addition of 1 mL loading buffer and captured at 4° C. for 1 hour rotating end-over-end in a Mini LabRoller (Labnet International), followed by washing with loading buffer (twice with 1 mL), and elution of bound protein with 100 µL elution buffer (20 mM MOPS (pH 7.5), 400 mM imidazole, 500 mM NaCl) incubating for 30 min at 4° C. (rotating end-over-end). Each affinity elution was concentrated using Vivaspin 500 centrifugal concentrators (Sartorius Stedim, 5 kDa molecular weight cut-off) by centrifugation at 13,500 g for 10-15 min. The entire final volume (~25 µL) was loaded into one SDS-PAGE gel lane; the gel was stained with GelCode Blue Stain Reagent (Thermo Fisher Scientific). A poly-histidine tagged GFP template was included in each experiment as a positive expression and purification control, a TnT reaction incubated without any DNA template was used as a negative control. Nearly 286 synthetic genes were tested in at least two independent experiments. The seven condition experiments for all three scaffolds were tested in at least three independent experiments and the majority of the other synthetic genes were tested in at least two independent experiments.

Protein Identification by Mass Spectrometry

Figure 2:
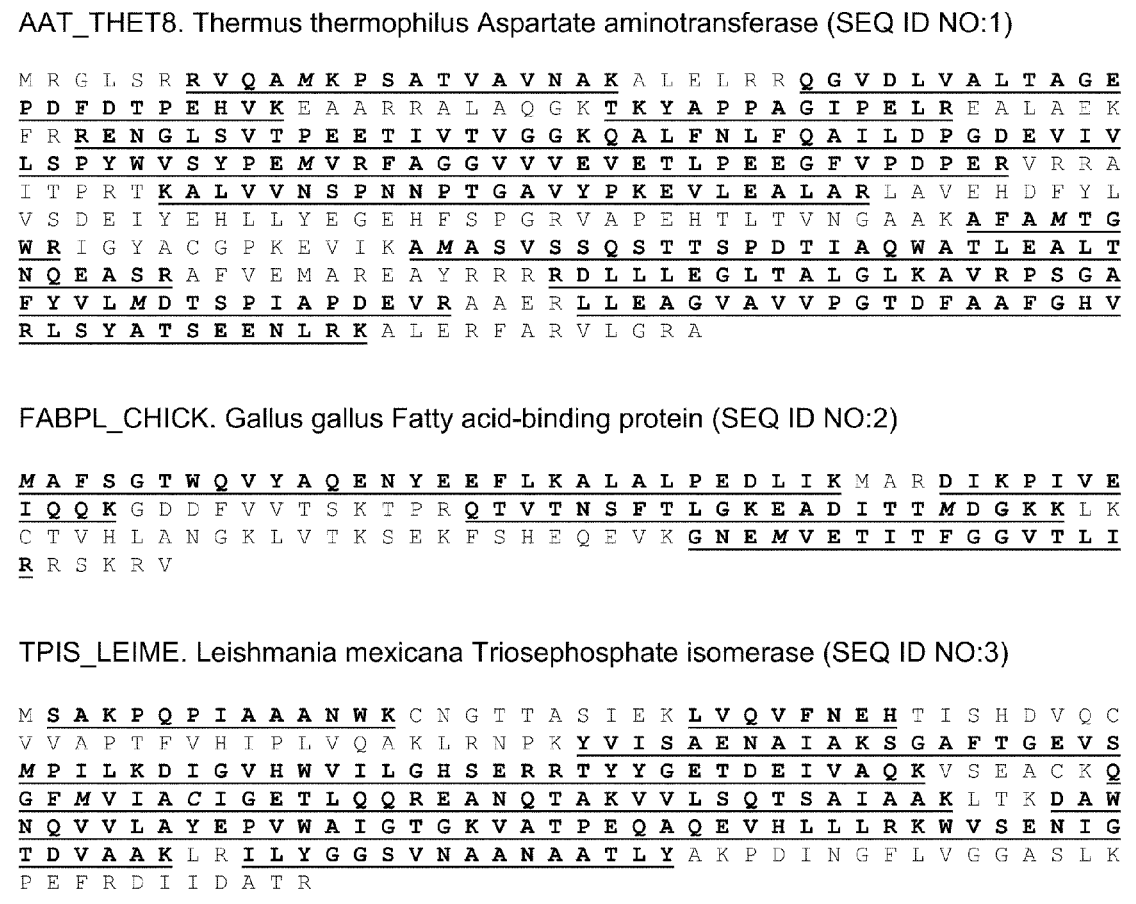

Liquid chromatography (LC)—tandem mass spectrometry (MS/MS) was used to validate protein identifications, by analysis of peptides generated from in-gel tryptic digests. Samples were prepared according to the in-gel digestion protocol available at http://www.genome.duke.edu/cores/proteomics/sample-preparation/. Approximately half of the sample from each gel band was analyzed on a nanoAcquity LC and Synapt HDMS system (Waters Corporation) using a 30 min LC gradient, with the top three precursor ions from each MS scan selected for MS/MS sequencing. Raw data was processed using Mascot Distiller v2.0 and searched against the Swiss-Prot database (v57.11) using Mascot v2.2 (Matrix Sciences), allowing for fixed modification of Cys (carbamidomethylation) and variable modification of Met (oxidation). Scaffold (v2.6) was used to validate the peptide and protein identifications. Sequence coverage obtained from this analysis for each of the proteins is shown in FIG. 2.

Determination of mRNA Levels mRNA levels were examined by addition of 10 µCi of α-labeled rATP (Perkin Elmer). Aliquots of 10 µL were removed from the expression reaction and immediately mixed into 100 µL Trizol (Invitrogen), incubated (5 min, room temperature), followed by addition of 20 µL chloroform (3 min at ambient temperature), and followed by vortexing (15 seconds). To separate phases, the samples were centrifuged at 12,000 g (15 min), and the RNA-containing aqueous phase was aspirated and processed through a NucAway Spin Column (Applied Biosystems) to remove unincorporated label. The entire eluate (~50 µL) was mixed with 200 µL of OptiPhase SuperMix scintillation cocktail (Perkin Elmer) and counted in a MicroBeta Trilux scintillation counter (Perkin Elmer). To determine the optimal reading point, a time course was constructed using aliquots taken at 0, 5, 10, 15, 30, 45, 60, 120, 180, 240 and 300 min for a poorly and highly expressing template respectively for each of the three genes. Near-maximal mRNA levels were observed at one hour; this single time point was used subsequently to characterize the alleles.

Example 4

Construction and Expression Patterns of Synthetic Genes in *E. coli*

The bioinformatic analysis indicated that regional AU content and secondary structure at the beginning and end of ORFs were a feature that was apparently conserved across bacterial species. The higher variances of these two parameters relative to the middle region of the ORF further suggested that they may play a role in some control processes. However, this analysis provided no further information on their functional importance, nor did it provide guidance on codon usage. To test experimentally whether these features played a role in effecting protein expression levels and their relative contributions, a computer algorithm (ORFOPT) was developed to specify qualitatively their presence in synthetic genes. See Example 1.

Figure 4:
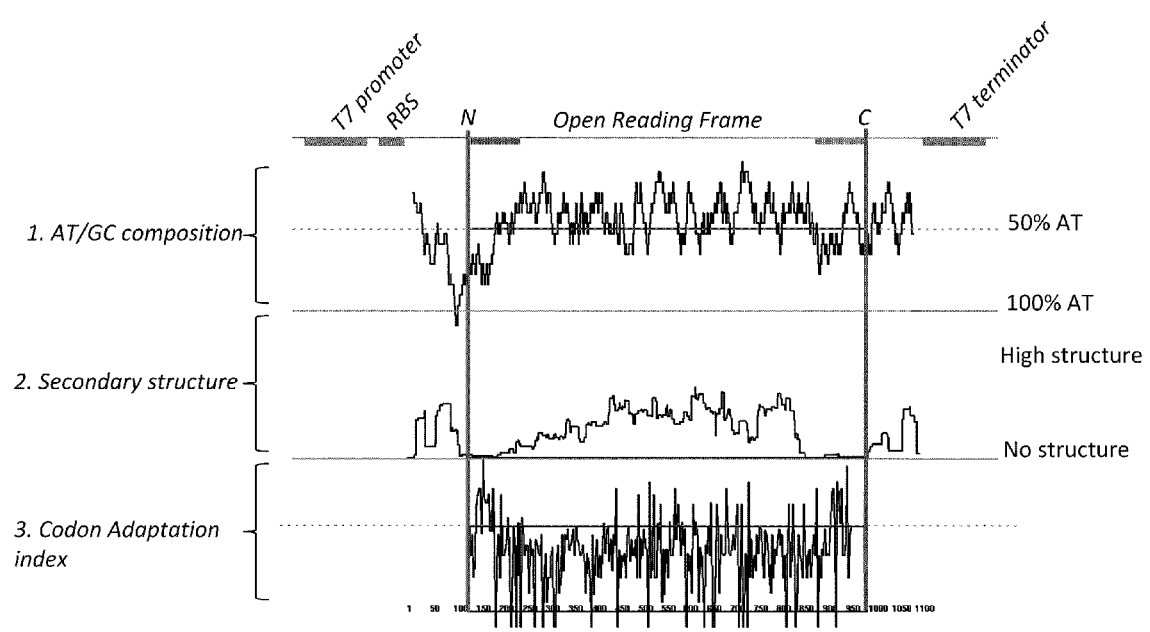
FIG. 4 shows the structure of the synthetic expression constructs, and the regions that are changed by the mRNA sequence design algorithm ORFOPT. The open reading frame is flanked by 5' and 3' untranslated regions containing the T7 promoter/translation initiation sequence and T7 terminator respectively. The 35-base terminal segments within the ORF are indicated in red and orange.

285 synthetic genes distributed over three proteins that varied in size, structure, origin, and heterologous expression levels of their wild-type ORF sequences were designed and constructed. These synthetic genes were constructed by automation methods using a robust PCR-mediated gene assembly scheme. See Example 1. Full-length linear PCR fragments containing synthetic ORFs flanked by constant control regions encoding a T7 promoter, ribosome binding site, and T7 terminator (see FIG. 4) were tested for protein expression using a coupled in vitro transcription and translation extract prepared from the *E. coli* BL21 Star strain. An in vitro expression approach to provide a standard, well-defined set of conditions was used. Furthermore, the BL21 Star strain lacked the C-terminal portion of RNase E (Lopez et. al, (1999)), thereby removing complexities associated with mRNA turnover (Carpousis, (2007)).

Figure 3:
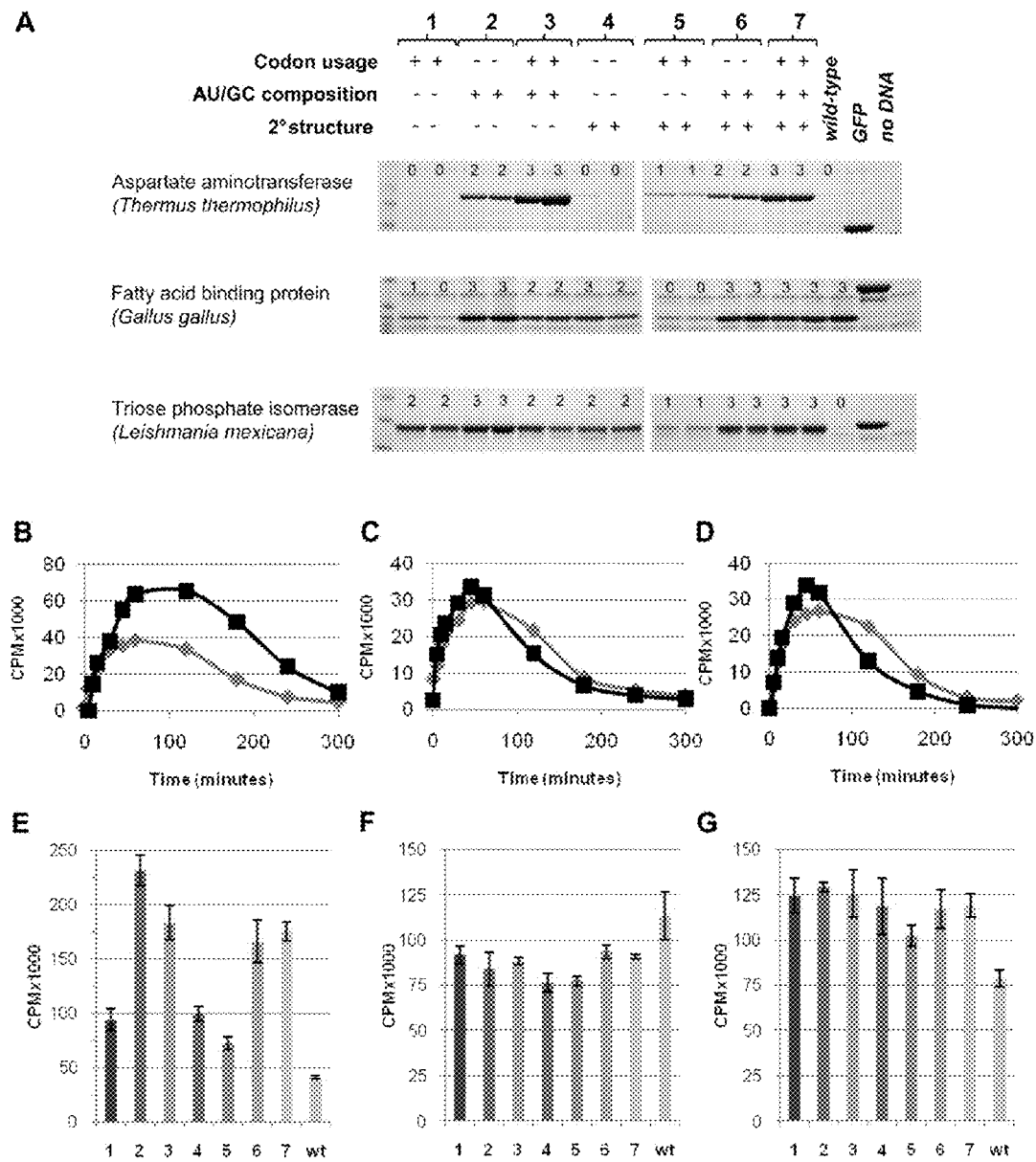
FIGS. 3A-G show the experimental expression levels of synthetic genes measured using *E. coli* coupled in vitro transcription and translation reactions.

Analysis of the 42 synthetic alleles shown in FIG. 3 was particularly illustrative. These alleles were designed using seven different optimization conditions in which their CAI, regional nucleotide composition, and mRNA secondary structure were optimized singly and in combination; the values of parameters that were not explicitly optimized were left unconstrained. The resulting seven conditions were tested in all three proteins and for each condition in vitro expression levels of two or three alleles differing by at least 10 isocodon changes were evaluated. For each condition, the expression pattern of two alleles differing by at least 10 mutations are shown in FIG. 3. Three proteins differing in size, structure, origin and expression of wild-type ORF sequences were used: *Thermus thermophilus* asparate aminotransferase (ttAST; ~43 kDa, (αβα)-sandwich, no expression), *Gallus gallus* fatty acid binding protein (ggFABP; ~15 kDa, β-clam, good expression), and *Leishmania mexicana* triose phosphate isomerase (lmTIM; ~28 kDa, $(\alpha\beta)_8$-barrel, poor-to-no expression). Proteins were purified from crude extract using immobilized metal affinity chromatography and run on SDS-PAGE gels (FIG. 3A). Green fluorescent protein was included as a positive control for protein expression. An extract without added DNA was a negative control. Observed expression levels were classified into one of four categories (numbers above gel lanes in FIG. 3: zero (no expression), one (weak expression), two (medium expression), three (high expression)). Time courses of radiolabeled RNA in reactions containing a high- (black) and low- (grey) expression level allele of ttAST (FIG. 3B), ggFABP (FIG. 3C) and lmTIM (FIG. 3D) were measured to determine the time point at which the highest level of newly synthesized mRNA was present, which was found to be at ~1 hour in each case. The amount of mRNA present in the alleles shown in FIG. 3A (one representative member per pair) was measured at 1 hour (FIG. 3E, ttAST; FIG. 3F, ggFABP; FIG. 3G, lmTIM).

Taken together these data clearly indicate that high levels of protein expression were achieved reliably in synthetic genes for which all parameters were optimized simultaneously. Taken together, the results show that expression levels were strongly influenced by high AU content in the N-terminal region, followed in importance by low secondary structure content. Optimization of the CAI by itself was ineffectual, but improved expression levels in the presence of the other two factors. Typically, the highest expression levels were obtained if all three factors were optimized simultaneously.

Figure 5:
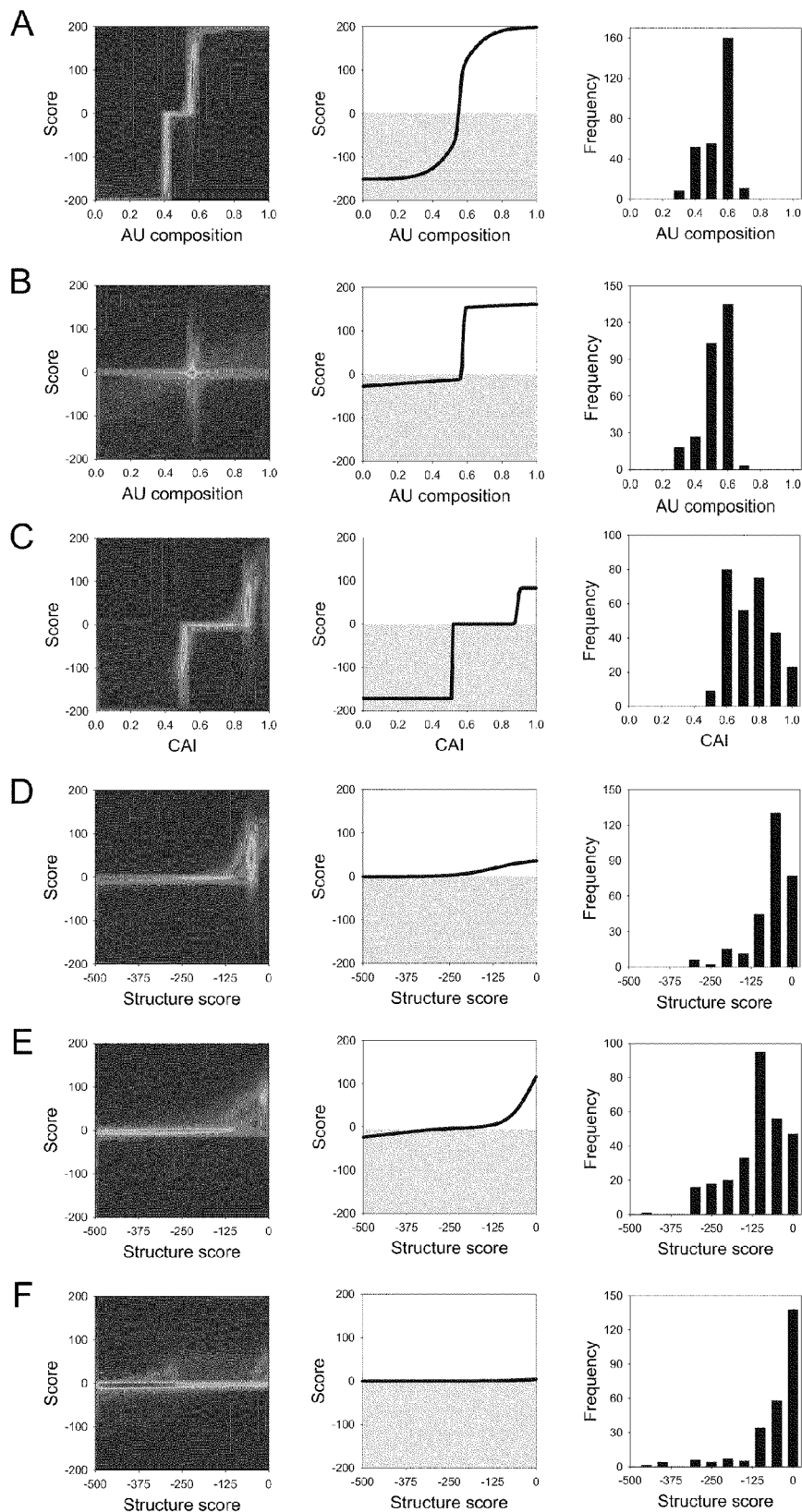
FIGS. 5A-F shows the construction of a mathematical function that calculates the experimentally observed protein expression levels from the mRNA nucleotide sequences.
Figure 6:
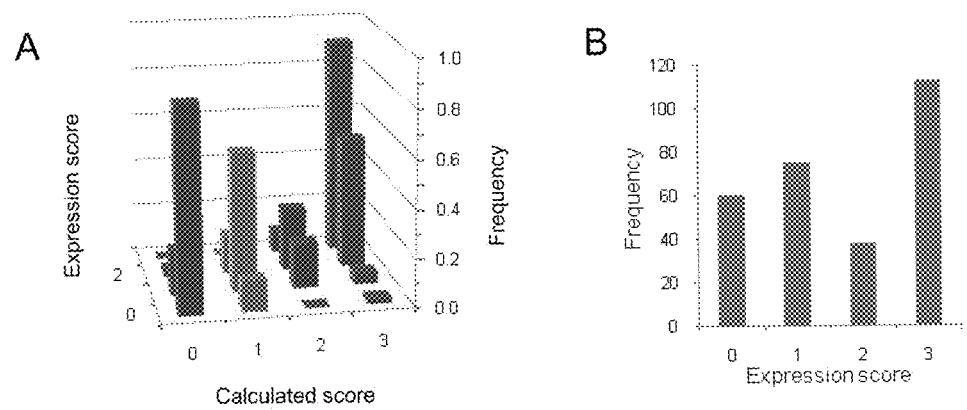
FIG. 6A shows the relative accuracy of the function linking mRNA nucleotide sequence to protein expression levels within each expression level category (frequency is normalized to 1 within each calculated score category). 69% of the four experimentally observed expression categories are fit perfectly, and the remainder to their closest neighboring category. The highest and lowest expression levels are fit most accurately.
FIG. 6B shows the distribution of observed expression level categories in the experimental dataset.

A further 243 synthetic genes were constructed to explore quantitative variation of these features in the three different regions of the ORFs (data not shown). The expression patterns of all synthetic genes were classified by inspection into four categories: zero (no expression), one (weak expression), two (medium expression), three (high expression) (FIG. 3A). With exception of the CAI, which was not sampled below 0.45, the resultant dataset provides reasonable sampling of the ORF features (FIG. 5, right column) and experimental outcomes (FIG. 6B), enabling the construction of an empirically parameterized mathematical function that predicts expression level from ORF nucleotide sequence: On analyzing the data, it was noticed that the observations could not be described using a linear combination of the ORF parameters, but appeared to behave as thresholds: if a feature fell below a threshold value it fully or partially inhibited expression, whereas if it was above the threshold, an increase in its value did not contribute much. Each of the six parameters (two regional nucleotide compositions, three regional secondary structure scores, and the CAI determined over the entire ORF) were represented as a sum of two sigmoidal curves corresponding to penalty and reward thresholds, respectively. See FIG. 5. The function was parameterized against the entire 285 synthetic gene dataset, using a simulated annealing algorithm with 10,000 independent optimization calculations. In addition to obtaining an optimal parameter set, this ensemble of solutions provided a Monte Carlo sampling of the fits (FIG. 5, left column). The resulting function predicted 69.2% of the four experimentally observed expression categories perfectly (FIG. 6A), and their remainder typically to their closest neighboring category. The highest and lowest expression levels were predicted the most accurately.

The fits reveal the relative contributions for each of the six parameters as described above. Any single parameter can adversely affect expression levels if it enters the penalty region of its threshold functions. Although the CAI was not nearly as dominant as might have been concluded from other studies, it can significantly enhance expression levels if high; conversely, if low, it was inhibitory although the precise numerical value of this latter effect was not yet well determined by the sampling.

The bioinformatic analysis revealed that canonical bacterial genes had strong regional biases in nucleotide composition and RNA secondary structure within the first and last ~35 bases of ORFs and that these features were unusually conserved regardless of overall genomic nucleotide composition. This analysis also revealed that genomic nucleotide composition and corresponding biases in amino acid composition were the main determinant of the average codon adaption index observed in genomes. The experimental analysis of expression levels of synthetic genes that were designed to vary these parameters showed that expression levels were strongly determined by nucleotide composition, especially in the N-terminal region.

Fits were obtained using a stochastic, simulated annealing algorithm with 10,000 independent optimization calculations. In addition to obtaining an optimal parameter set, this ensemble of solutions provided a Monte Carlo sampling of the error of the fits (FIG. 5, left column). The behavior of the distribution of parameter values gives an indication of how well these values were determined and the likely importance of their contribution to protein expression levels. The N-terminal AU composition (FIG. 5A) and secondary structure dependencies (FIG. 5D) were well determined. Composition contributes significantly above ~55% AU content and was strongly inhibitory below that value. Low secondary structure content was rewarded but high structure content was not strongly inhibitory. The C-terminal features were less well determined. The AU composition clearly has both a reward and a penalty contribution above and below ~57% respectively, but the numerical weight of these contributions remains ill determined. By contrast, C-terminal structure does not appear to play a significant role. Contributions of secondary structure in the middle region were fairly well determined. A very high structural content has a modest negative impact, near-absence of secondary structure was moderately favorable and in general the presence of secondary structure in this region was neutral. The contributions of the CAI for the whole ORF were qualitatively well determined, but uncertainty regarding the precise weight of penalty and reward remain. The CAI can significantly enhance expression levels if above ~0.8; conversely, if below ~0.5, it was inhibitory although the precise numerical value of this latter effect was not yet well determined by the sampling.

Figure 7:
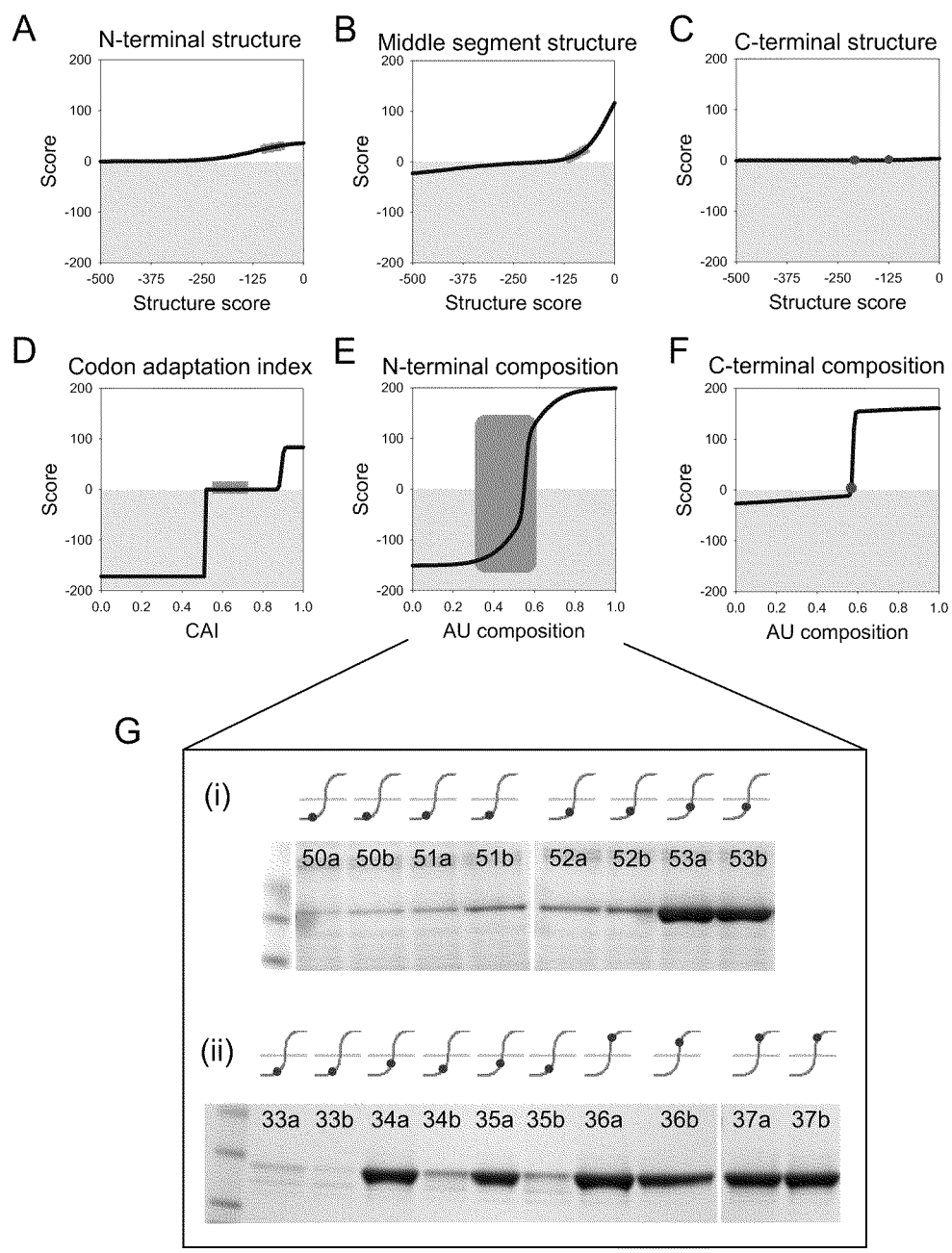
FIGS. 7A-G show the effect of varying N-terminal AU content in the presence of (near-) constant other parameters. Four pairs of alleles of ttAST (50a-53b; G(i)) and five allele pairs of lmTIM (33a-37b; G(ii)) were constructed in which the N-terminal composition was varied from 31% to 60% (FIG. 7E); while keeping the other five parameters near-constant in a range where they have little effect on the predicted expression score (FIGS. 7A-D, F).

The threshold effect for N-terminal AU composition was well illustrated by a series of alleles in which the N-terminal AU content was systematically varied while maintaining the other five parameters close to constant values. For the ttAST alleles 52a-53b and the lmTIM alleles 34a-35b (FIG. 7), there was a sudden increase in expression levels on transitioning from 48.6% to 54.3% (compare ttAST alleles 52a,b and 53a,b, lmTIM alleles 34a and 34b, or lmTIM 35a and 35b, as the composition transitions through the threshold. The four alleles lmTIM 36a-37b with 57.1% to 60.0% AU content illustrate that if the threshold was exceeded, there was not much apparent further gain in expression. Even with the use of computer algorithms, it was difficult to construct examples in the dataset for the other five features in which variation in one was cleanly separated from changes in the others, which illustrates how difficult if was to isolate the multifactorial contributions.

The contributions of the mRNA features analyzed in this study affect the three phases of translation efficiency: initiation, elongation, and termination (Bashan and Yonath, (2008); Ramakrishnan, (2002); Steitz, (2008)). Initiation involves the highly regulated loading of mRNA onto the ribosome (Marintchev and Wagner, (2004)). Similarly, termination is a carefully orchestrated process, involving recognition of the stop codon by release factors (Petry et al., (2008)). Without being limited by any particular mechanism or process, the correlation between lowered secondary structure in the N-terminal and C-terminal ORF regions and increased protein expression levels presumably arises from improved access as the mRNA was threaded onto the ribosome or accessory factors were loaded at initiation and termination, respectively. The origin of the correlation between protein expression and elevated AU content in these segments is less clear. Although a lowering of secondary structure stability may be directly contributory, this effect alone was unlikely to account for the observed threshold behavior of this feature. RNA helicases catalyze the unfolding of secondary structure and nucleotide composition could encode semi-specific recognition by such a helicase activity, giving rise to a threshold effect through a binding event. For instance, the DEAD-box protein superfamily includes prokaryotic RNA helicases that recognize AU-rich sequences (Rocak and Linder, (2004)), and in *E. coli* were involved in the RNA degradosome (Carpousis, (2007)), or ribosomal RNA maturation (Iost and Dreyfus, (2006)). Although DEAD boxes play a role in eukaryotic initiation of translation (Rocak and Linder, (2004)), no such function has been reported in prokaryotes. The ribosome itself contains an mRNA helicase activity that acts on a position within all bases from the codon that is being read (Takyar et al., (2005)). Although this activity appears largely independent of sequence, it was tempting to speculate that local nucleotide composition could influence it analogous to DEAD-box proteins. If this was the case, the patterns of nucleotide composition variance observed in all prokaryotes could reflect increased ribosomal helicase activity at the beginning and end of ORFs.

Translation and mRNA unwinding are tightly coupled in the elongation phase (Wen et al., (2008)), accounting for the observed boost in expression levels at low secondary structure content for the middle segment. The lack of penalty at intermediate structural content again may reflect RNA helicase activity. The CAI also affects the elongation phase as it tends to reflect the relative concentrations of available tRNA pool (Hershberg and Petrov, (2008)). In the TnT reactions, the tRNA pools clearly were different from the in vivo populations. Highly favorable CAI values have significant influence on protein expression levels. The lowering of the regional CAI in the N-terminal region of GC-rich bacteria presumably reflects the dominance of AU content over CAI at initiation, because in those genomes, AU-rich codons are less frequent and therefore have a lower CAI.

The development of a quantitative relationship between sequence and expression level should enable prediction of expression levels in natural ORFs and will enable the construction of synthetic genes optimized for heterologous protein expression. The equation accurately predicts high levels of protein expression. This capability enables the systematic design of highly expressed synthetic genes, as illustrated by the design of well-expressed genes for *Leishmana mexicana* triosephosphate isomerase and *Thermus thermophilus* asparate aminotransferase, of which the wild-type sequences express barely, if at all.

Example 5

Experimental Procedures for Picomole-Scale Characterization of Protein Stability Cell-Free Expression and Purification of Proteins Encoded by Synthetic Genes The wild-type proteins (SEQ ID NOs: 7-9) and cysteine variants were produced by cell-free in vitro transcription and translation (TnT) using an *E. coli* extract from BL21 Star (DE3) (Invitrogen; C6010-03) (Jewett et al., *Biotechnol. Bioeng.* 86:19-26 (2004)) programmed with a synthetic linear DNA fragment that was constructed using automated, PCR-mediated gene assembly (Cox et al., *Prot. Sci.* 16: 379-390 (2007)). The synthetic gene sequences contained a 5' T7-promoter, a 5' ribosome binding site, and a 3' T7-terminator flanking an open reading frame whose DNA sequence was optimized for protein expression using a computational algorithm that manipulates mRNA structure (see Examples 1 to 4, above). All proteins contain a C-terminal Flag-affinity tag (GGSDYKDDDDK) for purification. The sequence of ecRBP used in this study (SEQ ID NO:8) has the additional mutation T3W relative to the native sequence. Approximately 2 µg of DNA was added to 200 µL TnT extract and incubated at 30° C. for 2 hours. Proteins were purified using Flag-affinity beads (Sigma; F2426): beads were pre-blocked for 2 hours (Starting Block; Thermo Scientific; 37543), washed with TBS (25 mM Tris, 150 mM NaCl, pH 7.4). 100 µL of TnT extract was combined with 1 mL Flag beads (A600=0.25), incubated at 4° C. (15 min with end-over-end mixing), washed twice with 1 mL of TBS, and eluted with 3×-Flag peptide (Sigma; F4799) buffer (25 mM MOPS, 100 mM KCl, 150 µM 3×-Flag peptide, and pH 7.6). Purified proteins were used directly in QCR experiments.

QCR Experiment

Figure 8:
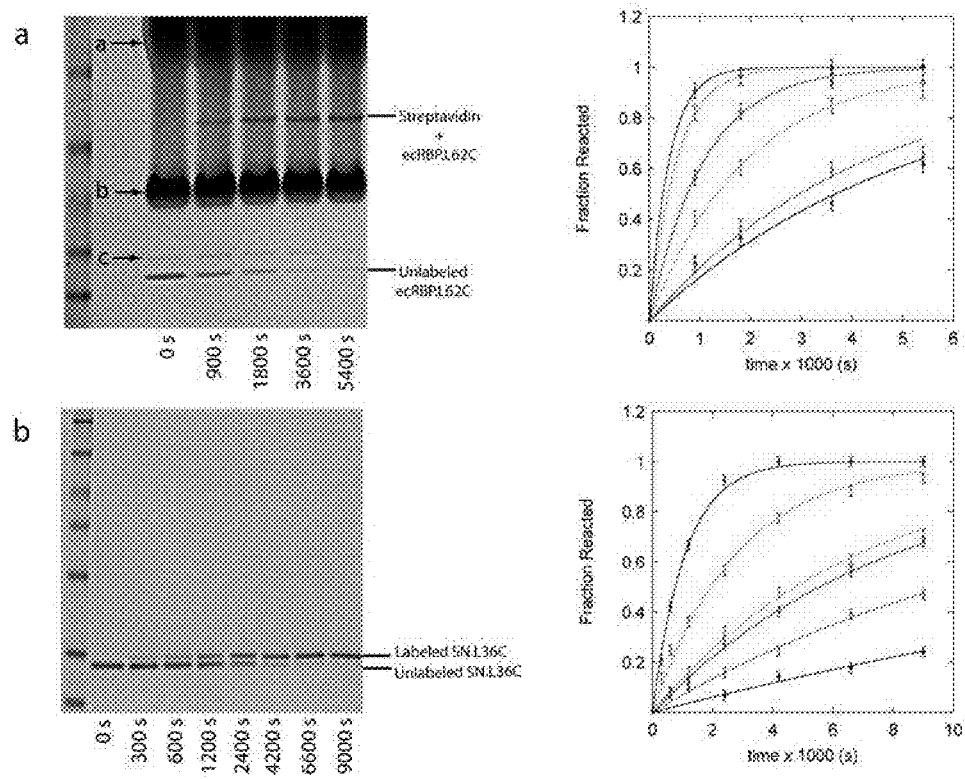
FIGS. 8A-B show representative Quantitative Cysteine Reactivity (QCR) experiments for *E. coli* ribose-binding protein (ecRBP; SEQ ID NO:8) and *Staphylococcal* nuclease (SN; SEQ ID NO:7).

The rate of labeling of internal cysteine residues was measured by reacting 30-50 µL of ~0.1 µM protein sample (i.e., ~3-5 picomoles of protein) with excess IAM-biotin (1 mM unless otherwise stated) at constant temperature (25 mM MOPS, 100 mM KCl and pH 7.6). 5 µL aliquots were removed at fixed time intervals and quenched by addition of 2 µL 2M β-mercaptoethanol (Sigma; M6250). Following addition of 5 µL LDS-buffer (Invitrogen; NP0007) and heating for 2 min at 85° C., (un)labeled protein species were resolved by SDS-PAGE (Novex 4-12% Bis-Tris Gels; Invitrogen; NP0321). Observed gel shifts of the biotinylated species were caused either by slight differences in conformation between the (un)labeled species (FIG. 8B) or, more typically, by addition of 4 µL of 40 mg/mL streptavidin (Pierce; 21125) after heating (FIG. 8A). For the experiment shown in FIG. 8A, ecRBP variant L62C was modified with 1 mM IAM-biotin at 47.1° C., pH 7.6. FIG. 8A, left panel, shows an SDS-PAGE of the modification over time, with the labeling times indicated for lanes 2-6. Streptavidin was used to alter the electrophoretic mobility of the labeled protein (Streptavidin bands indicated by a, b, and c). Unlabeled fractions were quantified by densitometry and fit with a single exponential to obtain reaction rates (right panel) at different temperatures (54.6° C., blue; 51.7° C., green; 48.9° C., red; 47.1° C., orange; 45.2° C., purple; 44.5° C., black); corresponding reaction rates were $2.6 \times 10^{-3}$, $1.9 \times 10^{-3}$, $9.3 \times 10^{-4}$, $5.2 \times 10^{-4}$, $2.6 \times 10^{-4}$, $2.0 \times 10^{-4}$ s$^{-1}$ respectively. Error bars represent the estimated uncertainty of the integrated band intensities (~2%). For the experiment shown in FIG. 8B, SN variant L36C was labeled with IAM-biotin at 35.3° C., pH 7.6. FIG. 8B, left panel panel, shows an SDS-PAGE of the modification over time, with the labeling times indicated. The (un)labeled forms migrate differently in the gel, enabling ratiometric quantification to obtain reaction rates (right panel) at different temperatures (38.3° C., blue; 35.3° C., green; 32.3° C., red; 29.3° C., orange; 26.3° C., purple; 23.3° C., black); corresponding reaction rates were $9.2 \times 10^{-4}$, $3.6 \times 10^{-4}$, $1.2 \times 10^{-4}$, $1.5 \times 10^{-4}$, $7.2 \times 10^{-5}$, $3.1 \times 10^{-5}$ s$^{-1}$ respectively. At 29.3° C., 26.3° C. and 23.3° C., $k_{int}$ and $k_{label}$ were manipulated by increasing the concentration of IAM-biotin from 1 mM to 3.16 mM.

Following staining with GelCode™ Blue Stain reagent (Thermo Scientific; 24592), gel images were digitized and band intensities quantified by densitometry (ImageJ; Rasband (1997-2009), U.S. National Institutes of Health, Bethesda, Md.) and fit to a single exponential to derive $k_{label}$. See Tables 11 and 12. When designing QCR experiments, consideration was given to the degradation of the iodoacetyl moiety of IAM-biotin, which was dependent on time, exposure to light, and temperature. At temperatures less than ~65° C., this effect to be negligible over the time-course of ~2 hours. At higher temperatures the degradation of IAM-biotin is taken into account, primarily by limiting the labeling reaction to less than ~90 min.

TABLE 11

Temperature dependence of $\Delta G_u$ for RBP and SN variants [

| Variant | [Ligand] µM | T ° C. | [IAM] [M] | $k_{int}$ s$^{-1}$ | $k_{ex}$ s$^{-1}$ |
|---|---|---|---|---|---|
| SN.F34C | 26.3 | 3.16E-03 | 2.82E-03 | 6.10E-05 | 2.3 |
| SN.F34C | 29.3 | 3.16E-03 | 3.69E-03 | 1.10E-04 | 2.1 |
| SN.F34C | 32.3 | 1.00E-03 | 1.53E-03 | 8.00E-05 | 1.8 |
| SN.F34C | 35.3 | 1.00E-03 | 1.98E-03 | 2.60E-04 | 1.2 |
| SN.F34C | 38.3 | 1.00E-03 | 2.55E-03 | 7.20E-04 | 0.6 |
| SN.F34C | 40.3 | 1.00E-03 | 3.02E-03 | 1.30E-03 | 0.2 |
| SN.L36C | 23.3 | 3.16E-03 | 2.14E-03 | 3.10E-05 | 2.5 |
| SN.L36C | 26.3 | 3.16E-03 | 2.82E-03 | 7.20E-05 | 2.2 |
| SN.L36C | 29.3 | 3.16E-03 | 3.70E-03 | 1.50E-04 | 1.9 |
| SN.L36C | 32.3 | 1.00E-03 | 1.53E-03 | 1.20E-04 | 1.5 |
| SN.L36C | 35.3 | 1.00E-03 | 1.98E-03 | 3.60E-04 | 0.9 |
| SN.L36C | 38.3 | 1.00E-03 | 2.55E-03 | 9.20E-04 | 0.4 |
| ecRBP.L62C | 44.5 | 1.00E-03 | 4.26E-03 | 2.00E-04 | 1.9 |
| ecRBP.L62C | 45.2 | 1.00E-03 | 4.50E-03 | 2.60E-04 | 1.8 |
| ecRBP.L62C | 47.1 | 1.00E-03 | 5.25E-03 | 5.20E-04 | 1.4 |
| ecRBP.L62C | 48.9 | 1.00E-03 | 6.05E-03 | 9.30E-04 | 1.1 |
| ecRBP.L62C | 51.7 | 1.00E-03 | 7.53E-03 | 1.90E-03 | EX1, 0.7 |
| ecRBP.L62C | 54.6 | 1.00E-03 | 9.19E-03 | 2.60E-03 | EX1, 0.6 |
| ecRBP.A188C | 45.2 | 1.00E-03 | 4.50E-03 | 1.10E-04 | 2.3 |
| ecRBP.A188C | 47.1 | 1.00E-03 | 5.25E-03 | 1.80E-04 | 2.1 |
| ecRBP.A188C | 48.9 | 1.00E-03 | 6.05E-03 | 5.10E-04 | 1.5 |
| ecRBP.A188C | 51.7 | 1.00E-03 | 7.53E-03 | 1.50E-03 | 0.9 |
| ecRBP.A188C | 54.6 | 1.00E-03 | 9.19E-03 | 3.70E-03 | 0.3 |

TABLE 12

Ligand dependence of $\Delta G_u$ for variants of SN (SEQ ID NO: 7), ecRBP (SEQ ID NO: 8) and ecMBP (SEQ ID NO: 9)

| Variant | [Ligand] µM | T ° C. | [IAM] [M] | $k_{int}$ s$^{-1}$ | $k_{ex}$ s$^{-1}$ | $\Delta G$ kcal mol$^{-1}$ | $\Delta\Delta G$ kcal mol$^{-1}$ |
|---|---|---|---|---|---|---|---|
| SN.F34C | 0 | 35.3 | 1.00E-03 | 1.98E-03 | 2.62E-04 | 1.2 | 0 |
| SN.F34C | 3 | 35.3 | 1.00E-03 | 1.98E-03 | 1.82E-04 | 1.4 | 0.3 |
| SN.F34C | 6 | 35.3 | 1.00E-03 | 1.98E-03 | 1.35E-04 | 1.6 | 0.5 |
| SN.F34C | 12 | 35.3 | 1.00E-03 | 1.98E-03 | 8.60E-05 | 1.9 | 0.7 |
| SN.F34C | 24 | 35.3 | 1.00E-03 | 1.98E-03 | 4.60E-05 | 2.3 | 1.1 |
| SN.L36C | 0 | 35.3 | 1.00E-03 | 1.98E-03 | 3.60E-04 | 0.9 | 0 |
| SN.L36C | 3 | 35.3 | 1.00E-03 | 1.98E-03 | 1.80E-04 | 1.4 | 0.5 |
| SN.L36C | 6 | 35.3 | 1.00E-03 | 1.98E-03 | 1.30E-04 | 1.6 | 0.7 |
| SN.L36C | 12 | 35.3 | 1.00E-03 | 1.98E-03 | 6.10E-05 | 2.1 | 1.2 |
| SN.L36C | 24 | 35.3 | 1.00E-03 | 1.98E-03 | 3.40E-05 | 2.5 | 1.6 |
| ecRBP.L62C | 0 | 48.9 | 1.00E-03 | 6.05E-03 | 9.90E-03 | 1.0 | 0 |
| ecRBP.L62C | 1.5 | 48.9 | 1.00E-03 | 6.05E-03 | 5.10E-03 | 1.5 | 0.5 |
| ecRBP.L62C | 3 | 48.9 | 1.00E-03 | 6.05E-03 | 3.60E-03 | 1.8 | 0.7 |
| ecRBP.L62C | 6 | 48.9 | 1.00E-03 | 6.05E-03 | 1.90E-04 | 2.2 | 1.2 |
| ecRBP.L62C | 12 | 48.9 | 1.00E-03 | 6.05E-03 | 1.10E-04 | 2.6 | 1.5 |
| ecRBP.L62C | 24 | 48.9 | 1.00E-03 | 6.05E-03 | 9.10E-04 | 2.7 | 1.6 |
| ecRBP.A188C | 0 | 54.6 | 1.00E-03 | 9.40E-03 | 2.17E-03 | 0.8 | 0 |
| ecRBP.A188C | 1.5 | 54.6 | 1.00E-03 | 9.40E-03 | 1.41E-03 | 1.1 | 0.3 |
| ecRBP.A188C | 3 | 54.6 | 1.00E-03 | 9.40E-03 | 9.70E-04 | 1.4 | 0.6 |
| ecRBP.A188C | 6 | 54.6 | 1.00E-03 | 9.40E-03 | 7.30E-04 | 1.6 | 0.8 |
| ecRBP.A188C | 12 | 54.6 | 1.00E-03 | 9.40E-03 | 3.20E-04 | 2.2 | 1.4 |
| ecRBP.A188C | 24 | 54.6 | 1.00E-03 | 9.40E-03 | 1.90E-04 | 2.5 | 1.7 |
| ecMBP.T157C | 0 | 63.3 | 1.00E-03 | 1.79E-02 | 5.10E-04 | 2.4 | 0 |
| ecMBP.T157C | 6 | 63.3 | 1.00E-03 | 1.79E-02 | 2.50E-04 | 2.9 | 0.5 |
| ecMBP.T157C | 12 | 63.3 | 1.00E-03 | 1.79E-02 | 1.80E-04 | 3.1 | 0.7 |
| ecMBP.T157C | 24 | 63.3 | 1.00E-03 | 1.79E-02 | 1.30E-04 | 3.3 | 0.9 |
| ecMBP.T157C | 48 | 63.3 | 1.00E-03 | 1.79E-02 | 9.10E-05 | 3.5 | 1.2 |
| ecMBP.S263C | 0 | 63.3 | 1.00E-03 | 1.79E-02 | 5.30E-04 | 2.3 | 0 |
| ecMBP.S263C | 6 | 63.3 | 1.00E-03 | 1.79E-02 | 3.50E-04 | 2.6 | 0.3 |
| ecMBP.S263C | 12 | 63.3 | 1.00E-03 | 1.79E-02 | 2.60E-04 | 2.8 | 0.5 |
| ecMBP.S263C | 24 | 63.3 | 1.00E-03 | 1.79E-02 | 1.60E-04 | 3.2 | 0.8 |
| ecMBP.S263C | 48 | 63.3 | 1.00E-03 | 1.79E-02 | 1.20E-04 | 3.4 | 1.0 |

Figure 9:
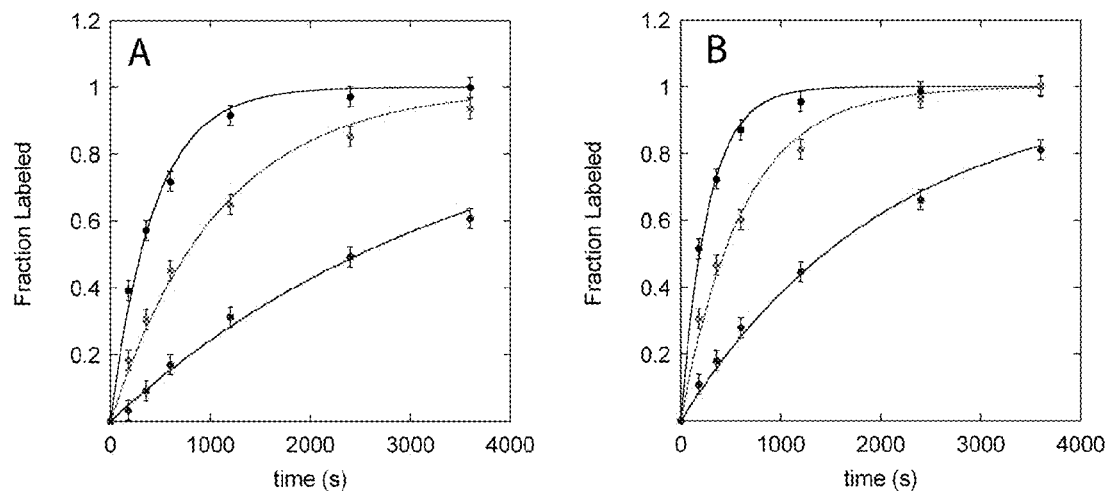
FIGS. 9A-B show an example of the EX1/EX2 limit. An illustrative test of EX2 conditions for SN variants F34C (SEQ ID NO:10) (FIG. 9A) and L36C (SEQ ID NO:11) (FIG. 9B) at 38.3° C. The change in observed rate constant for labeling of these protected cysteines is proportional to the change in concentration of IAM-biotin (black: 3 mM; lighter blue: 1.1 mM; darker blue: 0.3 mM). $k_{label}$ at 3, 1, and 0.3 mM IAM-biotin for Cys-34: $2.3 \times 10^{-3}$ s$^{-1}$, $9.2 \times 10^{-4}$ s$^{-1}$, and $2.8 \times 10^{-4}$ s$^{-1}$ respectively; for Cys-36: $3.7 \times 10^{-3}$ s$^{-1}$, $1.6 \times 10^{-4}$ s$^{-1}$, and $4.8 \times 10^{-4}$ s$^{-1}$ respectively.

The equation $$\Delta G_U = RT \ln\left(\frac{k_{int} - k_{label}}{k_{label}}\right) \quad [15]$$

applies only if the labeling conditions were fully in the EX2 limit, when $k_{close} \gg k_{int}$. As labeling reagent concentration increases, $k_{int}$ increases concomitantly and eventually $k_{int}$ will become equal to or greater than $k_{close}$. Under these conditions, the observed labeling rate was determined solely by $k_{open}$ and $k_{label}$ and was no longer a measure of stability. The reagent concentration and environmental conditions (i.e. pH and temperature) at which EX2 conditions no longer apply varies according to the (un)folding kinetics of the protein. A simple test of reaction mechanism was to change reagent concentration and remeasure the kinetics: EX2 conditions were satisfied if the change in the observed labeling rate was proportional to the change in reagent concentration (see FIG. 9).

Determining Intrinsic Reaction Rates of Unprotected Cysteines

Figure 10:
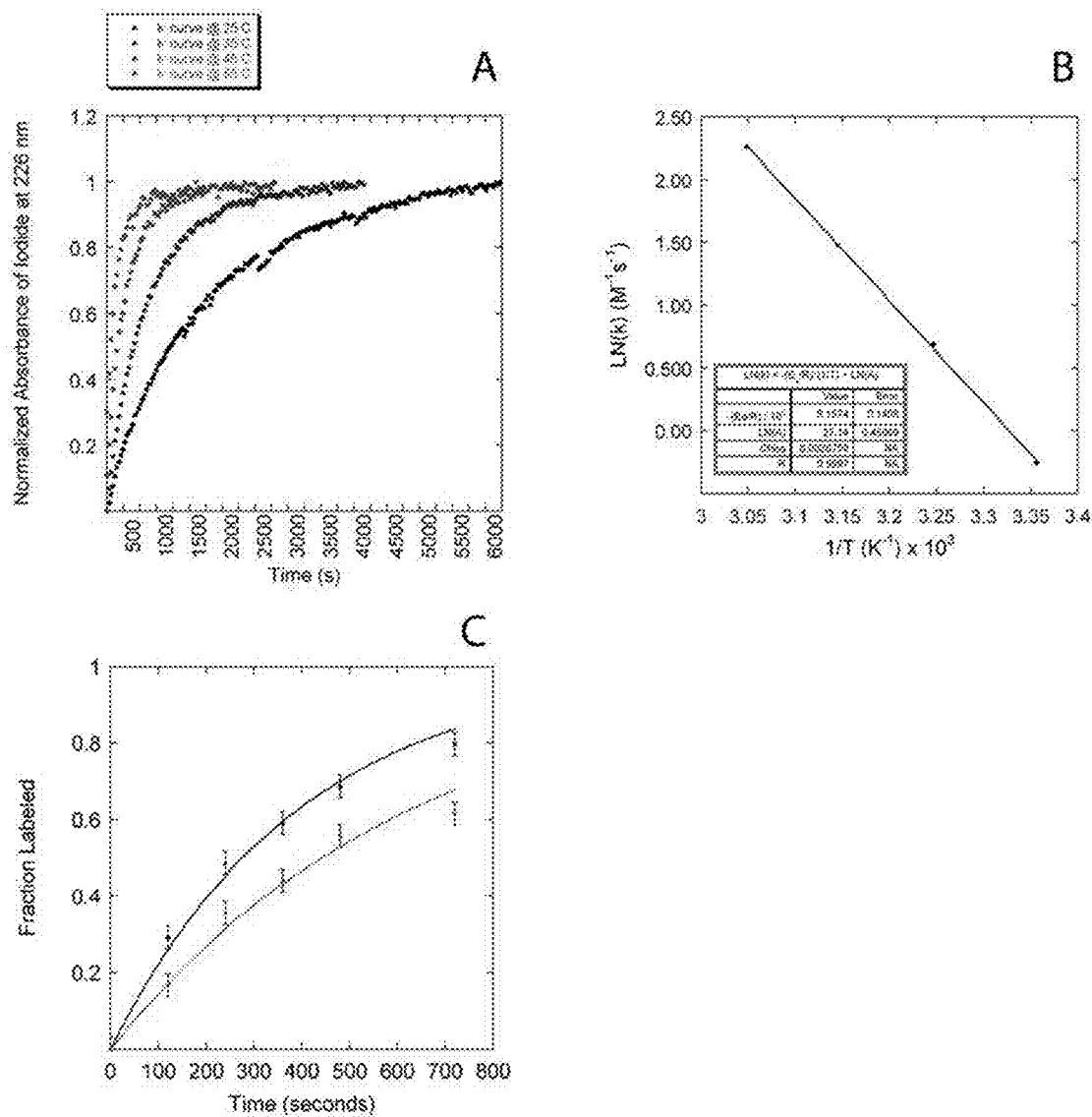
FIGS. 10A-C show the determination of $k_{int}$ in model compounds and unfolded SN.

The iodoacetyl moiety of IAM-biotin (EZ-Link™ Iodoacetyl-PEG2-Biotin; Pierce; 21334) reacts primarily with free thiolate to form a stable thioether bond. Because thiolate was the predominant reactive species, the reaction rate was dependent on the $pK_a$ of cysteine (~8.6) relative to solution pH (which was set to 7.6). The $k_{int}$ values reported here were only valid for pH 7.6. $k_{int}$ was determined for an unprotected cysteine by reacting IAM-biotin with L-glutathione (GSH) (Sigma; G4251) and monitoring the absorbance of the liberated iodide ion ($\epsilon_{226}$=12,600M$^{-1}$ cm$^{-1}$ at 226 nm) as function of time. Second-order rate constants for the reaction of IAM-biotin with GSH were measured under pseudo first-order conditions at 25° C., 35° C., 45° C. and 55° C. (80 µM IAM-biotin, 800 µM GSH, 25 mM MOPS, 100 mM KCl and pH 7.6) and analyzed in terms of the Arrhenius equation (see FIG. 10). The slope ($-E_a/R$) and pre-exponential factor (ln A) were found to be $-8.2 \times 10^3 \pm 0.1 \times 10^3$ and $27.1 \pm 0.5$ s$^{-1}$ respectively, enabling $k_{int}$ to be calculated at any temperature. $k_{int}$ values derived from unfolded proteins were in direct agreement with the GSH-derived $k_{int}$ values.

Example 6

Measuring Conformational Free Energies by QCR

Figure 11:
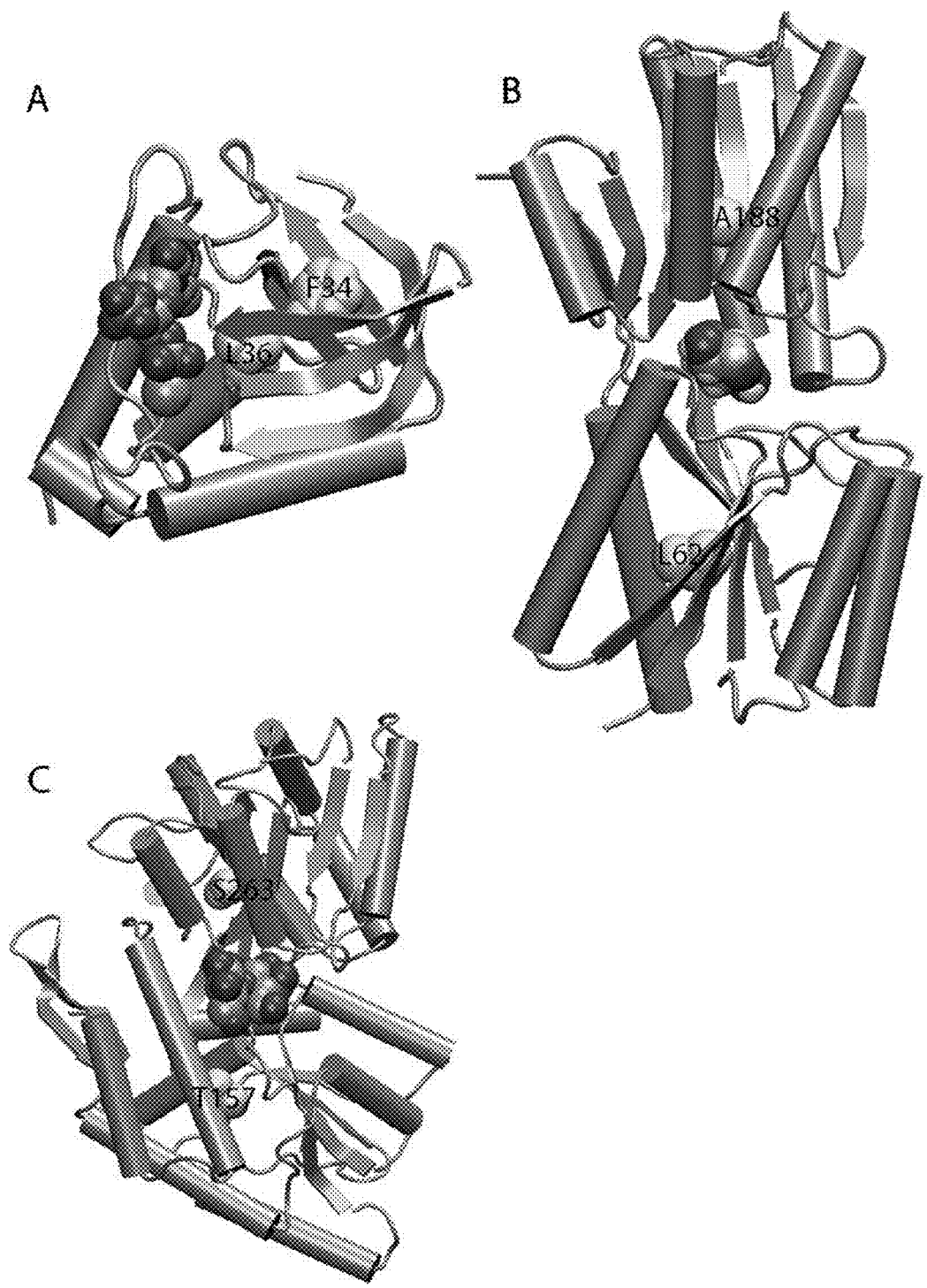
FIGS. 11A-C show the structural models for the substituted sites.

The QCR experiment was designed to determine the Gibbs free energy of global protein unfolding by measuring the reactivity of wild-type or mutant cysteines buried in a hydrophobic core. The QCR approach was demonstrated in three model proteins, SN (SEQ ID NO:7), ecRBP (SEQ ID NO:8) and ecMBP (SEQ ID NO:9) mutated to contain cysteine probes located in internal microenvironments that flank ligand-binding sites, but do not contact directly bound metals, inhibitors, or ligands (see FIG. 11). These mutant proteins were produced in 200 µL batches by cell-free coupled transcription and translation in *E. coli* extract. Following affinity purification, which typically yields 0.4 to 1 µg of protein, the reactivity of the buried cysteines was determined by timed end-point analysis experiments in which the modified protein species were separated by gel electrophoresis and quantified by densitometry. See FIG. 8 and Example 5. This approach uses approximately 0.5 picomoles (~10 nanograms) of protein per time point and can use a variety of thiol-reactive reagents that alter electrophoretic mobility or were highly fluorescent.

The QCR method exploits the conformational fluctuations of a protein to measure conformational free energy. Cysteines that were protected in the folded ensemble can be modified by thiol-reactive probe only by complete exposure to bulk solvent by transient unfolding reactions, as described by a two-step reaction scheme:

Unfolding free energies ($\Delta G_U$) can be determined under EX2 conditions ($k_{close} \gg k_{int}$) by measuring $k_{label}$, the rate constant for labeling a protected cysteine at a specified concentration of thiol probe [P]

$$k_{label} = \frac{k_{open} k_{int}}{(k_{open} + k_{close} + k_{int})} \quad [16]$$

$$\underset{EX2}{\cong} \frac{k_{open} k_{int}}{(k_{open} + k_{close})}$$

$$= \frac{k_{int}}{(1 + e^{\Delta G_U/RT})}$$

where $\Delta G_U$ was related to the closing and opening reaction as $\Delta G_U = RT \ln k_{close}/k_{open}$, and $k_{int}$ was the product of [P] and the biomolecular rate constant for the reaction of an unprotected cysteine ($k_{int}$=k[P]). Values for $k_{int}$ can be obtained from the reactivity of unprotected cysteine residues in model compounds or unfolded proteins for the accurate determination of $\Delta G_U$ (see Example 5). Rearrangement of equation 3 yields conformational free energy $$\Delta G_U = RT \ln\left(\frac{k_{int} - k_{label}}{k_{label}}\right) \quad [17]$$

Figure 12:
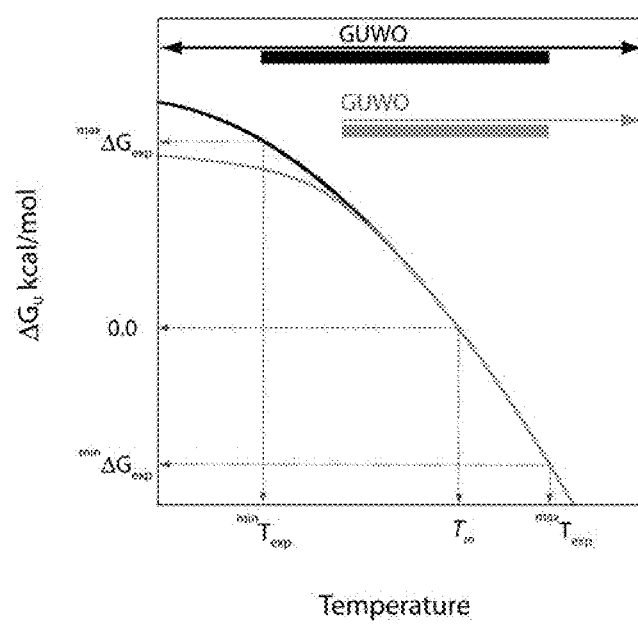
FIG. 12 shows the temperature range at which global unfolding free energies ($\Delta G_U$) can be determined by quantitative cysteine reactivity as determined by three factors.

A buried cysteine can be labeled as a result of local, subglobal or global unfolding transitions. The predominant mechanism of cysteine modification can be converted from local or partial unfolding to global unfolding by setting up conditions under which global stability was diminished (e.g. by addition of denaturation or by increasing temperature). The range of conditions under which access to global unfolding predominates was referred to as the global unfolding window of observation (GUWO). To ensure that the buried cysteines report global free energies (i.e. $\Delta G_U$), QCR experiments were always performed within a GUWO. Temperature was chosen to access the GUWO and measure global unfolding free energies as a function of temperature ($\Delta G_U(T)$), described by the Gibbs-Helmholtz relationship $$\Delta G_U(T) = \Delta H_m\left(1 - \frac{T}{T_m}\right) - \Delta C_p\left((T_m - T) + T\ln\frac{T}{T_m}\right) \quad [18]$$

where $T_m$ was the midpoint of thermal denaturation, $\Delta H_m$ the enthalpy of unfolding, and $\Delta C_p$ the change in heat capacity of unfolding. The temperature range over which observations can be made was determined by the limits where differences between $k_{label}$ and $k_{int}$ exceed experimental error, EX2 conditions prevailed, and the GUWO was present. See FIG. 12. The first limits were set by the accuracy of the measurement of the labeling rate constants: an upper limit occurs at a temperature ($maxT_{exp}$) and free energy ($min\Delta G_{exp}$) ~10° C. above $T_m$ (red-dashed arrows) where the difference of $k_{label}$ and $k_{int}$ was within experimental error; a lower limit occurs at a temperature ($minT_{exp}$) and free energy ($max\Delta G_{exp}$) ~10-20° C. below $T_m$, (greendashed arrows) where increased stability sufficiently reduces $k_{label}$ (eqs. 16 and 17) such that it appears to be independent of temperature within experimental error. The second limit was set in some cases where the mechanism of cysteine protection (i.e. local or global unfolding) was dependent on temperature. Such cases were manifested as a deviation of the observed temperature dependence of $\Delta G_U$ from that expected for global unfolding. Global unfolding conditions prevail within ~10-20° C. of $T_m$, which was referred to as the global unfolding window of observation (GUWO). The black line illustrates a case in which there was no such switch (modeled by eq. 18), and its GUWO extends over the entire temperature range; the grey line represents switching between global and local unfolding with a concomitant temperature limit for the GUWO (modeled by eq. 4 of Bai et al., Proteins 20(1):4-14 (1994)). The third limit was set at a point where EX1 conditions prevail and $k_{close}$ no longer exceeds $k_{int}$ (not illustrated). This may occur as stability was diminished ($\Delta G_U$<1 kcal/mol) or if the concentration of thiol probe [P] was too high. Loss of EX2 conditions was manifested as a loss of the linear dependence of $k_{label}$ on [P] and can be remedied by reducing [P]. The overall temperature range at which observations can be made was the intersection of all three of these conditions (black and gray bars). This temperature range covered a small portion of a Gibbs-Helmholtz curve. Consequently, values for $\Delta H_m$ and $\Delta C_p$ derived from a fit of the temperature dependence of $\Delta G_U$ were usually underdetermined, and values for $\Delta C_p$ were assigned a priori to derive reasonable estimates for $\Delta H_m$ and $T_m$ from stabilities measured within the GUWO.

Figure 13:
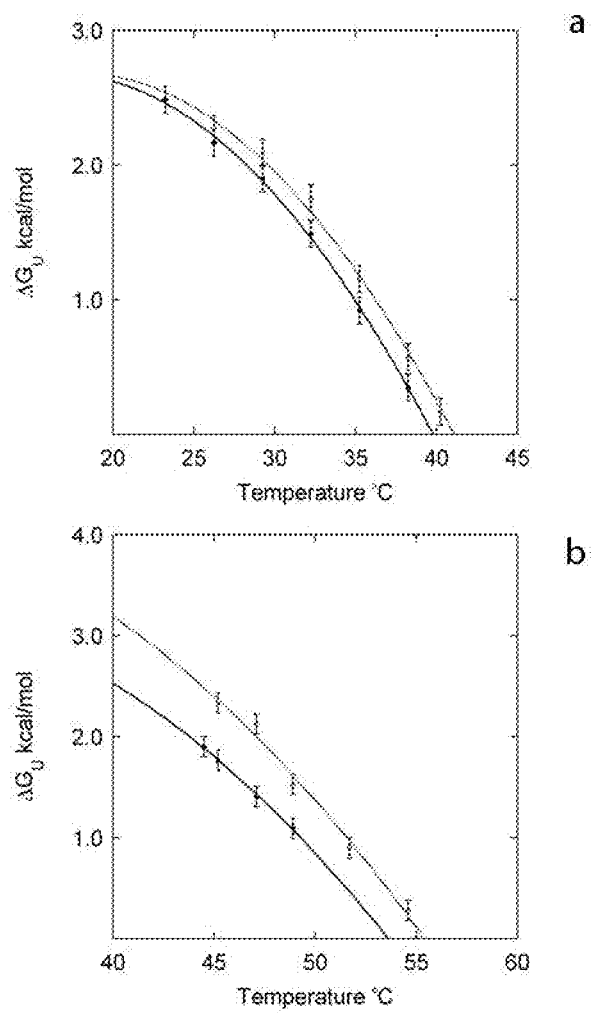
FIGS. 13A-B show the temperature dependence of $\Delta G_U$ determined by QCR for SN variants F34C (purple) and L36C (black) (FIG. 13A), and ecRBP variants L62C (purple) and A188C (SEQ ID NO:13) (black) (FIG. 13B). Solid lines indicate a fit to a Gibbs-Helmholtz profile (Eq. 18). Error bars represent the error of three independent experiments at select temperatures.

Using a total of only ~12.5 picomoles of protein (~2.5 picomoles or ~50 nanograms per temperature point), Gibbs-Helmholtz profiles were determined for two cysteine mutants of SN and ecRBP. See FIG. 13. Derived values for $\Delta H_m$ and $T_m$ were relatively insensitive to $\Delta C_p$ values within the range of 2-5 kcal mol$^{-1}$ K$^{-1}$, which was consistent with previous experimentally determined values for proteins in general (see Gomez et al., Proteins 22: 404-412 (1995); Razvi et al., Prot. Sci. 15:1569-1578 (2006); and Rees et al., Prot. Sci. 10: 1187-1194 (2001)). All four cysteine mutants were thermally destabilized: the apparent $T_m$ values of SN variants F34C (40±1° C.) and L36C (39±1° C.) were ~13.0° C. below wild-type (53.0° C.) (Talla-Singh et al., Proteins 71: 1607-1616 (2008)); the apparent $T_m$ values of ecRBP variants L62C (54±1° C.) and A188C were ~8° C. below wild-type (62.6° C.) (Prajapati et al., Biochemistry 46: 10339-10352 (2007)). The extrapolated $\Delta G°_U$ at 20° C. for SN mutants F34C and L36C, using $\Delta H_m$ values of 72±1 and 71±1 kcal mol$^{-1}$ respectively, was 2.7±0.1 kcal mol$^{-1}$ and 2.6 ±0.1 kcal mol$^{-1}$, whereas the stability of wild-type SN reported by chemical denaturation was 5.5±0.1 kcal mol$^{-1}$ (Green et al., Biochemistry 31: 5717-5728 (1992)). Similarly, the $\Delta G°_U$ at 25° C. for ecRBP mutants L62C and A188C, using $\Delta H_m$ values of 81±2 and 91±4 kcal mol$^{-1}$ respectively, was 3.2±0.1 kcal mol$^{-1}$ and 4.1±0.1 kcal mol$^{-1}$, whereas the stability of wild-type reported by chemical denaturation was 5.9±0.4 kcal mol$^{-1}$ (Prajapati et al., (2007) Proteins 66: 480-491). This decrease in stability caused by the introduction of cysteine was typical for mutations in the hydrophobic core of these and other proteins. See, e.g., Green et al.,) Biochemistry 31: 5717-5728 (1992; Kim et al., J. Prot. Chem. 15: 731-736 (1996); Bava et al., Nucleic Acids Res. 32: D120-D121 (2004).

Example 7

Measuring Ligand Affinity by Linkage Analysis of Protein Stability

The modulation of protein stability by binding of metals, ligands, activators, inhibitors, substrates, nucleic acid or other proteins can be used to measure binding affinities within a GUWO. For a protein with a single binding site, the free energy of ligand binding was described by $$\Delta G°_{bind} = RT\ln P = RT\ln\left(1 + \frac{[L]}{K_D}\right) \quad [19]$$

where P was the binding polynomial, [L] the total ligand concentration, and $K_D$ the apparent dissociation constant of the ligand. For proteins with multiple ligand-binding sites, P was expanded as described in Equations 21-36 below.

Equations that Describe the Effects of Multiple Ligand Binding

For a macromolecule with a single binding site, the relative concentrations of unliganded and liganded species was described by the binding polynomial $$P = \left(1 + \frac{[L]}{K_D}\right) \quad [21]$$

The expression for a single-site binding isotherm was derived from the differentiation of ln(P) with respect to ln(L) using the chain-rule $$\bar{X} = \frac{d\ln P}{d\ln L} = \frac{d\ln P}{dP} \cdot \frac{dP}{dL} \cdot \frac{dL}{d\ln L} = \frac{K_A[L]}{1 + K_A[L]} = \frac{\frac{[L]}{K_D}}{1 + \frac{[L]}{K_D}} \quad [22]$$

where X bar was the number of moles of ligand bound per mole of macromolecule and $K_A$ and $K_D$ were the relevant equilibrium constants for the law of mass action $$M + L \rightleftharpoons ML; \quad K_A = \frac{[ML]}{[M][L]}; \quad K_A = \frac{1}{K_D} \quad [23, 24, 25]$$

X bar expressed in differential form provides the conceptual link between a ligand-binding isotherm and the free energy of ligand binding ($\Delta G_{bind}$); the area underneath a plot of X bar versus ln(L) was proportional to the free energy of binding. $\Delta G_{bind}$ was obtained by integrating the area under the binding isotherm (i.e. by integrating Equation 22) and multiplying by the proportionality constant RT $$\Delta G_{bind} = RT\int \bar{X} \, d\ln L = RT\int d\ln P = RT \ln P + \Delta G_{ref} \quad [26]$$

where $\Delta G_{ref}$ was the reference free energy of the macromolecule in the absence of ligand. In the specific case of a single binding site, Equation 26 was expressed as $$\Delta G_{bind} = RT \ln P = RT \ln\left(1 + \frac{[L]}{K_D}\right) + \Delta G_{ref} \quad [27]$$

In cases where a macromolecule binds more than one ligand the expression for $\Delta G_{bind}$ was more complex. Consider for example the binding of $Ca^{2+}$ and pdTP (a nucleotide inhibitor) to the enzyme Staphylococcal nuclease (SN). Reaction schemes 28 thru 33 describe the formation of the relevant binary and ternary complexes of an enzyme (E) combined with ligands A ($Ca^{2+}$) and B (pdTP).

$$E + A \rightleftarrows EA; \quad K_1 = \frac{[EA]}{[E][A]}; \quad K_1 = 90 \; \mu M \quad [28]$$

$$E + B \rightleftarrows EB; \quad K_2 = \frac{[EB]}{[E][B]}; \quad K_2 = 500 \; \mu M \quad [29]$$

$$EA + B \rightleftarrows EAB; \quad K_3 = \frac{[EAB]}{[EA][B]}; \quad K_3 = 20 \; \mu M \quad [30]$$

$$EB + A \rightleftarrows EAB; \quad K_4 = \frac{[EAB]}{[EB][A]}; \quad K_4 = 2.5 \; \mu M \quad [31]$$

$$E + AB \rightleftarrows EAB; \quad K_5 = \frac{[EAB]}{[E][AB]}; \quad K_5 = 2.2 \; \mu M \quad [32]$$

$$A + B \rightleftarrows AB; \quad K_6 = \frac{[AB]}{[A][B]} \quad [33]$$

The binding of $Ca^{2+}$ and pdTP to SN was fully described by $$P = 1 + \frac{[A]}{K_1} + \frac{[B]}{K_2} + \frac{[A][B]}{K_1 K_3} + \frac{[B][A]}{K_2 K_4} + \frac{[AB]}{K_5} \quad [34]$$

and $\Delta G_{bind}$ was described by $$\Delta G_{bind} = RT \ln\left(1 + \frac{[A]}{K_1} + \frac{[B]}{K_2} + \frac{[A][B]}{K_1 K_3} + \frac{[B][A]}{K_2 K_4} + \frac{[AB]}{K_5}\right) + \Delta G_{ref} \quad [35]$$

It has been shown that $Ca^{2+}$ and pdTP bind synergistically to SN. Consequently, the dissociation constant $K_5$ can be determined independent of the dissociation constants $K_1$, $K_2$, $K_3$ and $K_4$ by measuring the ligand binding energetics of SN at concentrations of $[AB]$ below $K_1$, $K_2$, and $K_3$ (i.e., 3 to 24 $\mu M$). This approach simplifies Equation 35 considerably $$\Delta G_{bind} = RT \ln\left(1 + \frac{[AB]}{K_5}\right) \quad [36]$$

By thermodynamic linkage, any change in $\Delta G_U$ caused predominantly by ligand binding (Scheme 1) is $$\Delta G_{bind} = \Delta \Delta^L G_U = \Delta^L G_U - \Delta^{apo} G_U \quad [20]$$

where $\Delta^L G_U$ and $\Delta^{apo} G_U$ were the stability of the protein in the presence of absence of ligand respectively. Equation 20 was used to obtain apparent $K_D$ values from either the ligand dependence of $\Delta \Delta G_U$ (by curve fitting), or from a single measurement of $\Delta \Delta G_U$.

Figure 14:
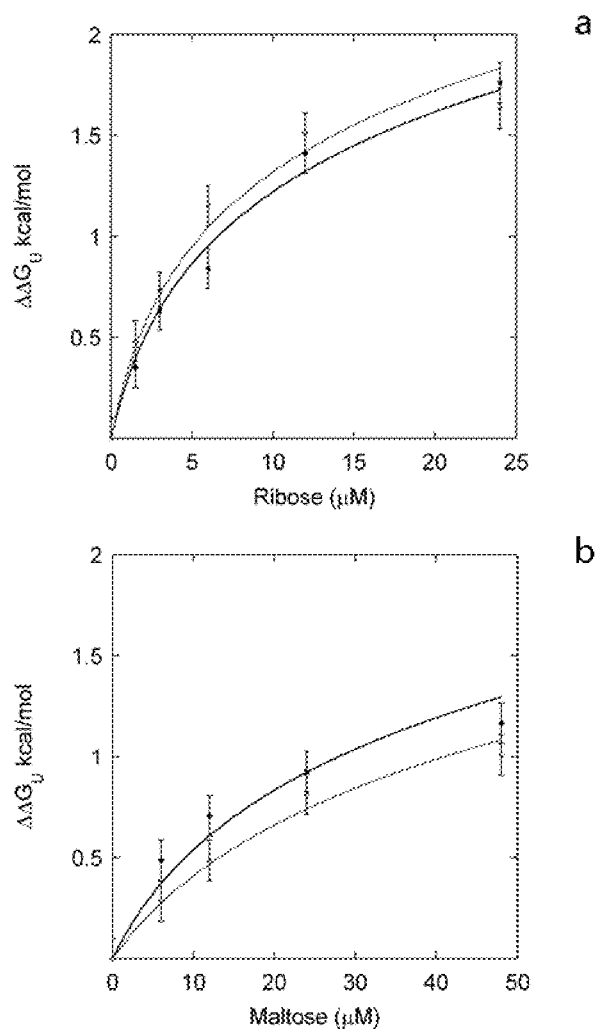
FIGS. 14A-B show the ligand concentration dependence of $\Delta\Delta G_U$ for ecRBP variants L62C (purple) at 48.9° C. and A188C (black) at 54.3° C.

Both ecRBP and ecMBP had a single ligand-binding site located within the interface between their N-terminal and C-terminal domains. With ~10 picomoles (~200 nanograms) of protein, binding affinities were determined by QCR experiments using two independent cysteine reporters introduced into each domain. ecRBP variants L62C (N-terminal domain) and A188C (C-terminal domain) reported ribose-binding affinities of 2.8±0.2 $\mu M$ (at 48.9° C.) and 1.8±0.1 $\mu M$ (at 54.3° C.) respectively (FIG. 14A); ecMBP variants T157C (C-terminal domain) and S263C (N-terminal domain) reported maltosebinding affinities of 8.0±0.2 $\mu M$ and 11.8±0.8 $\mu M$ respectively at 63.3° C. (FIG. 14B).

Figure 15:
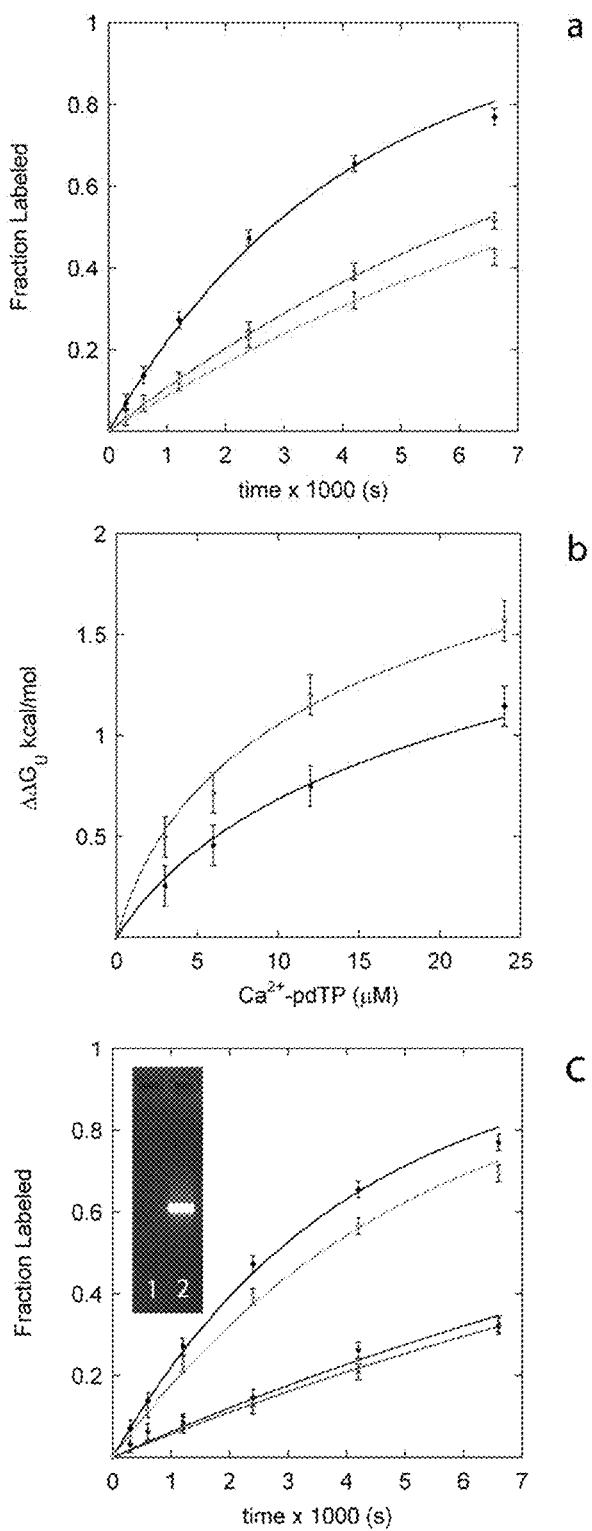
FIGS. 15A-C show the effect of ligands and substrate on SN stability.

Proteins that bind more than one ligand, either independently or synergistically, have a more complex free energy landscape that involves a number of different ligand bound species. QCR was used to characterize the binding of a calcium ion ($Ca^{2+}$) and a 5'-monophosphate inhibitor (pdTp) to SN. By themselves, $Ca^{2+}$ and pdTp bind to SN with affinities of ~500 $\mu M$ and $\mu$90 $\mu M$ (Serpersu et al., *Biochemistry* 25: 68-77 (1986)). Using ~5 picomoles (~100 nanograms) of protein, the $K_D$ values of each binary complex was determined by QCR. See FIG. 15A. SN variant L36C was incubated in the absence (black) and presence of 1 mM $Ca^{2+}$ (purple) or 50 $\mu M$ pdTp (orange) at 35.3° C. Observed $k_{label}$ of $3.0 \times 10^{-4}$, $1.2 \times 10^{-4}$, $9.2 \times 10^{-5}$ $s^{-1}$ respectively correspond to an increase in stability ($\Delta \Delta G_U$) of SN/L36C in the presence of 1 mM $Ca^{2+}$ or 50 $\mu M$ pdTp of 0.6±0.2 and 0.7±0.2 kcal $mol^{-1}$, which corresponds to apparent $K_D$ values of 600±200 $\mu M$ and 23±4 $\mu M$ respectively. Binding of $Ca^{2+}$ and pdTp was synergistic, as each exhibits a greater affinity (~2 $\mu M$) for SN in the presence of the other. Consequently, a 2:1 molar solution of $Ca^{2+}$:pdTp can be treated thermodynamically as a single, binary ligand $Ca^{2+}$-pdTp. Using ~10 picomoles (~200 nanograms) of protein, the affinity of $Ca^{2+}$-pdTp for SN variants F34C and L36C was determined to be 4.8±0.2 $\mu M$ and 2.2±0.1 $\mu M$ respectively at 35.3° C. See FIG. 15B.

Example 8

Inferring Enzyme Activity by QCR

Binding of substrates and products also affected enzyme stability in a detectable manner. QCR therefore provided a means to infer enzymatic activity within a GUWO using picomole quantities of protein without having to devise a reaction-specific kinetic assay. SN, a 5'-phosphodiesterase that hydrolizes single-stranded and double-stranded DNA and RNA was used to demonstrate this aspect. It selectively cleaves the phosphodiester bond between the phosphate and 5'-hydroxyl, producing short 3'-derived oligonucleotides (which do not bind to SN) and 5'-derived mononucleotides (which bind to and inhibit SN) (Cuatrecasas et al., *J. Biol. Chem.* 242: 1541-1547 (1967)). In the absence of calcium, SN was inactive and the binding of substrate alone can be measured by QCR. Addition of 4.7 $\mu M$ substrate DNA in the absence of calcium produces no observable effect on the stability reported by Cys-36. See FIG. 15A. SN variant L36C was incubated at 35.3° C. in the absence of substrate (black) and 4.7 $\mu M$ single-stranded DNA (green), 4.7 $\mu M$ single-stranded DNA with 1 mM $Ca^{2+}$ (blue), and 12 $\mu M$ of a 2:1 molar ratio of $Ca^{2+}$ and pdTp (red). See FIG. 15C. Observed $k_{label}$ of $3.0 \times 10^{-4}$, $2.8 \times 10^{-4}$, $7.5 \times 10^{-5}$ and $5.9 \times 10^{-5}$ $s^{-1}$ respectively correspond to $\Delta \Delta G_U$ values of 0.1±0.2, 0.9±0.2, and 1.0±0.2 kcal $mol^{-1}$. Following addition of 1 mM calcium, the substrate DNA was rapidly degraded. See FIG. 15C, inset. The L36C mutant was enzymatically active (inset; 1% agarose gel): 1.5 kb double-stranded DNA fragment (lane 2) digested completely (lane 1) by incubation with 0.05 μM SN/F34C at 20° C. for 10 min in a buffer of 1 mM $Ca^{2+}$, 25 mM MOPS, 100 mM KCl and pH 7.6. The QCR-determined stability of SN/L36C was increased by 0.9±0.1 kcal $mol^{-1}$, corresponding to an apparent binding affinity of 1.4±0.4 μM, which was nearly identical to the affinity of the inhibitor pdTp in the presence of 1 mM $Ca^{2+}$, and therefore was presumably due to the effect of product binding.

REFERENCES

Ahn, J. H., Chu, H. S., Kim, T. W., Oh, I. S., Choi, C. Y., Hahn, G. H., Park, C. G., and Kim, D. M. (2005). Cell-free synthesis of recombinant proteins from PCR-amplified genes at a comparable productivity to that of plasmid-based reactions. Biochem. Biophys. Res. Commun. 338, 1346-1352.

Caruthers, M. H., Barone, A. D., Beaucage, S. L., Dodds, D. R., Fisher, E. F., McBride, L. J., Matteucci, M., Stabinsky, Z., and Tang, J. Y. (1987). Chemical synthesis of deoxyoligonucleotides by the phosphoramidite method. Methods Enzymol. 154, 287-313.

Caruthers, M. H., Beaucage, S. L., Becker, C., Efcavitch, J. W., Fisher, E. F., Galluppi, G., Goldman, R., deHaseth, P., Matteucci, M., McBride, L., et al., (1983). Deoxyoligonucleotide synthesis via the phosphoramidite method. Gene Amplif. Anal. 3, 1-26.

Chamberlin, M., McGrath, J., and Waskell, L. (1970). New RNA polymerase from *Escherichia coli* infected with bacteriophage T7. Nature 228, 227-231.

Cox, J. C., Lape, J., Sayed, M. A., and Hellinga, H. W. (2007). Protein fabrication automation. Protein Sci. 16, 379-390.

Curry, K. A., and Tomich, C. S. (1988). Effect of ribosome binding site on gene expression in *Escherichia coli*. DNA 7, 173-179.

Davanloo, P., Rosenberg, A. H., Dunn, J. J., and Studier, F. W. (1984). Cloning and expression of the gene for bacteriophage T7 RNA polymerase. Proc. Natl. Acad. Sci. USA 81, 2035-2039.

Gao, X., Yo, P., Keith, A., Ragan, T. J., and Harris, T. K. (2003). Thermodynamically balanced inside-out (TBIO) PCR-based gene synthesis: a novel method of primer design for high-fidelity assembly of longer gene sequences. Nucleic Acids Res. 31, e143.

Hahn, G. H., and Kim, D. M. (2006). Production of milligram quantities of recombinant proteins from PCR-amplified DNAs in a continuous-exchange cell-free protein synthesis system. Anal. Biochem. 355, 151-153.

Horton, R. M., Hunt, H. D., Ho, S. N., Pullen, J. K., and Pease, L. R. (1989). Engineering hybrid genes without the use of restriction enzymes: gene splicing by overlap extension. Gene 77, 61-68.

Jewett, M. C., and Swartz, J. R. (2004a). Mimicking the Escherichia coli cytoplasmic environment activates long-lived and efficient cell-free protein synthesis. Biotechnol. Bioeng. 86, 19-26.

Jewett, M. C., and Swartz, J. R. (2004b). Rapid expression and purification of 100 nmol quantities of active protein using cell-free protein synthesis. Biotechnol. Prog. 20, 102-109.

Jewett, M. C., and Swartz, J. R. (2004c). Substrate replenishment extends protein synthesis with an in vitro translation system designed to mimic the cytoplasm. Biotechnol. Bioeng. 87, 465-472.

Kawarasaki, Y., Kawai, T., Nakano, H., and Yamane, T. (1995). A long-lived batch reaction system of cell-free protein synthesis. Anal. Biochem. 226, 320-324.

Kido, M., Yamanaka, K., Mitani, T., Niki, H., Ogura, T., and Hiraga, S. (1996). RNase E polypeptides lacking a carboxyl-terminal half suppress a mukB mutation in *Escherichia coli*. J. Bacteriol. 178, 3917-3925.

Kim, D. M., and Swartz, J. R. (2001). Regeneration of adenosine triphosphate from glycolytic intermediates for cell-free protein synthesis. Biotechnol. Bioeng. 74, 309-316.

Kim, R. G., and Choi, C. Y. (2001). Expression-independent consumption of substrates in cell-free expression system from Escherichia coli. J. Biotechnol. 84, 27-32.

Liu, D. V., Zawada, J. F., and Swartz, J. R. (2005). Streamlining Escherichia coli S30 extract preparation for economical cell-free protein synthesis. Biotechnol. Prog. 21, 460-465.

Lopez, P. J., Marchand, I., Joyce, S. A., and Dreyfus, M. (1999). The C-terminal half of RNase E, which organizes the *Escherichia coli* degradosome, participates in mRNA degradation but not rRNA processing in vivo. Mol. Microbiol. 33, 188-199.

Mertens, N., Remaut, E., and Fiers, W. (1996). Increased stability of phage T7g10 mRNA is mediated by either a 5'- or a 3'-terminal stem-loop structure. Biol. Chem. 377, 811-817.

Shine, J., and Dalgarno, L. (1974). The 3'-terminal sequence of *Escherichia coli* 16S ribosomal RNA: complementarity to nonsense triplets and ribosome binding sites. Proc. Natl. Acad. Sci. USA 71, 1342-1346.

We claim:

1. A method of producing an optimized mRNA sequence for protein expression in prokaryotes, comprising:

(i) selecting an mRNA sequence comprising an AU composition of less than 57% in the last 35 nucleotides of a protein coding region thereof;

(ii) altering the AU composition of the last 35 nucleotides of the protein coding region of the selected mRNA sequence to be at least 57% without changing the encoded amino acid sequence to produce an optimized mRNA sequence; and (iii) constructing an mRNA molecule comprising the optimized mRNA sequence.

2. A method of producing an optimized mRNA sequence for protein expression in prokaryotes, comprising:

(i) selecting an mRNA sequence comprising an AU composition of less than 57% in the last 35 nucleotides of a protein coding region thereof;

(ii) altering the AU composition of the last 35 nucleotides of the protein coding region of the selected mRNA sequence to be at least 57% without changing the encoded amino acid sequence, determining whether the AU composition of the first 35 nucleotides of a protein coding region of the mRNA sequence is less than 55%;

altering the AU composition of the first 35 nucleotides of the coding region of the selected mRNA sequence without changing the encoded amino acid sequence if the AU composition of the first 35 nucleotides of the coding region is less than 55%, such that the AU composition of the first 35 nucleotides of the coding region of the mRNA sequence is at least 55%; and altering the sequence of a first 35 nucleotides of the coding region of the selected mRNA sequence without changing the encoded amino acid sequence, such that the first 35 nucleotides of the coding region if the mRNA sequence is predicted to have less secondary structure relative to the first 35 nucleotides of the coding region of the selected mRNA sequence, wherein the coding region further comprises nucleotides between the first 35 nucleotides of the coding region and the last 35 nucleotides of the coding region, to produce an optimized mRNA sequence; and (iii) constructing an mRNA molecule comprising the optimized mRNA sequence.

3. A method of producing an optimized mRNA sequence for protein expression in prokaryotes, comprising:

(i) selecting an mRNA sequence comprising an AU composition of less than 57% in the last 35 nucleotides of a protein coding region thereof;

(ii) altering the AU composition of the last 35 nucleotides of the protein coding region of the selected mRNA sequence to be at least 57% without changing the encoded amino acid sequence, and at least two of determining whether the AU composition of the first 35 nucleotides of the protein coding region of the mRNA sequence is less than 55%; altering the AU composition of the first 35nucleotides of the coding region of the selected mRNA sequence without changing the encoded amino acid sequence if the composition of the first 35 nucleotides of the coding region is less than 55%, such that the AU composition of the first 35 nucleotides of the coding region of the mRNA sequence is at least 55%;

altering the sequence of a first 35 nucleotides of the coding region of the selected mRNA sequence without changing the encoded amino acid sequence, such that the first 35 nucleotides of the coding region of the mRNA sequence is predicted to have less secondary structure relative to the first 35 nucleotides of the coding region of the selected mRNA sequence;

altering the sequence of a last 35 nucleotides of the coding region of the selected mRNA sequence without changing the encoded amino acid sequence, such that the last 35 nucleotides of the coding region of the mRNA sequence is predicted to have less secondary structure relative to the last 35 nucleotides of the coding region of the selected mRNA sequence;

altering the sequence of the coding region of the selected mRNA sequence such that at least one codon is replaced with a codon that is used at higher frequency in a selected host cell; or altering the AU composition of a middle portion of the selected mRNA sequence, wherein the middle portion is between the first 35 nucleotides and the last 35 nucleotides of the coding region, to produce an optimized mRNA sequence; and (iii) constructing an mRNA molecule comprising the optimized mRNA sequence.

4. A method of producing an optimized mRNA sequence for protein expression in prokaryotes, comprising:

(i) selecting an mRNA sequence comprising an AU composition of less than 57% in the last 35nucleotides of a protein coding region thereof;

(ii) altering the AU composition of the last 35 nucleotides of the protein coding region of the selected mRNA sequence to be at least 57% without changing the encoded amino acid sequence, and at least three of:

determining whether the AU composition of the first 35 nucleotides of the protein coding region of the mRNA sequence is less than 55%; altering the AU composition of the first 35nucleotides of the coding region of the selected mRNA sequence without changing the encoded amino acid sequence if the composition of the first 35 nucleotides of the coding region is less than 55%, such that the AU composition of the first 35 nucleotides of the coding region of the mRNA sequence is at least 55%;

altering the sequence of a first 35 nucleotides of the coding region of the selected mRNA sequence without changing the encoded amino acid sequence, such that the first 35 nucleotides of the coding region of the mRNA sequence is predicted to have less secondary structure relative to the first 35 nucleotides of the coding region of the selected mRNA sequence;

altering the sequence of a last 35 nucleotides of the coding region of the selected mRNA sequence without changing the encoded amino acid sequence, such that the last 35 nucleotides of the coding region of the mRNA sequence is predicted to have less secondary structure relative to the last 35 nucleotides of the coding region of the selected mRNA sequence;

altering the sequence of the coding region of the selected mRNA sequence such that at least one codon is replaced with a codon that is used at higher frequency in a selected host cell; or altering the AU composition of a middle portion of the selected mRNA sequence, wherein the middle portion is between the first 35 nucleotides and the last 35 nucleotides of the coding region, to produce an optimized mRNA sequence; and (iii) constructing an mRNA molecule comprising the optimized mRNA sequence.

5. The method of claim 1, wherein said prokaryotes comprise *Escherichia coli* (*E. coli*) bacteria.

6. The method of claim 1, further comprising constructing a synthetic gene that encodes the optimized mRNA sequence.

7. The method of claim 1, further comprising producing a protein by expressing a synthetic gene encoding the optimized mRNA sequence in a prokaryotic cell.

8. The method of claim 1, wherein the selected mRNA sequence is the sequence of a naturally occurring mRNA molecule.

9. The method of claim 1, wherein altering the AU composition of the last 35nucleotides of the protein coding region of the selected mRNA sequence comprises site directed mutagenesis of a DNA sequence that encodes the selected mRNA sequence.

10. The method of claim 1, wherein altering the AU composition of the last 35nucleotides of the protein coding region of the selected mRNA sequence comprises synthetic gene assembly.

11. The method of claim 10, wherein the synthetic gene assembly comprises chemical synthesis.

12. The method of claim 1, wherein constructing an mRNA molecule comprising the optimized mRNA sequence comprises expressing a synthetic gene encoding the optimized mRNA sequence in a prokaryotic cell.

* * * * *